(12) United States Patent
Poon et al.

(10) Patent No.: US 11,350,876 B2
(45) Date of Patent: Jun. 7, 2022

(54) CAPTURING AND MEASURING TIMELINESS, ACCURACY AND CORRECTNESS OF HEALTH AND PREFERENCE DATA IN A DIGITAL TWIN ENABLED PRECISION TREATMENT PLATFORM

(71) Applicant: TWIN HEALTH, INC., Mountain View, CA (US)

(72) Inventors: Terrence Chun Yin Poon, Foster City, CA (US); Amit Shrivastava, Fremont, CA (US); Jahangir Mohammed, Los Gatos, CA (US); Lihuan Xie, Sunnyvale, CA (US)

(73) Assignee: Twin Health, Inc., Mountain View, CA (US)

( * ) Notice: Subject to any disclaimer, the term of this patent is extended or adjusted under 35 U.S.C. 154(b) by 0 days.

(21) Appl. No.: 17/202,354

(22) Filed: Mar. 16, 2021

(65) Prior Publication Data

US 2021/0196196 A1    Jul. 1, 2021

Related U.S. Application Data

(63) Continuation of application No. 16/993,189, filed on Aug. 13, 2020.

(Continued)

(30) Foreign Application Priority Data

Aug. 13, 2019  (IN) .............................. 201941032787
Sep. 14, 2019  (IN) .............................. 201941037052

(51) Int. Cl.
*A61B 5/00*     (2006.01)
*G16H 50/30*    (2018.01)
(Continued)

(52) U.S. Cl.
CPC .......... *A61B 5/4866* (2013.01); *A61B 5/1118* (2013.01); *A61B 5/14532* (2013.01);
(Continued)

(58) Field of Classification Search
CPC ... A61B 5/4866; A61B 5/1118; A61B 5/4833; A61B 5/486; A61B 5/6802; A61B 5/7275; G16H 20/60; G16H 50/30; G09B 19/0092
(Continued)

(56) References Cited

U.S. PATENT DOCUMENTS 10,687,742 B2   6/2020  Lange et al.
10,863,912 B2  12/2020  Starr et al.
(Continued)

FOREIGN PATENT DOCUMENTS

| CA | 2968645 A1 | 7/2016 |
| WO | WO 2016/038585 A1 | 3/2016 |
| WO | WO 2016/110804 A1 | 7/2016 |

OTHER PUBLICATIONS

International Search Report and Written Opinion, Patent Cooperation Treaty Application No. PCT/US2020/046249, dated Oct. 30, 2020, forty pages.

(Continued)

*Primary Examiner* — John R Downey
(74) *Attorney, Agent, or Firm* — Fenwick & West LLP

(57) ABSTRACT

A patient health management platform determines of a metabolic state for a first time period. The platform generates a patient-specific treatment recommendation for a second time period following the first time period that identifies objectives for the patient to complete to improve the metabolic state determined for the first time period. Periodically during the second time period, the platform receives recordings of patient data indicating foods consumed by the (Continued)

patient, medication taken by the patient, and/or symptoms experienced by the patient. The platform compares the received recordings of patient data from the second time period to the generated patient-specific treatment recommendation to determine a number of objectives completed by the patient and updates a score representing n adherence of the patient to the patient-specific treatment recommendation based the number of completed objectives. The platform provides the patient-specific treatment recommendation to the patient device for display to the patient.

24 Claims, 23 Drawing Sheets

Related U.S. Application Data

(60) Provisional application No. 62/989,557, filed on Mar. 13, 2020, provisional application No. 62/894,049, filed on Aug. 30, 2019.

(51) Int. Cl.
| | |
|---|---|
| *G16H 40/67* | (2018.01) |
| *G16H 50/20* | (2018.01) |
| *G16H 15/00* | (2018.01) |
| *A61B 5/11* | (2006.01) |
| *A61B 5/145* | (2006.01) |
| *G16H 20/10* | (2018.01) |
| *G16H 20/60* | (2018.01) |
| *G16H 10/40* | (2018.01) |
| *G16H 50/50* | (2018.01) |
| *G16H 10/60* | (2018.01) |
| *G06N 20/00* | (2019.01) |
| *A61B 5/0205* | (2006.01) |

(52) U.S. Cl.
CPC ............ *A61B 5/486* (2013.01); *A61B 5/4833* (2013.01); *A61B 5/6801* (2013.01); *A61B 5/6802* (2013.01); *A61B 5/7267* (2013.01); *A61B 5/7275* (2013.01); *A61B 5/742* (2013.01); *A61B 5/749* (2013.01); *A61B 5/7475* (2013.01); *G06N 20/00* (2019.01); *G16H 10/40* (2018.01); *G16H 10/60* (2018.01); *G16H 15/00* (2018.01); *G16H 20/10* (2018.01); *G16H 20/60* (2018.01); *G16H 40/67* (2018.01); *G16H 50/20* (2018.01); *G16H 50/30* (2018.01); *G16H 50/50* (2018.01); *A61B 5/0205* (2013.01)

(58) Field of Classification Search
USPC .......................................... 600/301; 434/127
See application file for complete search history.

(56) References Cited

U.S. PATENT DOCUMENTS

| | | | |
|---|---|---|---|
| 10,945,675 B2 | 3/2021 | Jain et al. | |
| 10,952,638 B2 | 3/2021 | Lange | |
| 2005/0228239 A1 | 10/2005 | Shallenberger | |
| 2010/0049004 A1 | 2/2010 | Edman et al. | |
| 2010/0262117 A1* | 10/2010 | Magni ................. | A61M 5/1723 |
| | | | 604/504 |
| 2010/0280329 A1* | 11/2010 | Randlov ................ | G16H 50/50 |
| | | | 600/300 |
| 2012/0016678 A1 | 1/2012 | Gruber et al. | |
| 2012/0271612 A1* | 10/2012 | Barsoum ................ | G16H 50/50 |
| | | | 703/11 |
| 2013/0216989 A1 | 8/2013 | Cuthbert | |
| 2015/0051917 A1* | 2/2015 | Nikolova-Simons ....................... | |
| | | | G16H 20/30 |
| | | | 705/2 |
| 2015/0282767 A1 | 10/2015 | Stivoric et al. | |
| 2016/0371998 A1* | 12/2016 | Fazeel .................... | G16H 20/70 |
| 2017/0055875 A1 | 3/2017 | Candell et al. | |
| 2017/0249445 A1 | 8/2017 | DeVries et al. | |
| 2017/0323582 A1* | 11/2017 | Nusbaum ............... | G09B 19/00 |
| 2018/0169332 A1* | 6/2018 | Sadeghzadeh ........ | A61M 5/145 |
| 2018/0182490 A1* | 6/2018 | Fakhrai-Rad .......... | G16H 50/30 |
| 2018/0233064 A1* | 8/2018 | Dunn .................. | G06F 16/9535 |
| 2018/0316781 A1* | 11/2018 | Salem .................. | H04L 67/306 |
| 2018/0344259 A1 | 12/2018 | Pavlov et al. | |
| 2019/0252079 A1* | 8/2019 | Constantin .......... | A61B 5/7475 |
| 2021/0045694 A1 | 2/2021 | Hadley et al. | |

OTHER PUBLICATIONS

United States Office Action, U.S. Appl. No. 17/202,352, filed Apr. 30, 2021, thirteen pages.
United States Office Action, U.S. Appl. No. 17/202,353, filed May 5, 2021, eleven pages.
United States Office Action, U.S. Appl. No. 17/202,352, filed Aug. 13, 2021, 15 pages.
United States Office Action, U.S. Appl. No. 16/993,177, filed Oct. 25, 2021, 14 pages.
United States Office Action, U.S. Appl. No. 17/202,352, filed Jan. 6, 2022, 6 pages.
United States Office Action, U.S. Appl. No. 16/993,177, filed Apr. 6, 2022, 18 pages.
United States Office Action, U.S. Appl. No. 17/202,352, filed Apr. 6, 2022, 7 pages.

* cited by examiner

Medication

Today

✓ MICRO AND BIOTA NUTRIENT

Morning Empty Stomach
○ 1.0 tablespoons of E5 coconut oil

Before Breakfast
○ 1000.0 mg Metformin
○ 2.0 mg Glimepiride

With Breakfast
○ 1.0 tablespoon(s) of Flax Seeds Powder

Before Dinner
○ 1000.0 mg Metformin
○ 2.0 mg Glimepiride

After Dinner
○ 2 tablets Multivitamin / Minerals (1 Myokcamp, 1 Vitabrace)

Anytime

CAPTURING AND MEASURING TIMELINESS, ACCURACY AND CORRECTNESS OF HEALTH AND PREFERENCE DATA IN A DIGITAL TWIN ENABLED PRECISION TREATMENT PLATFORM

CROSS REFERENCE TO RELATED APPLICATIONS

This application is a continuation of U.S. Non-Provisional application Ser. No. 16/993,189, filed Aug. 13, 2020, which claims the benefit of Indian Provisional Application No. 201941032787, filed on Aug. 13, 2019, U.S. Provisional application No. 62/894,049, filed on Aug. 30, 2019, Indian Provisional Application No. 201941037052, filed on Sep. 14, 2019, and U.S. Provisional application No. 62/989,557, filed on Mar. 13, 2020, each of which is incorporated by reference in its entirety.

BACKGROUND

Field of Art

The disclosure relates generally to a patient health management platform, and more specifically, to a personalized treatment platform for managing the metabolic health of a patient using continuously/continually collected biosignals.

Description of the Related Art

In the United States, health care costs approximately $3.2 trillion annually. Of that, 75% is attributed to diseases related to metabolic dysfunction, for example type 2 diabetes, hypertension, lipid problems, heart disease, non-alcoholic fatty liver disease, polycystic ovarian syndrome, cancer, and dementia. In the United States alone, metabolic diseases affect more than 100 million people, resulting in significant increases in medical costs. Nearly 425 million adults across the globe live with diabetes with close to 325 million at risk of Type 2 diabetes. In 2017, diabetes alone was the cause of $727 billion dollars in health expenditure and that number has continued to grow every year. Thus far, the medical community has seen type 2 diabetes as a chronic and progressive disease. Once diagnosed, it is a life sentence. Medications may improve blood sugar levels (the symptom), but do not address the actual disease—diabetes. Moreover, the management of diabetes treatments involve costly medications, painful insulin injections, constant finger pricks, dietary restrictions, and other factors that result in a general loss in quality of life. Worse, diabetic patients suffer from weakened immune systems, potential tissue death and amputation, numbness, increased risk of heart disease, and a multitude of other medical ailments.

Conventional disease management platforms or techniques either ignore or fail to fully understand important markers, such as blood sugar dysregulation, and root causes for these diseases, such as processed foods and a lack of exercise. Traditionally, these platforms are designed to treat symptoms as they arise rather than treating the root cause of the disease—the deterioration of a patient's metabolic health. Platforms that have attempted to treat metabolic diseases focused on an "average" patient rather than tailoring their treatment and management regimens to the specific metabolic health of each patient. Accordingly, such platforms prescribe suboptimal treatments that have diminished efficacy or unwanted side effects (e.g., prescribing excessive medication) for patients.

Additionally, conventional disease management platforms struggle to address two challenges. First, they are unable to acquire relevant biosignal data in a timely manner, validate the accuracy of any acquired biosignal data, and ensure the completeness of ongoing data collection so that a resulting treatment recommendation may be trusted. Second, these platforms are unable to achieve high patient adherence to their prescribed treatment recommendations. Traditional approaches attempt to manually acquire such data and monitor patient adherence, which results in delayed, inaccurate and inconsistent results.

SUMMARY

A patient health management platform for managing a patient's metabolic diseases generates a precision treatment using machine learning techniques and analyzing a unique combination of continuous biosignals from one or more of the following sources: near real-time biological data recorded by wearable sensors, biological data recorded by lab tests, nutrition data, medicine data, and patient symptoms. The platform performs various analyses to establish a personalized metabolic profile for each patient by gaining a deep understanding of how the combination of continuous biosignals impact the patient's metabolic health. The platform generates a time series of metabolic states based on biosignals continuously/regularly recorded for a period of time, which allows the platform to gain insight into not only the patient's current metabolic state at particular time points within a day/time period, but also a complete history of metabolic states that led to that current metabolic state (e.g., a collection of metabolic states at multiple time points across preceding days/time periods). These biosignals are input into a machine-learned model(s) that recommends personalized treatment based on a unique metabolic profile of the patient.

The machine-learned model(s) are trained based on a large body of historical patient data including daily metabolic inputs (e.g., labeled metabolic states and input biosignals) and daily metabolic outputs (e.g., changes in metabolic states for a population of patients). Accordingly, the model is trained to predict responses to future input biosignals, not just for the patients in the training set, but also for completely new patients based on their metabolic states and input biosignals. As a result of such training, the model does not need to be re-trained for new patients. The model can also predict responses to input biosignals for each patient at different stages of his or her treatment, since each patient's metabolic state changes throughout the treatment.

Based on the output of the machine-learned model, the patient health management platform generates personalized recommendations for a patient outlining a treatment plan for improving the patient's metabolic health. For example, the patent health management platform may generate a personalized recommendation including a personalized nutrition plan, a medication plan, and an exercise and sleep regimen. The recommendations can additionally be time-specific, including recommendations to perform specific actions at particular time points (e.g., eating a specific amount of a specific food at 3 pm). These recommendations may be reviewed by doctors and coaches to improve their accuracy and usefulness before being delivered to a patient via an application interface on a mobile device. Over time, as a patient follows these recommendations, the platform captures changes in their metabolic state to dynamically quantify the impact of each recommendation. The captured changes and quantifications further serve as a feedback loop to refine and optimize the recommended treatments.

To confirm that a patient-specific recommendation effectively addresses a patient's metabolic health, the patient health management evaluates the patient data recorded by a patient to confirm the timeliness, accuracy, and completeness of the recorded data. A timelines measurement evaluates the time delay between when event data (e.g., nutrition or symptom data) occurred and when it was recorded by the patient. An accuracy measurement evaluates whether data was misreported or is otherwise inaccurate (e.g., whether a food item was omitted from a record of entered nutrition data). A completeness measurement evaluates whether any critical data is missing from a record of patient data. To measure these aspects of a patient's record of patient data, the patient health management platform generates a prediction of what a patient's metabolic state should be based on information recorded by the patient. The patient health management platform compares the predicted metabolic state against the patient's true metabolic state and flags any inconsistencies. In some instances, the flagged inconsistencies are attributed to errors in a patient's recordation of data. To encourage improvements in the above metrics, the patient health management platform may evaluate a patient's record of entries by assigning the patient a timeliness/accuracy/completeness (TAC) score and dynamically updating the TAC score based on the patient's subsequent patient data entries.

BRIEF DESCRIPTION OF DRAWINGS

FIGS. 13A-13L illustrate exemplary graphical user interfaces for evaluating a patient's TAC scores via a patient device, according to one embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
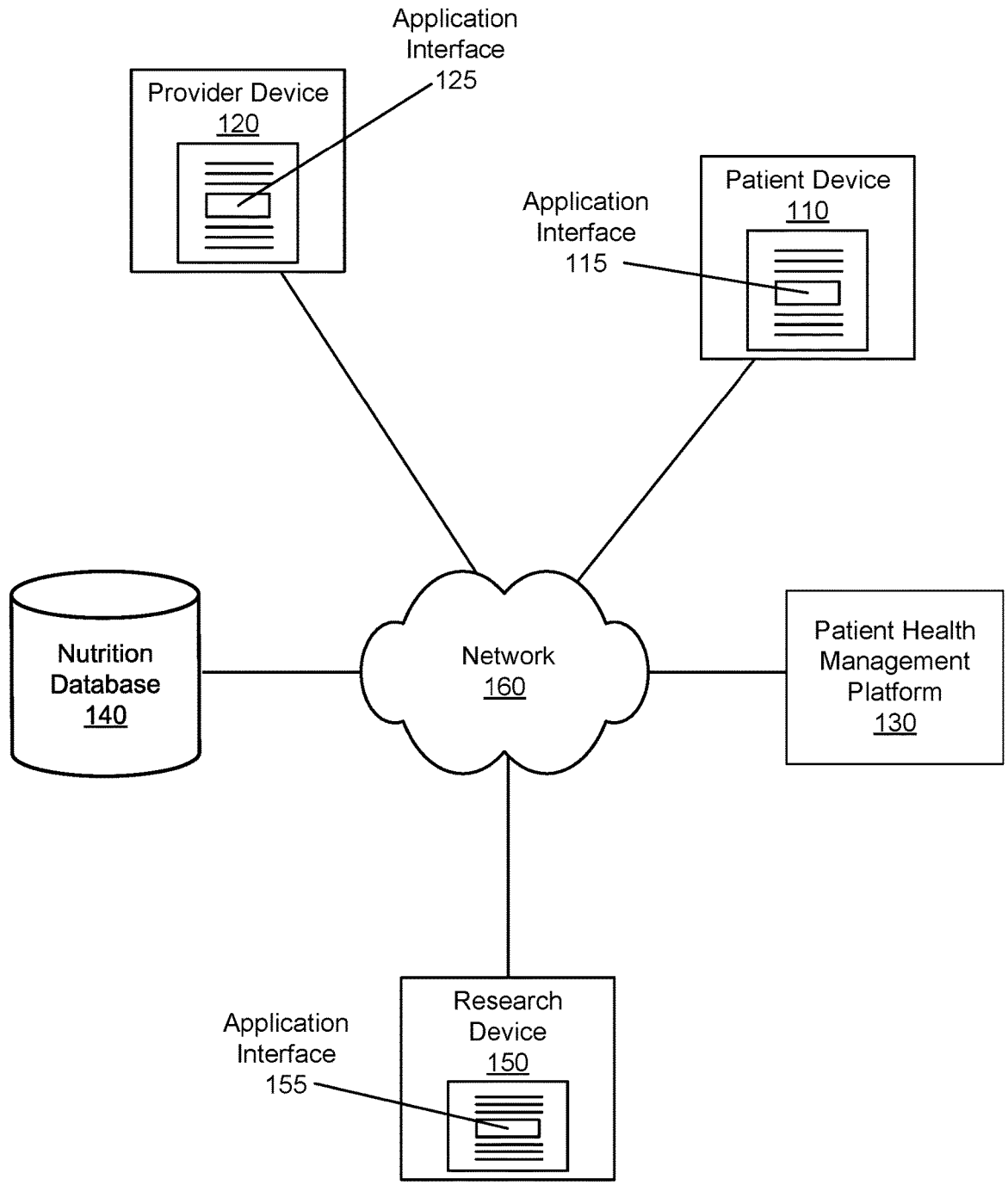
FIG. 1 shows a metabolic health manager for monitoring metabolic health of a patient, performing analytics on the metabolic health data, and providing a patient-specific recommendation for treating metabolic health-related concerns, according to one embodiment.

FIG. 1 shows a metabolic health manager 100 for monitoring a patient's metabolic health, for performing analytics on metabolic health data recorded for the patient, and for generating a patient-specific recommendation for treating any metabolic health-related concerns, according to one embodiment. The metabolic health manager 100 includes patient device(s) 110, provider device(s) 120, a patient health management platform 130, a nutrition database 140, research device(s) 150 and a network 160. However, in other embodiments, the system 100 may include different and/or additional components. For example, the patient device 110 can represent thousands or millions of devices for patients (e.g., patient mobile devices) that interact with the system in locations around the world. Similarly, the provider device 120 can represent thousands or millions of devices of providers (e.g., mobile phones, laptop computers, in-provider-office recording devices, etc.). In some cases, a single provider may have more than one device that interacts with the platform 130.

The patient device 110 is a computing device with data processing and data communication capabilities that is capable of receiving inputs from a patient. An example physical implementation is described more completely below with respect to FIG. 2. In addition to data processing, the patient device 110 may include functionality that allows the device 110 to record speech responses articulated by a patient operating the device (e.g., a microphone), and to graphically present data to a patient (e.g., a graphics display). Examples of the patient device 110 include desktop computers, laptop computers, portable computers, GOOGLE HOME, AMAZON ECHO, etc. The patient device 110 may present information generated by the communication platform 130 via a mobile application configured to display and record patient responses. For example, through a software application interface 115, a patient may receive a recommendation or an update regarding their metabolic health.

Application 115 provides a user interface (herein referred to as a "patient dashboard") that is displayed on a screen of the patient device 110 and allows a patient to input commands to control the operation of the application 115. The patient dashboard enables patients to track and manage changes in a patient's metabolic health. For example, the dashboard allows patients to observe changes in their metabolic health over time, receive recommendation notifications, exchange messages about treatment with a health care provider, and so on. The application 115 may be coded as a web page, series of web pages, or content otherwise coded to render within an internet browser. The application 115 may also be coded as a proprietary application configured to operate on the native operating system of the patient device 110. In addition to providing the dashboard, application 115 may also perform some data processing on biological and food data locally using the resources of patient device 110 before sending the processed data through the network 150. Patient data sent through the network 150 is received by the patient health management platform 130 where it is analyzed and processed for storage and retrieval in conjunction with a database.

Similarly, a provider device 120 is a computing device with data processing and data communication capabilities that is capable of receiving input from a provider. The provider device 120 is configured to present a patient's medical history or medically relevant data (i.e., a display screen). The above description of the functionality of the patient device 110 also can apply to the provider device 120. The provider device 120 can be a personal device (e.g., phone, tablet) of the provider, a medical institution computer (e.g., a desktop computer of a hospital or medical facility), etc. In addition, the provider device 120 can include a device that sits within the provider office such that the patient can interact with the device inside the office. In such implementations, the provider device is a customized device with audio and/or video capabilities (e.g., a microphone for recording, a display screen for text and/or video, an interactive user interface, a network interface, etc.). The provider device 120 may also present information to medical providers or healthcare organizations via a mobile application similar to the application described with reference to patient device 110.

Application 125 provides a user interface (herein referred to as a "provider dashboard") that is displayed on a screen of the provider device 120 and allows a medical provider or trained professional/coach to input commands to control the operation of the application 125. The provider dashboard enables providers to track and manage changes in a patient's metabolic health. The application 125 may be coded as a web page, series of web pages, or content otherwise coded to render within an interne browser. The application 125 may also be coded as a proprietary application configured to operate on the native operating system of the patient device 110.

The patient health management platform 130 is a medium for dynamically generating recommendations for improving a patient's metabolic health based on biological data recorded from a plurality of sources including wearable sensors (or other types of IoT sensors), lab tests, etc., and food or diet-related data recorded by the patient. The patient health management platform 130 predicts a patient's metabolic response based on periodically recorded patient data (e.g., nutrition data, symptom data, lifestyle data). Accordingly, a patient's metabolic response describes a change in metabolic health for a patient resulting from the food they most recently consumed and their current metabolic health. Based on such a change, the platform 130 generates a recommendation including instructions for a patient to improve their metabolic health or to maintain their improved metabolic health. Additionally, in real-time or near real-time, the patient health management platform 130 may provide feedback to a patient identifying potential inconsistencies or errors in the food or biological data entered manually by the patient based on a comparison of the patient's true metabolic state and their predicted metabolic state.

The nutrition database 140 stores nutrition data extracted from a collection of nutrient sources, for example food or vitamins. Data within the nutrition database 140 may be populated using data recorded by a combination of public sources and third-party entities such as the USDA, research programs, or affiliated restaurants. The stored data may include, but is not limited to, nutrition information (for example, calories, macromolecule measurements, vitamin concentrations, cholesterol measurements, or other facts) for individual foods or types of foods and relationships between foods and metabolic responses (for example, an impact of a given food on insulin sensitivity). Data stored in the nutrition database 140 may be applicable to an entire population (i.e., general nutrition information) or personalized to an individual patient (i.e., a personalized layer of the nutrition database). For example, the nutrition database 140 may store information describing a patient's particular biological (i.e., metabolic) response to a food. In such embodiments, the nutrition database 140 may be updated based on feedback from the patient health management platform 140.

In some embodiments, for example the embodiment illustrated in FIG. 1, the analytics system 100 additionally comprises a research device 150 that analyzes information generated by the patient health management platform to analyze a patient's metabolic response. For example, the research device 150 may receive a patient's current metabolic state, their previous metabolic state, and a treatment recommendation that contributed to the current metabolic state. By continuously comparing current metabolic state and the previous metabolic state, the research device 150 may evaluate the effectiveness of the treatment recommendation as a whole. Alternatively, the research device 150 may evaluate the effectiveness of certain aspects of the treatment recommendation. The research device 150 is a computing device capable of receiving input from a provider with data processing and data communication capabilities. The research device 150 is configured to present a patient's medical history or medically relevant data (i.e., a display screen). The above description of the functionality of the patient device 110 and the provider device 120 also can apply to the research device 150. The research device 150 can be a personal device (e.g., phone, tablet) of the provider, a medical institution computer (e.g., a desktop computer of a hospital or medical facility), etc. In addition, the provider device 150 can include a device that sits within the research office such that a patient can interact with the device inside the office. In such implementations, the research device 150 is a customized device with audio and/or video capabilities (e.g., a microphone for recording, a display screen for text and/or video, an interactive user interface, a network interface, etc.). The research device 150 may also present information to a research team via a mobile application similar to the application described with reference to patient device 110.

Application 155 provides a user interface (herein referred to as a "research dashboard") that is displayed on a screen of the research device 150 and allows a researcher to input commands to control the operation of the application 155. The research dashboard enables providers to track and manage changes in a patient's metabolic health. The application 155 may be coded as a web page, series of web pages, or content otherwise coded to render within an internet browser. The application 155 may also be coded as a proprietary application configured to operate on the native operating system of the patient device 110.

Interactions between the patient device 110, the provider device 120, the patient health management platform 130, and the nutrition database 140 are typically performed via the network 150, which enables communication between the patient device 120, the provider device 130, and the patient communication platform 130. In one embodiment, the network 150 uses standard communication technologies and/or protocols including, but not limited to, links using technologies such as Ethernet, 802.11, worldwide interoperability for microwave access (WiMAX), 3G, 4G, LTE, digital subscriber line (DSL), asynchronous transfer mode (ATM), InfiniBand, and PCI Express Advanced Switching. The network 150 may also utilize dedicated, custom, or private communication links. The network 150 may comprise any combination of local area and/or wide area networks, using both wired and wireless communication systems.

Figure 2:
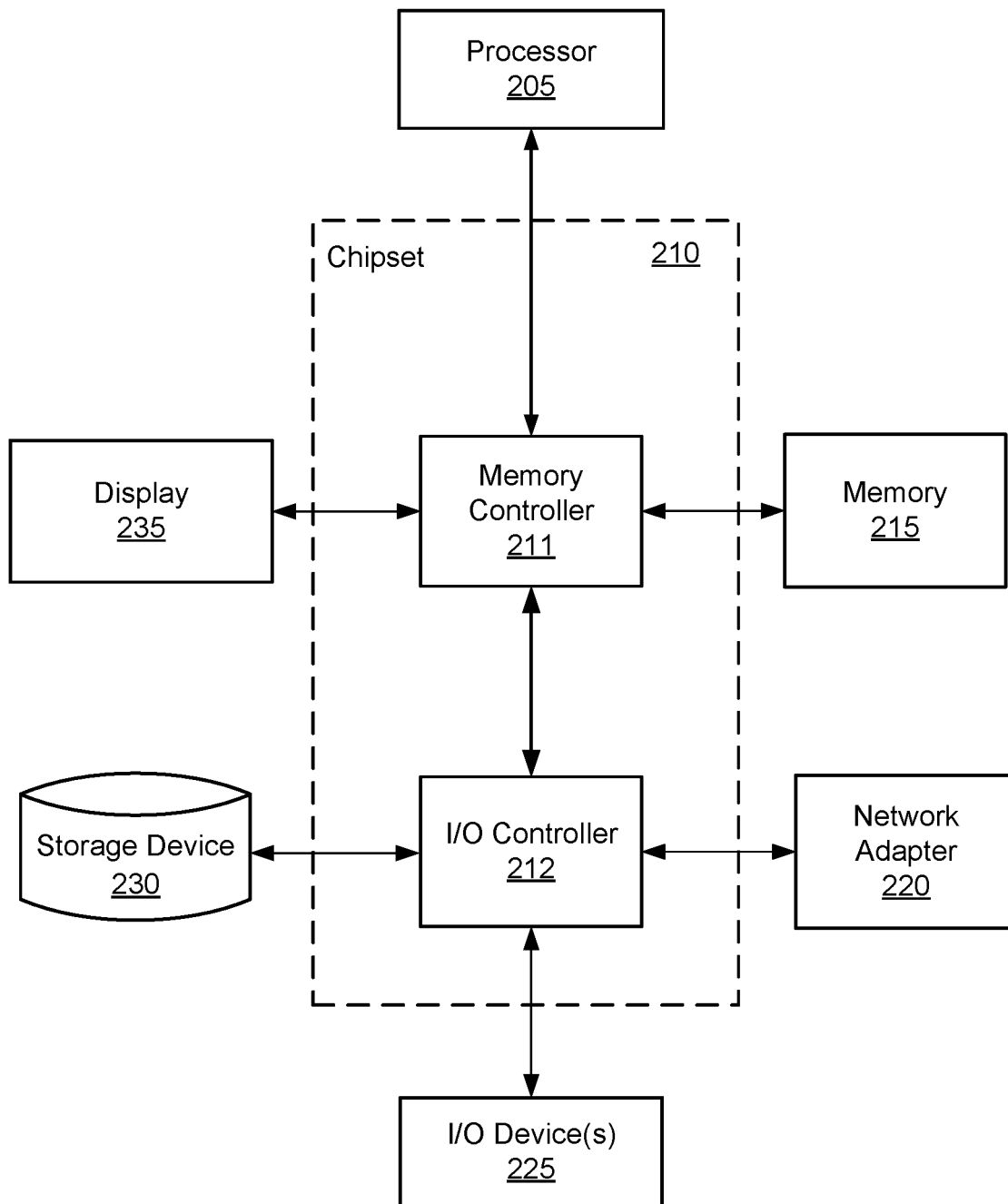
FIG. 2 is a high-level block illustrating an example of a computing device used in either as a client device, application server, and/or database server, according to one embodiment.

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a non-volatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

II. Overview of Metabolic Health Manager

In the United States, treating non-communicable diseases including, but not limited to, diabetes, hyper-tension, high-cholesterol, heart disease, obesity, fatty liver disease, arthritis, irritable bowel syndrome (IBS), and infertility, is a multi-billion-dollar industry. Still, these diseases account for over 2 million deaths annually. Conventional treatments are directed towards addressing and alleviating symptoms of each disease, but fail to recognize that the root of all the aforementioned diseases is an impaired metabolism. By addressing root cause metabolic impairments, a patient's disease may not just be managed on a per symptom basis, but reversed entirely. Accordingly, a treatment or system for generating a treatment directed towards treating metabolic impairments in patients suffering from such diseases could be more effective and most cost-efficient. Because the patient health management platform 100 aims to treat a patient's metabolic impairments, a patient using the patient health management platform 100 for an extended period of time may transition from a first state of impaired metabolism to a second state of functional metabolism to a third state of optimal metabolism.

The patient health management platform 130, as described herein, recognizes that a patient's body is a unique system in a unique state in which metabolism is a core biochemical process. Accordingly, the treatment and nutrition recommendations generated by the platform 130 are tailored to suit a patient's unique metabolic state and the unique parameters or conditions that impact or have previously impacted their metabolic state. To enable a patient to achieve good or optimal metabolic health, the platform 130 records measurements of various factors and aims to improve these measurements to levels representative of an optimized metabolic state. For example, five factors commonly considered include blood sugar, triglycerides, good cholesterol (high-density lipoprotein), blood pressure, and waist circumference. Each human body is different and continuously evolving. To guide a patient towards optimal metabolic health, the platform establishes a deep understanding of the dynamic states of each human body over time by capturing continuous biosignals and deriving insights from these biosignals.

For each patient, the platform 130 leverages a combination of personalized treatments that are tailored to a patient's unique metabolic state based on a combination of timely, accurate, and complete recordings of metabolic biosignals. Such measurements are collectively referred to herein as "TAC measurements." The platform determines a current metabolic state of a human body by analyzing a unique combination of continuous biosignals received from various sources including, but not limited to, near-real-time data from wearable sensors (e.g. continuous blood glucose, heart rate, etc.), periodic lab tests (e.g., blood work), nutrition data (e.g., macronutrients, micronutrients, and biota nutrients from food and supplements of the patient), medicine data (e.g., precise dosage and time of medications taken by the patient), and symptom data (e.g., headache, cramps, frequent urination, mood, energy, etc., reported by each patient via a mobile app). This analysis is performed continuously to establish a time series of metabolic states. As a result, the platform understands not only the current state of each patient, but also the full history of states that led to the current state. Using a patient's current metabolic state and their full history of metabolic states, the platform is able to deeply personalize the treatment for each patient.

The platform applies various technologies and processing techniques to gain a deep understanding of the combination of factors contributing to a patient's metabolic state and to establish a personalized metabolic profile for each patient. For example, the platform implements a combination of analytics (e.g., analyzing trends, outliers, and anomalies in biosignals as well as correlations across multiple biosignals), rule based artificial intelligence (AI), machine learning-based AI, and automated cohorting or clustering.

For the sake of explanation, the concepts and techniques described herein are described with reference to diabetes. However, one of skill in the art would recognize that the concepts and techniques may also be applied to any other disease resulting from an impaired metabolism. As will be described herein, a patient's metabolic health describes the overall effectiveness of their metabolism. For example, a patient's metabolic health may be categorized as impaired, functional, or optimal. To gain insight into a patient's metabolic health, the patient health management platform 130 identifies metabolic states occurring over a period of time and changes between those metabolic states. As described herein, a metabolic state represents a patient's state of metabolic health at a specific time (e.g., a state of metabolic health resulting from consumption of a particular food or adherence to a particular medication/treatment).

In addition, the term "continuously" is used throughout the description to characterize the collection of biosignals and other data regarding the patient. This term can refer to a rate of collection that is truly continuous (e.g., a constantly recorded value) or near continuous (e.g., collection at every time point or time increment, such as every millisecond, second, or minute), such as biosignals recorded by a wearable device. In some cases, continuously recorded data may refer to particular biosignals that occur semi-regularly, such as a lab test that is taken at a recurring time interval (e.g., every 10 minutes, 30 minutes, hour, 5 hours, day or number of days, week or number of weeks, etc.). The term "continuously" does not exclude situations in which wearable sensors may be removed during certain activities or at times of day (e.g., while showering). In other embodiments, the platform collects multiple biosignals that, in combination, represent a continuous or near continuous signal collection even though some biosignals are collected more frequently than others.

Figure 3A:
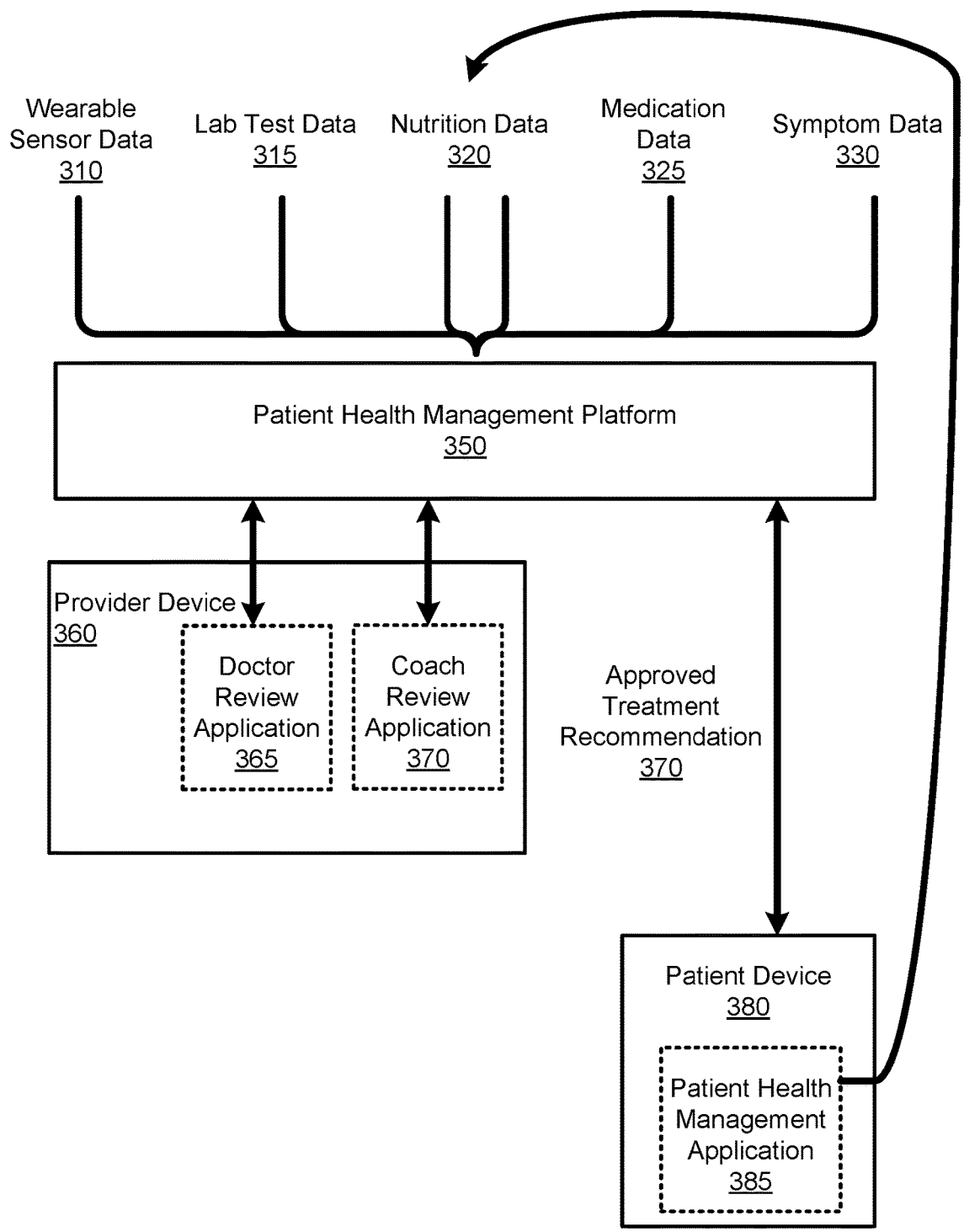
FIG. 3A is an illustration of the interactions between various components of the metabolic health manager involved in generating and providing a patient-specific recommendation to a patient, according to one embodiment.

FIG. 3A is an illustration of the interactions between various components of the metabolic health manager 100 that are involved in generating and providing a patient-specific recommendation, according to one embodiment. A patient health management platform 350 receives biosignals recorded for a patient by a variety of sources at varying intervals. The patient health management platform 350 continues to receive biosignal data from each source and, as data is received, assigns the biosignal data to a particular metabolic state. Accordingly, the platform 350 continuously augments a patient's current metabolic state with biosignal data and continuously refines recommendations based on the current metabolic state. Types of biosignal data include, but are not limited to, wearable sensor data 310, lab test data 315, nutrition data 320, medication data 325, and symptom data 330. Biosignal input data is further described below in Section III Biosignal Data.

Based on the combination of received biosignals, the patient health management platform 350 generates a patient-specific recommendation describing a treatment to improve or maintain a patient's metabolic health in the long-term. Alternatively, the patient-specific recommendation describes a treatment to improve or maintain a patient's metabolic heath more immediately, for example a subsequent metabolic state. The patient health management platform 350 implements a combination of analytic techniques to process the combination of biosignals into a holistic representation of a patient's metabolic health. The patient health management platform 350 implements a first combination of metabolic models to generate a representation of a patient's true, metabolic state (or metabolic response) based on the most recently recorded wearable sensor data 310 and lab test data 315. Each metabolic model may be trained based on a training dataset of recorded biosignal data and known metabolic states. Accordingly, over time, the patient health management platform 350 generates a comprehensive record of how a patient's metabolic health has either improved, deteriorated, or been maintained in the form of a time sequence of metabolic states recorded for a period of time.

The patient health management platform 350 additionally implements a second combination of metabolic models to output a predicted metabolic response based on nutrition data, medication data, and symptom data recorded by a patient. During an initialization period when a patient first begins using the platform 350, the platform 350 accesses a set of metabolic states output by each metabolic model. From the accessed set of metabolic states, the platform 350 identifies correlations between changes in the metabolic states and the nutrient data, the medication data, and the symptom data recorded during the initialization period. In this way, the platform 350 may be configured to generate a prediction of a patient's current metabolic state based on the most recently entered nutrition data 320, medication data 325, and symptom data 330. For a given period of time, the patient health management platform 350 may compare the predicted metabolic state with the true metabolic state to verify the accuracy and precision of a patient's recorded entries (e.g., recorded nutrition data, medication data, and symptom data). Additionally, as a patient continues to use the platform 350, certain correlations identified by each metabolic model are either confirmed as consistently relevant correlations or ignored as single instance anomalies. The metabolic model may be adjusted or, over time, be updated to consider one or more of the consistently relevant correlations in the generation of the metabolic model.

Based on a patient's true metabolic response, the patient health management platform 350 generates a recommendation to improve or maintain the patient's metabolic health. The recommendation is a patient-specific set of instructions for treating a patient's metabolic health. As will be described below, the patient health management platform 350 determines biological factors that contribute to a patient's deteriorated metabolic health and generates a personalized recommendation to guidelines for the patient to address those biological deficiencies. with instructions to improve those biological factors. The patient health management platform 350 may also determine biological factors that contribute to a patient's improved metabolic health and generate a personalized recommendation with guidelines for the patient to maintain those biological factors. A treatment recommendation may be a combination of several recommendations including, but not limited to, a medication regimen recommendation, a nutrition regimen recommendation, and a lifestyle recommendation. As described herein, a medication regimen recommendation may include a list of recommended medications, a recommended dosage for each medication, and a recommendation adherence schedule for each medication. In some implementations, a treatment recommendation also includes a list of alternate medications with similar medical effects to the recommended medications or treatments. A nutrition recommendation may include a list of foods that a patient can consume to supplement any macromolecules, micromolecules, or biota molecules in which they are deficient. The patient health management platform 350 may generate several different nutrition recommendations based on foods which are preferred by the patient or based on foods which are readily available to the patient. The lifestyle recommendation may include a recommended amount of physical activity or sleep to improve a patient's metabolism.

The patient health management platform 350 communicates the treatment recommendation to a provider device 360, where a doctor may review the recommendation to confirm its medical accuracy or effectiveness via a doctor review application interface 365. The patient health management platform 350 may also communicate the recommendation to a provider device 360, where a metabolic health coach may review the recommendation to confirm the practicality and ease of adherence of a patient to the recommendation via a coach review application 370. In some implementations, (e.g., during a training period) the platform 350 may communicate a recommendation to a doctor or a health coach for review until the platform 350 has sufficient insight to accurately understand how nutrition, treatment, and lifestyle changes will affect an individual patient's metabolic health. Until the platform 350 has sufficient insight into the kinds of nutrition, treatment, and lifestyle changes that are not only conducive for a patient, the platform 350 ma communicate treatment recommendations to a provider device, a patient device, or both for approval by a metabolic health coach or doctor. In implementations in which the doctor or coach revises or adjusts a treatment recommendation, the revised treatment recommendation is returned to the patient health management platform 350.

The approved treatment recommendation 370 is communicated to a patient device 380, which presents the recommendation to a patient via the patient health management application 385. By interacting with the patient health management application 385, the patient reviews the treatment recommendation, tracks their progress through the treatment recommendation, and receives notifications generated by the platform regarding changes in their metabolic health. In some implementations, the patient health management application 385 may receive information from the patient health management platform 380 identifying inconsistencies or errors in information recorded using the application 385 and request that the patient correct the identified errors. Examples of such identified errors include, but are not limited to, incorrectly recording the time at which food or medication was consumed, incorrectly recording the amount of food or medication consumed, forgetting to record that a food or medication was consumed, or incorrectly recording which food or medication was consumed.

III. Biosignal Data

A patient health management platform 350 receives biosignal data for a patient from a variety of sources including, but not limited to, wearable sensor data 310, lab test data 315, nutrition data 320, medication data 325, symptom data 330.

A patient using the metabolic health manager is outfitted with one or more wearable sensors configured to continuously record biosignals, herein referred to as wearable sensor data 310. Wearable sensor data 310 includes, but is not limited to, biosignals describing a patient's heart rate, record of exercise (e.g., steps, average number of active minutes), quality of sleep (e.g., sleep duration, sleep stages), a blood glucose measurement, a ketone measurement, systolic and diastolic blood pressure measurements, weight, BMI, percentage of fat, percentage of muscle, bone mass measurement, and percent composition of water. A wearable sensor may be a sensor that is periodically removable by a patient (e.g., a piece of jewelry worn in contact with a patient's skin to record such biosignals) or a non-removable device/sensor embedded into a patient's skin (e.g., a glucose patch). Whenever worn or activated to record wearable sensor data 310, the sensor continuously records one or more of the measurements listed above. In some implementations, a wearable sensor may record different types of wearable sensor data 310 at different rates or intervals. For example, the wearable sensor may record blood glucose measurements, heart rate measurements, and steps in 15 second intervals, but record blood pressure measurements, weight measurements, and sleep trends in daily intervals.

The patient health management platform 350 also receives lab test data 315 recorded for a patient. As described herein, lab test data 315 describes the results of lab tests performed on the patient. Examples of lab test data 315 include, but are not limited to, blood tests or blood draw analysis. Compared to the frequencies at which wearable sensor data 310 is recorded, lab test data 315 may be recorded at longer intervals, for example bi-weekly or monthly. In some implementations, the patient health management platform 350 receives data measured from 126-variable blood tests.

The patient health management platform 350 may also receive nutrition data 320 describing food that a patient is consuming or has consumed. Via an interface (e.g., the application interface 385) presented on the patient device 380, a patient enters a record of food that they have consumed on a per meal basis and a time at which each item of food was consumed. Alternatively, the patient may enter the record for food on a daily basis. The patient health management platform 350 extracts nutrition details (e.g., macronutrient, micronutrient, and biota nutrient data) from a nutrition database (not shown) based on the food record entered by the patient. As an example, via a patient device 380, a patient may record that they consumed two bananas for breakfast at 7:30 AM. The record of the two bananas is communicated to the patient health management platform 350 and the patient health management platform 350 accesses, from a nutrition database, nutrient data including the amount of potassium in a single banana. The accessed nutrient data is returned to the patient health management platform 350 as an update to the recorded nutrition data 320. Via the same interface or one similar to the interface used to record food consumed, a patient may record and communicate medication data 325 and symptom data 330 to the patient health management platform 350. Medication data 325 describes a type of medication taken, a time at which the medication was taken, and an amount of the medication taken. In addition to nutrition data 320 and medication data 325, the patient health management platform 350 may receive descriptions of a patient's energy, mood, or general level of satisfaction with their lifestyle, treatment plan, and disease management.

Examples of biosignal data recorded and communicated to the patient health management platform 350 include, but are not limited to, those listed in Table 1. Table 1 also lists a source for recording each example of biosignal data.

TABLE 1

Example Biosignal Data and Source

| Category | Type | Signal | Source |
| --- | --- | --- | --- |
| Sensor Data | Biomarker | Weight | Body Composition Scale |
| | Biomarker | Body fat % | Body Composition Scale |
| | Biomarker | Subcutaneous fat % | Body Composition Scale |
| | Biomarker | Visceral fat % | Body Composition Scale |
| | Biomarker | Body water % | Body Composition Scale |
| | Biomarker | Muscle % | Body Composition Scale |
| | Biomarker | Bone mass | Body Composition Scale |
| | Biomarker | Basal metabolic rate | Body Composition Scale |
| | Biomarker | Protein | Body Composition Scale |
| | Biomarker | Lean body weight | Body Composition Scale |
| | Biomarker | Muscle mass | Body Composition Scale |
| | Biomarker | Metabolic age | Body Composition Scale |
| | Biomarker | Continuous Blood Glucose | Continuous Glucose Meter |
| | Biomarker | Ketones | Ketone Meter |
| | Biomarker | Systolic BP | Blood Pressure Meter |
| | Biomarker | Diastolic BP | Blood Pressure Meter |
| | Heart | Resting Heart Rate | Fitness Watch |
| | Heart | Continuous Heart Rate | Fitness Watch |
| Lab Test Data | Biomarker | Skin Temperature | Patient Investigation/Test |
| | Biomarker | Oxygen Saturation | Patient Investigation/Test |
| | Biomarker | Waist Circumference | Patient Investigation/Test |
| | Biomarker | Age | Patient Interview |
| | Biomarker | Gender | Patient Interview |
| | Biomarker | Height | Patient Interview |
| | Biomarker | BMI | Patient Interview |
| | Biomarker | HbA1c | Blood Test |
| | Biomarker | 5dg-cgm | Blood Test |
| | Biomarker | 1dg-cgm | Blood Test |
| | Biomarker | Insulin | Blood Test |
| | Biomarker | Fructosamine | Blood Test |
| | Biomarker | C-Peptide | Blood Test |
| | Biomarker | HOMA-IR | Blood Test |
| | Biomarker | 5dk | Blood Test |
| | Biomarker | Cholesterol | Blood Test |
| | Biomarker | Triglycerides | Blood Test |
| | Biomarker | HDL Cholesterol | Blood Test |
| | Biomarker | LDL Cholesterol | Blood Test |
| | Biomarker | VLDL Cholesterol | Blood Test |
| | Biomarker | Triglyceride / HDL Ratio | Blood Test |
| | Biomarker | Total Cholesterol / HDL Ratio | Blood Test |
| | Biomarker | Non-HDL Cholesterol | Blood Test |
| | Biomarker | LDL / HDL Ratio | Blood Test |
| | Biomarker | Total Iron Binding Capacity (TIBC) | Blood Test |
| | Biomarker | Serum Iron | Blood Test |
| | Biomarker | % Transferrin Saturation | Blood Test |
| | Biomarker | Amylase | Blood Test |
| | Biomarker | Lipase | Blood Test |
| | Biomarker | Ferritin | Blood Test |
| | Biomarker | Homocysteine | Blood Test |
| | Biomarker | Magnesium | Blood Test |
| | Biomarker | ALT | Blood Test |
| | Biomarker | AST | Blood Test |

TABLE 1-continued

Example Biosignal Data and Source

| Category | Type | Signal | Source |
|---|---|---|---|
| | Biomarker | ALP | Blood Test |
| | Biomarker | Total Bilirubin | Blood Test |
| | Biomarker | Direct Bilirubin | Blood Test |
| | Biomarker | Indirect Bilirubin | Blood Test |
| | Biomarker | Gamma Glutamyl Transferase (GGT) | Blood Test |
| | Biomarker | Protein | Blood Test |
| | Biomarker | Albumin | Blood Test |
| | Biomarker | A/G Ratio | Blood Test |
| | Biomarker | Globulin | Blood Test |
| | Biomarker | Urea | Blood Test |
| | Biomarker | Creatinine | Blood Test |
| | Biomarker | Uric Acid | Blood Test |
| | Biomarker | GFR | Blood Test |
| | Biomarker | Blood urea nitrogen (BUN) | Blood Test |
| | Biomarker | BUN / Creatinine Ratio | Blood Test |
| | Biomarker | Lipoprotein(a) | Blood Test |
| | Biomarker | Apolipoprotein A1 | Blood Test |
| | Biomarker | ApoB | Blood Test |
| | Biomarker | hs-CRP | Blood Test |
| | Biomarker | Apo B / Apo A1 Ratio | Blood Test |
| | Biomarker | LP-PLA2 | Blood Test |
| | Biomarker | Total Tri-iodothyronine [T3] | Blood Test |
| | Biomarker | Total Thyroxine [T4] | Blood Test |
| | Biomarker | TSH | Blood Test |
| | Biomarker | Sodium | Blood Test |
| | Biomarker | Chloride | Blood Test |
| | Biomarker | Potassium | Blood Test |
| | Biomarker | Bicarbonate | Blood Test |
| | Biomarker | Calcium | Blood Test |
| | Biomarker | Phosphorous | Blood Test |
| | Biomarker | Anion Gap | Blood Test |
| | Biomarker | Vitamin A | Blood Test |
| | Biomarker | Vitamin D2 | Blood Test |
| | Biomarker | Vitamin D3 | Blood Test |
| | Biomarker | Vitamin D Total | Blood Test |
| | Biomarker | Vitamin E | Blood Test |
| | Biomarker | Vitamin K | Blood Test |
| | Biomarker | Vitamin B1 / Thiamin | Blood Test |
| | Biomarker | Vitamin B2 / Riboflavin | Blood Test |
| | Biomarker | Vitamin B3 / Nicotinic Acid | Blood Test |
| | Biomarker | Vitamin B5 / Pantothenic Acid | Blood Test |
| | Biomarker | Vitamin B6 / Pyridoxal-5-Phosphate | Blood Test |
| | Biomarker | Vitamin B7 / Biotin | Blood Test |
| | Biomarker | Vitamin B9 / Folic Acid | Blood Test |
| | Biomarker | Vitamin B12 / Cobalamin | Blood Test |
| | Biomarker | Cortisol | Blood Test |
| | Biomarker | Cystatin C | Blood Test |
| | Biomarker | Serum Zinc | Blood Test |
| | Biomarker | Serum Copper | Blood Test |
| | Biomarker | Basophils—Absolute Count | Blood Test |
| | Biomarker | Eosinophils—Absolute Count | Blood Test |
| | Biomarker | Lymphocytes—Absolute Count | Blood Test |
| | Biomarker | Monocytes—Absolute Count | Blood Test |
| | Biomarker | Mixed—Absolute Count | Blood Test |
| | Biomarker | Neutrophils—Absolute Count | Blood Test |
| | Biomarker | Basophils | Blood Test |
| | Biomarker | Eosinophils | Blood Test |
| | Biomarker | Immature Granulocytes (Ig) | Blood Test |

TABLE 1-continued

Example Biosignal Data and Source

| Category | Type | Signal | Source |
|---|---|---|---|
| | Biomarker | Immature Granulocyte Percentage (Ig %) | Blood Test |
| | Biomarker | White Blood Cells (Leucocytes Count) | Blood Test |
| | Biomarker | Lymphocyte Percentage | Blood Test |
| | Biomarker | Mean Corpuscular Hemoglobin (Mch) | Blood Test |
| | Biomarker | Mean Corp. Hemo. Conc. (Mchc) | Blood Test |
| | Biomarker | MCV | Blood Test |
| | Biomarker | Monocytes | Blood Test |
| | Biomarker | Mean Platelet Volume (Mpv) | Blood Test |
| | Biomarker | Neutrophils | Blood Test |
| | Biomarker | Nucleated Red Blood Cells | Blood Test |
| | Biomarker | Nucleated Red Blood Cells % | Blood Test |
| | Biomarker | Plateletcrit (Pct) | Blood Test |
| | Biomarker | Hematocrit | Blood Test |
| | Biomarker | Platelet Distribution Width (Pdw-SD) | Blood Test |
| | Biomarker | Platelet To Large Cell Ratio (Plcr) | Blood Test |
| | Biomarker | Platelet Count | Blood Test |
| | Biomarker | Red Blood Cell Count | Blood Test |
| | Biomarker | Red Cell Distribution Width (Rdw-Cv) | Blood Test |
| | Biomarker | Red Cell Distribution Width-Sd (Rdw-Sd) | Blood Test |
| | Biomarker | Blood pH | Blood Test |
| | Biomarker | Hemoglobin | Blood Test |
| | Biomarker | ACCP | Blood Test |
| | Biomarker | ANA | Blood Test |
| | Biomarker | Cadmium | Blood Test |
| | Biomarker | Cobalt | Blood Test |
| | Biomarker | Chromium | Blood Test |
| | Biomarker | Caesium | Blood Test |
| | Biomarker | Mercury | Blood Test |
| | Biomarker | Manganese | Blood Test |
| | Biomarker | Molybdenum | Blood Test |
| | Biomarker | Nickel | Blood Test |
| | Biomarker | Lead | Blood Test |
| | Biomarker | Antimony | Blood Test |
| | Biomarker | Selenium | Blood Test |
| | Biomarker | Tin | Blood Test |
| | Biomarker | Strontium | Blood Test |
| | Biomarker | Thallium | Blood Test |
| | Biomarker | Uranium | Blood Test |
| | Biomarker | Vanadium | Blood Test |
| | Biomarker | Silver | Blood Test |
| | Biomarker | Aluminium | Blood Test |
| | Biomarker | Arsenic | Blood Test |
| | Biomarker | Barium | Blood Test |
| | Biomarker | Beryllium | Blood Test |
| | Biomarker | Bismuth | Blood Test |
| | Biomarker | Testosterone | Blood Test |
| Lifestyle Data | Sleep | Sleep Quality | Fitness Watch |
| | Sleep | Minutes Asleep | Fitness Watch |
| | Sleep | Minutes Awake | Fitness Watch |
| | Sleep | Minutes Light Sleep | Fitness Watch |
| | Sleep | Minutes Deep Sleep | Fitness Watch |
| | Sleep | Minutes REM Sleep | Fitness Watch |
| | Exercise | Activity Calories | Fitness Watch |
| | Exercise | Marginal Calories | Fitness Watch |
| | Exercise | BMR Calories | Fitness Watch |
| | Exercise | Total Calories Burned | Fitness Watch |
| | Exercise | Continuous Steps (per minute) | Fitness Watch |
| | Exercise | Fairly Active Minutes | Fitness Watch |
| | Exercise | Light Active Minutes | Fitness Watch |
| | Exercise | Very Active Minutes | Fitness Watch |
| | Exercise | Sedentary Minutes | Fitness Watch |
| | Exercise | Stress | Fitness Watch |

TABLE 1-continued

Example Biosignal Data and Source

| Category | Type | Signal | Source |
|---|---|---|---|
| | Patient Information | Age | Patient Interview |
| | Patient Information | Gender | Patient Interview |
| | Patient Information | Height | Patient Interview |
| | Patient Information | BMI | Patient Interview |
| | Patient Information | Vegetarian | Patient Interview |
| | Patient Information | Tobacco | Patient Interview |
| | Patient Information | Alcohol | Patient Interview |
| | Patient Information | Caffeine | Patient Interview |
| | Family Information | Father Diabetic? | Patient Interview |
| | Family Information | Mother Diabetic? | Patient Interview |
| | Family Information | Sibling Diabetic? | Patient Interview |
| | Family Information | Grandparents Diabetic? | Patient Interview |
| | Happiness | Energy | Patient Health Management App |
| | Happiness | Mood | Patient Health Management App |
| | Happiness | Cuisine Preferences | Patient Health Management App |
| | Happiness | Food Ratings | Patient Health Management App |
| | Happiness | Meal Ratings | Patient Health Management App |
| | Happiness | Exercise Preferences | Patient Health Management App |
| Symptom Data | Symptom | Headache | Patient Health Management App |
| | Symptom | Cramps | Patient Health Management App |
| | Symptom | Numbness | Patient Health Management App |
| | Symptom | Frequent Urination | Patient Health Management App |
| | Symptom | Blurred Vision | Patient Health Management App |
| | Symptom | Tiredness | Patient Health Management App |
| | Symptom | Excess hunger | Patient Health Management App |
| | Symptom | Giddiness | Patient Health Management App |
| | Symptom | Nausea | Patient Health Management App |
| | Symptom | Vomiting | Patient Health Management App |
| | Symptom | Diarrhea | Patient Health Management App |
| | Symptom | Excess thirst | Patient Health Management App |
| | Symptom | Constipation | Patient Health Management App |
| | Symptom | Erectile dysfunction | Patient Health Management App |
| | Symptom | Sleeplessness | Patient Health Management App |
| Medication Data | Medication | Diabetes Medicine | Patient Health Management App |
| | Medication | Insulin | Patient Health Management App |
| | Medication | Hypertension Medicines | Patient Health Management App |
| | Medication | Cholesterol Medicines | Patient Health Management App |
| | Medication | Obesity Medicines | Patient Health Management App |
| | Medication | Heart Medicines | Patient Health Management App |
| | Medication | Arthritis Medicines | Patient Health Management App |
| Nutrition Data | Macronutrients | Net Carb | Nutrition Database / Patient Health Management App |
| | Macronutrients | Calories consumed | Nutrition Database / Patient Health Management App |
| | Macronutrients | Net GI Carb | Nutrition Database / Patient Health Management App |
| | Macronutrients | Fiber | Nutrition Database / Patient Health Management App |
| | Macronutrients | Fat | Nutrition Database / Patient Health Management App |
| | Macronutrients | Protein | Nutrition Database / Patient Health Management App |
| | Macronutrients | Total Carb | Nutrition Database / Patient Health Management App |
| | Micronutrients | Fructose | Nutrition Database / Patient Health Management App |
| | Micronutrients | Sodium | Nutrition Database / Patient Health Management App |
| | Micronutrients | Potassium | Nutrition Database / Patient Health Management App |
| | Micronutrients | Magnesium | Nutrition Database / Patient Health Management App |

TABLE 1-continued

Example Biosignal Data and Source

| Category | Type | Signal | Source |
|---|---|---|---|
| | Micronutrients | Calcium | Nutrition Database / Patient Health Management App |
| | Micronutrients | Chromium | Nutrition Database / Patient Health Management App |
| | Micronutrients | Omega 3 | Nutrition Database / Patient Health Management App |
| | Micronutrients | Omega 6 | Nutrition Database / Patient Health Management App |
| | Micronutrients | ALA | Nutrition Database / Patient Health Management App |
| | Micronutrients | Q10 | Nutrition Database / Patient Health Management App |
| | Micronutrients | Biotin | Nutrition Database / Patient Health Management App |
| | Micronutrients | Flavonoids | Nutrition Database / Patient Health Management App |
| | Glycemic Controllers | Improve IS | Nutrition Database / Patient Health Management App |
| | Glycemic Controllers | Inhibit GNG | Nutrition Database / Patient Health Management App |
| | Glycemic Controllers | Inhibit Carb Absorption | Nutrition Database / Patient Health Management App |
| | Glycemic Controllers | Improve Insulin Secretion | Nutrition Database / Patient Health Management App |
| | Glycemic Controllers | Impr B-Cell Regen | Nutrition Database / Patient Health Management App |
| | Glycemic Controllers | Inhibit Hunger | Nutrition Database / Patient Health Management App |
| | Glycemic Controllers | Inhibit Glucose Kidney Reabsorption | Nutrition Database / Patient Health Management App |
| | Biotanutrients | *Lactococcus sp.* | Nutrition Database / Patient Health Management App |
| | Biotanutrients | *Lactobacillus sp.* | Nutrition Database / Patient Health Management App |
| | Biotanutrients | *Leuconostoc sp.* | Nutrition Database / Patient Health Management App |
| | Biotanutrients | *Streptococcus sp.* | Nutrition Database / Patient Health Management App |
| | Biotanutrients | *Bifidobacterium sp.* | Nutrition Database / Patient Health Management App |
| | Biotanutrients | *Saccharomyces sp.* | Nutrition Database / Patient Health Management App |
| | Biotanutrients | *Bacillus sp.* | Nutrition Database / Patient Health Management App |
| | Glycemic Impact | Glycemic Index | Nutrition Database / Patient Health Management App |
| | Fats | Saturated fat | Nutrition Database / Patient Health Management App |
| | Fats | Monounsaturated fat | Nutrition Database / Patient Health Management App |
| | Fats | Polyunsaturated fat | Nutrition Database / Patient Health Management App |
| | Fats | Trans fat | Nutrition Database / Patient Health Management App |
| | Fats | Cholesterol | Nutrition Database / Patient Health Management App |
| | Proteins | Histidine | Nutrition Database / Patient Health Management App |
| | Proteins | Isoleucine | Nutrition Database / Patient Health Management App |
| | Proteins | Lysine | Nutrition Database / Patient Health Management App |
| | Proteins | Methionine + Cysteine | Nutrition Database / Patient Health Management App |
| | Proteins | Phenylalanine + Tyrosine | Nutrition Database / Patient Health Management App |
| | Proteins | Tryptophan | Nutrition Database / Patient Health Management App |
| | Proteins | Threonine | Nutrition Database / Patient Health Management App |
| | Proteins | Valine | Nutrition Database / Patient Health Management App |
| | Vitamins/ Minerals | Vitamin A | Nutrition Database / Patient Health Management App |
| | Vitamins/ Minerals | Vitamin C | Nutrition Database / Patient Health Management App |

TABLE 1-continued

Example Biosignal Data and Source

| Category | Type | Signal | Source |
|---|---|---|---|
| | Vitamins/Minerals | Vitamin D | Nutrition Database / Patient Health Management App |
| | Vitamins/Minerals | Vitamin E | Nutrition Database / Patient Health Management App |
| | Vitamins/Minerals | Vitamin K | Nutrition Database / Patient Health Management App |
| | Vitamins/Minerals | B1 | Nutrition Database / Patient Health Management App |
| | Vitamins/Minerals | B12 | Nutrition Database / Patient Health Management App |
| | Vitamins/Minerals | B2 | Nutrition Database / Patient Health Management App |
| | Vitamins/Minerals | B3 | Nutrition Database / Patient Health Management App |
| | Vitamins/Minerals | B5 | Nutrition Database / Patient Health Management App |
| | Vitamins/Minerals | B6 | Nutrition Database / Patient Health Management App |
| | Vitamins/Minerals | Folate | Nutrition Database / Patient Health Management App |
| | Vitamins/Minerals | Copper | Nutrition Database / Patient Health Management App |
| | Vitamins/Minerals | Iron | Nutrition Database / Patient Health Management App |
| | Vitamins/Minerals | Zinc | Nutrition Database / Patient Health Management App |
| | Vitamins/Minerals | Manganese | Nutrition Database / Patient Health Management App |
| | Vitamins/Minerals | Phosphorus | Nutrition Database / Patient Health Management App |
| | Vitamins/Minerals | Selenium | Nutrition Database / Patient Health Management App |
| | Vitamins/Minerals | Omega 6 / omega 3 | Nutrition Database / Patient Health Management App |
| | Vitamins/Minerals | Zinc / Copper | Nutrition Database / Patient Health Management App |
| | Vitamins/Minerals | Potassium / Sodium | Nutrition Database / Patient Health Management App |
| | Vitamins/Minerals | Calcium / Magnesium | Nutrition Database / Patient Health Management App |
| | Vitamins/Minerals | PRAL Alkalinity | Nutrition Database / Patient Health Management App |
| | Metabolic Improvers | Improve BP | Nutrition Database / Patient Health Management App |
| | Metabolic Improvers | Improve Cholesterol | Nutrition Database / Patient Health Management App |
| | Metabolic Improvers | Reduce Weight | Nutrition Database / Patient Health Management App |
| | Metabolic Improvers | Improve Renal function | Nutrition Database / Patient Health Management App |
| | Metabolic Improvers | Improve Liver function | Nutrition Database / Patient Health Management App |
| | Metabolic Improvers | Improve Thyroid function | Nutrition Database / Patient Health Management App |
| | Metabolic Improvers | Improve Arthritis | Nutrition Database / Patient Health Management App |
| | Metabolic Improvers | Reduce uric acid | Nutrition Database / Patient Health Management App |
| | Food Type | Fruits | Nutrition Database / Patient Health Management App |
| | Food Type | Oils | Nutrition Database / Patient Health Management App |
| | Food Type | Spices | Nutrition Database / Patient Health Management App |
| | Food Type | Grains | Nutrition Database / Patient Health Management App |
| | Food Type | Legumes | Nutrition Database / Patient Health Management App |
| | Food Type | Nuts | Nutrition Database / Patient Health Management App |
| | Food Type | Seed Products | Nutrition Database / Patient Health Management App |
| | Cellular Stressors | Inflammatory index | Nutrition Database / Patient Health Management App |
| | Cellular Stressors | Oxidative stress index | Nutrition Database / Patient Health Management App |

TABLE 1-continued

Example Biosignal Data and Source

| Category | Type | Signal | Source |
|---|---|---|---|
| | Cellular Stressors | Gluten | Nutrition Database / Patient Health Management App |
| | Cellular Stressors | Lactose | Nutrition Database / Patient Health Management App |
| | Cellular Stressors | Alcohol | Nutrition Database / Patient Health Management App |
| | Cellular Stressors | Allergic index | Nutrition Database / Patient Health Management App |
| | Hydration | Water | Nutrition Database / Patient Health Management App |

Figure 3B:
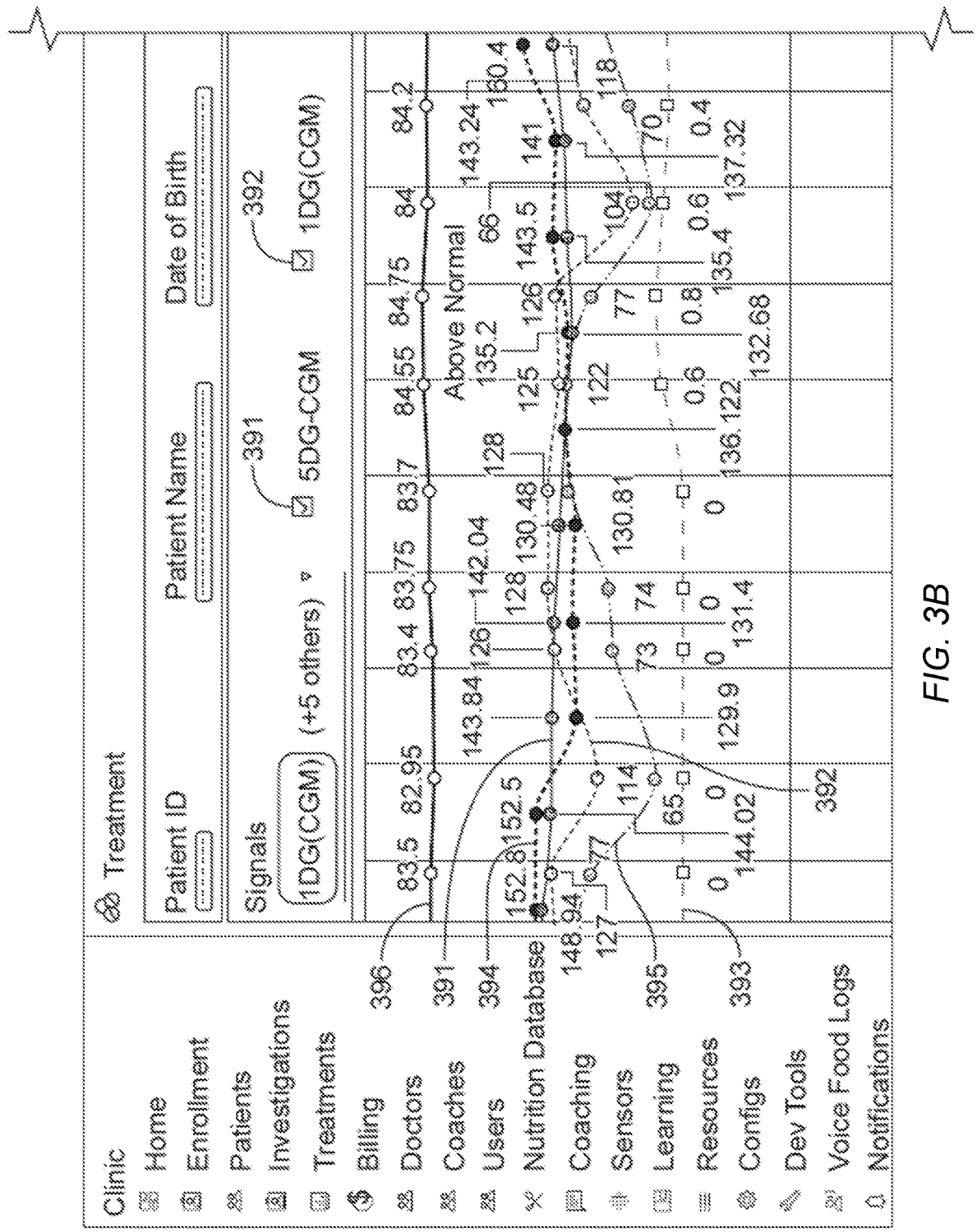
FIG. 3B is an illustration of a graphical user interface presented on a provider device to monitor a patient's metabolic progress, according to one embodiment.
Figure 3B:
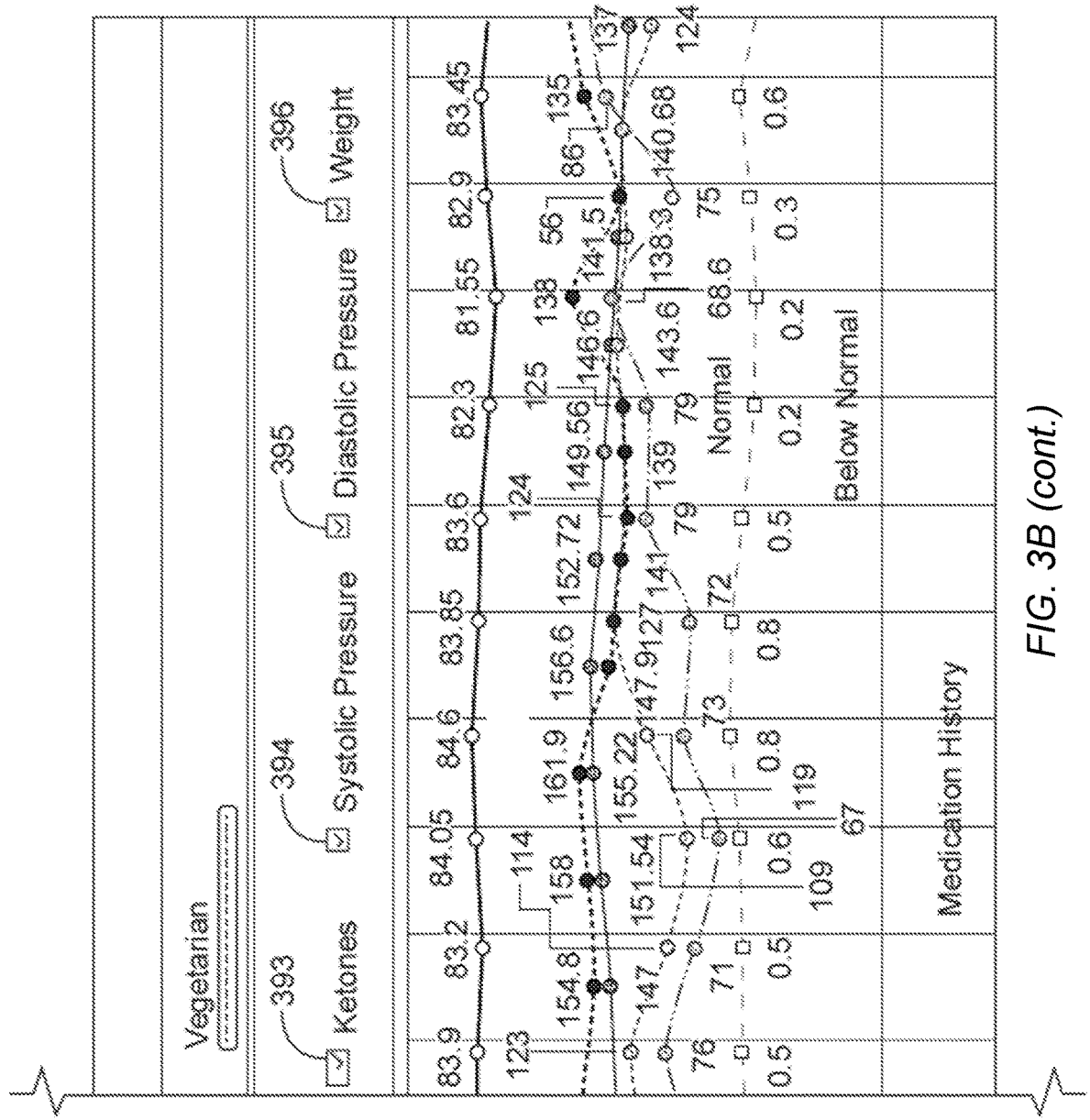

FIG. 3B is an illustration of a graphical user interface presented on a provider device for monitoring a patient's metabolic progress, according to one embodiment. The illustrated interface displays biological data recorded by wearable devices over a period of time including signal curves of 5-day average blood glucose measurements (5DG-CGM) 391, 1-day average blood glucose measurements (1DG-CGM) 392, ketones 393, systolic pressure 394, diastolic pressure 395, and weight 396. The illustrated interface in FIG. 3B displays daily changes in biological data for patient (e.g., each column displayed on the interface represents a day). Each point on the signal curve represents an average value of the signal measured on that day. For example, each point along the signal curve of 1DG-CGM 392 measurements represents a patient's 1-day average glucose for a given day. In alternate embodiments, biological data may be displayed at varying frequencies, for example bidaily, weekly, etc. To determine a daily average for each measurement, wearable sensors records several measurements of each type of wearable sensor data during that interval, in some instances at varying frequencies. For example, measurements of the 5-day average blood glucose measurements 391 and the 1-day average blood glucose measurements 392 may be recorded at the same frequencies compared to the frequency at which ketones 303 are measured or the weight 396 is recorded. Additionally, measurements of the systolic pressure 394 and diastolic pressure 395 may be recorded at the same interval, compared to the other illustrated measurements. By recording such a large volume of measurements over several periods of time for several patients, the training of machine-learned models may be performed using extensive training datasets. Additionally, given the large volume of wearable sensor data, machine learned models may provide extensive insight into a patient's metabolic health at a high level of granularity.

IV. Patient Health Management Platform

IV.A General System Architecture

Figure 4:
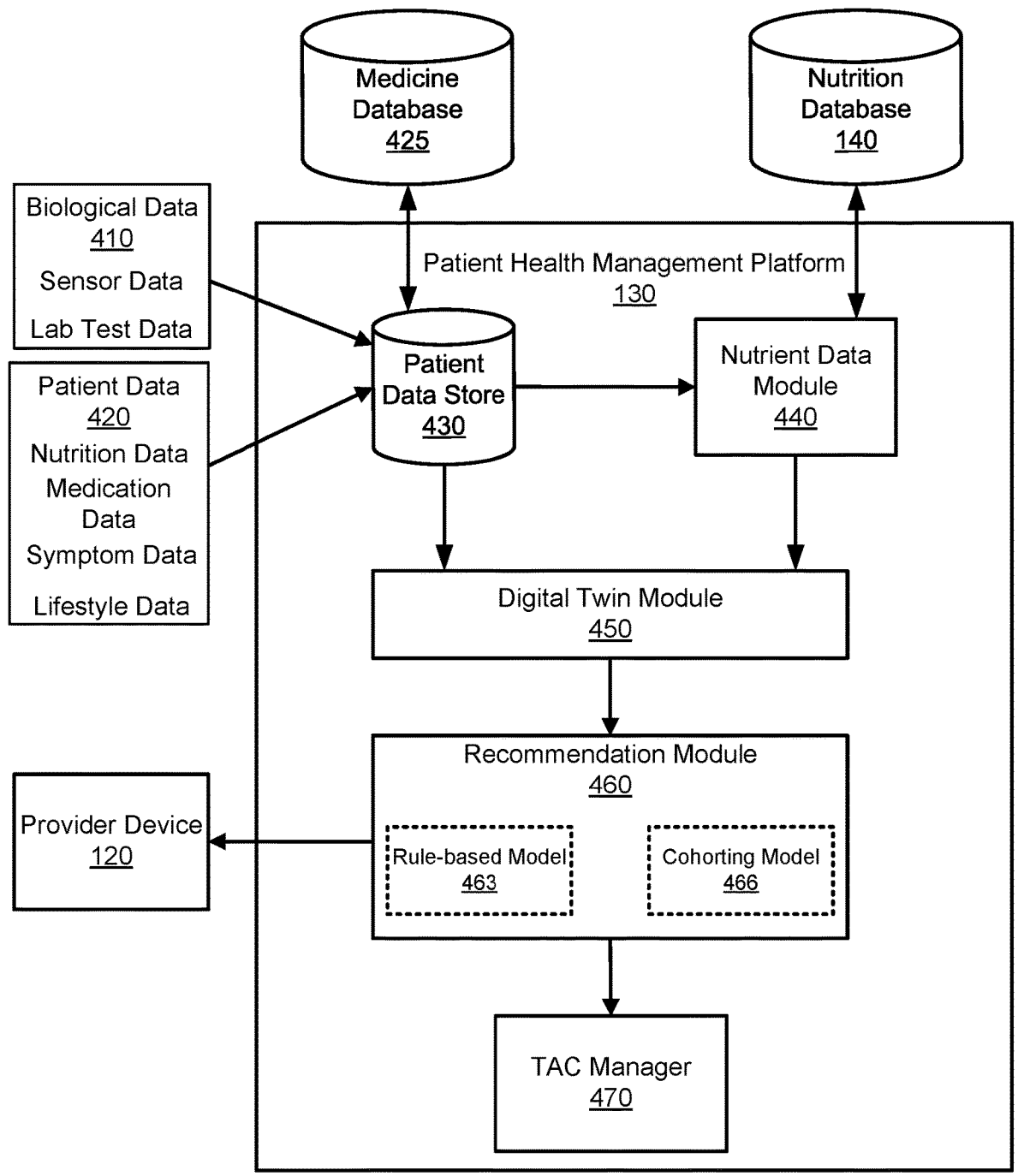
FIG. 4 is a block diagram of the system architecture of a patient health management platform, according to one embodiment.

FIG. 4 is a block diagram of the system architecture of the patient health management platform 130, according to one embodiment. The patient health management platform 130 includes a patient data store 430, a nutrient data module 440, a digital twin module 450, a recommendation module 460, and a TAC manager 470. However, in other embodiments, the patient health management platform 130 may include different and/or additional components.

The patient health management platform 130 receives biological data 410 recorded by a variety of technical sources. Biological data 410 includes sensor data (e.g. wearable sensor data 310) comprising biosignals recorded by one or more sensors worn or implemented by a patient. Such biosignals are continuously recorded and each recorded biosignal is assigned a timestamp indicating when it was recorded. Biological data 410 further includes lab test data (e.g., lab test data 315) determined based on blood draw analysis and/or other examinations that a patient has been subjected. Biosignals collected through lab test data may be recorded less frequently than biosignals collected through sensor data, for example over bi-weekly or monthly intervals. In some implementations, lab test data is determined based on procedures and analysis performed manually be doctors or researchers or based on analysis performed by machines and computers separate from the metabolic health manager 1000. The patient data store 430 stores biological data 410.

The patient health management platform 130 also receives patient data 420 that is recorded manually by a patient via an application interface on a patient device 110. Patient data 420 includes nutrition data (e.g., nutrition data 320), medication data (e.g., medication data 325), symptom data (e.g., symptom data 330), and lifestyle data. Nutrition data describes a record of foods that a patient has consumed. In some implementations, nutrition data also includes a timestamp indicating when each food was consumed by the patient and a quantity in which each food was consumed. Similarly, medication data describes a record of medications that a patient has taken and, optionally, a timestamp indicating when a patient took each medication and a quantity in which each medication was taken. In response to a patient recording medication data, the patient health management platform may access additional information from a medication database (not shown) to supplement the medication data recorded by the patient. Symptom data describes a record of symptoms experienced by a patient and a timestamp indicating when each symptom was experienced. Lifestyle data describes a record of a patient's physical activity (e.g., exercise) and a record of a patient's sleep history. Lifestyle data may also include a description or selection of emotions or feelings capturing the patient's current state of mind and body (i.e., tired, sore, energetic). In one implementation, each type of patient data 420 may be recorded instantaneously throughout the day when the patient consumes a food, takes a medication, experiences a symptom, or experiences a change in an aspect of their lifestyle. In an alternate implementation, at the end of a day, the patient health management platform 130 detects that a patient has not instantaneously recorded patient data throughout the day and prompts the patient to input a complete record of patient data for the entire day at that time. In addition to biological data 410, the patient data store 430 stores patient data 420.

In some embodiments, the patient data store 430 stores biological data 410 and patient data 430 as an ongoing recorded timeline of entries for a current time period, for example the timeline illustrated in FIG. 3B. As new patient data or biological data is recorded or as updates to existing patient data and biological data are received, the patient data store 430 updates the timeline of entries to reflect the new or updated data. Accordingly, the timeline of entries stored in the patient data store 430 comprises foods consumed by the patient at recorded times over the current time period, medications taken by the patient at recorded times over the current time period, and symptoms experienced by the patient at recorded times over the current time period. Some patient data entries may be recorded and reflected in the timeline on a daily basis, whereas other entries are recorded by a patient multiple times a day. Entries for biological data 410, for example, lab test data may be recorded even less frequently, for example as weekly updates to the ongoing timeline. The range of time between a start time and an end time for the current time period may be adjusted manually or trained over time based on predicted and true metabolic states for a patient.

The nutrient data module 440 receives nutrition data from the patient data store 440 and communicates the nutrition data to the nutrition database 140. As described above with reference to FIG. 1, the nutrition database 140 includes comprehensive nutrition information comprising macronutrient information (e.g., protein, fat, carbohydrates), micronutrient information (e.g., Vitamin A, Vitamin B, Vitamin C, sodium, magnesium), and biota nutrients (e.g. lactococcus, lactobacillus) for a wide variety of foods and ingredients. In some implementations, the nutrient data module 440 stores nutrition information in a lookup table or combination of lookup tables organized by food item or a category of food item. In other implementations, the nutrient data module 440 stores nutrition information in a lookup table organized by nutrient information or another suitable system. Based on the nutrition data received from the patient data store 430, the nutrient data module 440 identifies nutrition information associated with each food item of the nutrition data and supplements the nutrition data in the patient data store 430 with the identified nutrition information from the nutrition database 140. In some implementations, the nutrient database 140 includes over 100 food-related attributes including, but not limited to, different types of fat, protein, vitamins, and minerals.

Nutrition data supplemented by the nutrient data module 440 may be aggregated with the timeline of entries stored in the patient data store 430 to form an aggregated set of patient data for the current time period. The aggregate patient data set may additionally be stored in the patient data store 430, before being input to the digital twin module 450.

The digital twin module 450 generates a digital replica of the patient's metabolic health based on a combination of biological data 410 and patient data 420, hereafter referred to as a digital twin. The digital twin module 450 considers different aspects of a patient's health and well-being to generate and continuously update a patient's digital twin. As described herein, a digital twin is a dynamic digital representation of the metabolic function of a patient's human body. The digital twin module 450 continuously monitors biological data and patient data and correlates a patient's metabolic history with their ongoing medical history to identify changes in the patient's metabolic state. In one embodiment, the digital twin module implements two sets of trained machine-learned metabolic models: a first set of models trained to predict the patient's metabolic state given patient data as inputs and a second set of models trained to determine the patient's true metabolic state given biological data as inputs.

Based on nutrition data, medication data, symptom data, lifestyle data, and supplemental nutrition information retrieved by the nutrient data module 440, the digital twin module 450 generates a prediction of the patient's metabolic state (herein referred to as a patient's "predicted metabolic state"). The digital twin module 450 implements one or more machine-learned, metabolic models to analyze the patient data 420 recorded over a given period of time to generate a prediction of the patient's metabolic state for that period of time. Accordingly, the prediction of the patient's metabolic state is a function of a large number of metabolic factors recorded in the patient data 420 (e.g., fasting blood glucose, sleep, and exercise) and a nutrition profile (e.g., macronutrients, micronutrients, biota nutrients).

In one embodiment, the digital twin module 450 includes several machine-learned metabolic models, such that each metabolic model is trained to predict an effect of a single aspect of the patient data 420. For example, a first model may be trained to predict an impact of a patient's symptoms on their metabolic state, a second model may be trained to predict an impact of various lifestyle choices (e.g., sleep and exercise habits) on the patient's metabolic state, and a third model may be trained to predict on impact of nutrition data recorded for a period of time on the patient's metabolic state. The digital twin module 450 aggregates the output of each metabolic model to determine a holistic representation of patient's metabolic state that characterizes the combined effect of the patient's symptoms, lifestyle choices, and nutrition on their metabolic state. The digital twin module 450 and the various types of metabolic models implemented by the digital twin module 450 to generate a predicted metabolic state are further described with reference to FIG. 6.

As described herein, metabolic models used to predict a patient's biological response (e.g., a change in their metabolic state) are trained using a training data set comprised of labeled metabolic states and a record of patient data 420 that contributed to each labeled metabolic state. During the training process, the metabolic model determines the impact of an aspect patient data or (e.g., particular types of foods, medications, symptoms, or lifestyle adjustments) on a patient's metabolic state by drawing correlations and relationships between recorded patient data and each labeled metabolic state, for example the impact of given foods or medications on insulin sensitivity. Once trained, the metabolic model predicts a patient's metabolic state given an aspect of the patient data 420 as an input(s). By aggregating the output of each metabolic model, the digital twin module 450 generates a predicted change in patient's metabolic state resulting from a complete set of patient data inputs by aggregating the output of each metabolic model.

In addition to the predicted metabolic state, the digital twin module 450 may implement one or more metabolic models to generate a true representation of a patient's metabolic state (herein referred to as a "true metabolic state") based on the biological data 410 recorded for a period of time. In comparison to the metabolic models used to generate a prediction of a patient's metabolic model, the metabolic models implemented by the digital twin module 4350 to determine the true metabolic state of the patient are trained to process aspects of biological data 410 (e.g., wearable sensor data and lab test data) into an affect the patient's metabolic state. For such implementations, at the conclusion of a time period, a metabolic model may be trained to analyze biological data 410 recorded by wearable sensors during the time period and determined based on lab tests from the time period to determine a true metabolic state for the patient that reflects the actual biological conditions experienced by a patient (e.g., their HbA1c levels, or BMI) during the time period. Accordingly, given biological data 410 as an input, the metabolic model is further trained to output a patient's actual biological response (e.g., a measured insulin sensitivity or change in glucose in response to consuming a food or taking a medication).

In one embodiment, the digital twin module 450 includes several machine-learned metabolic models, such that each metabolic model is trained to predict an effect of a single aspect of the biological data 420. For example, a first model may be trained to determine a change in a patient's true metabolic state based on measurements of their HbA1c levels and a second model may be trained to determine a change in a patient's true metabolic state based on BMI measurements. The digital twin module 450 aggregates the output of each metabolic model to determine a holistic representation of the patient's true metabolic state that characterizes the combined effect of the HbA1c levels and the BMI measurements. The digital twin module 450 and the various types of metabolic models implemented by the digital twin module 450 to determine a true metabolic state are further described with reference to FIG. 7.

As described herein, metabolic models used to output a patient's true metabolic state are trained using a training data set comprised of labeled metabolic states and a record of biological data 410 that contributed to each labeled metabolic state. During the training process, a metabolic models determines an actual impact of an aspect of patient data 420 or biological data 410 (e.g., particular types of foods, medications, symptoms, or lifestyle adjustments) by drawing correlations and relationships between aspects of biological data 410 and a corresponding labeled metabolic state. Once trained, the metabolic model generates a true representation of a patient's metabolic state given an aspect of the biological data 410 as an input. By aggregating the output of each metabolic model, the digital twin module 450 determines of a true change in patient's metabolic state resulting from a complete set of biological data inputs by aggregating the output of each metabolic model.

In some embodiments, digital twin module 450 communicates both the predicted metabolic state and the true metabolic state to the timeliness, accuracy, and completeness (TAC) manager 470. The TAC manager 470 compares the predicted metabolic state and the true metabolic state to determine whether the two states are within a threshold level of similarity to each other. If the two states are within a threshold level of similarity, the manager 470 confirms the timeliness, accuracy, and completeness of the recorded patient data. As described herein, accurately recorded nutrition data, medication data, symptom data, and lifestyle data is accurate in what was recorded in the entry and when the entry was recorded.

Alternatively, if the two states are not within a threshold level of similarity, the TAC manager 470 detects that there is an error in the record of the patient data 420. Examples of such errors detected by the TAC manager 470 include, but are not limited to, an entry recorded in an incorrect amount, a failure to record an entry, or an entry recorded at the wrong time. Based on the inconsistency, or inconsistencies, between the true metabolic state and the predicted metabolic state, the TAC manager 470 identifies one or more potential errors in the recorded patient data which may have contributed to the one or more inconsistencies and generates notifications to the patient device 380 for presentation to the patient. In some implementations, the patient health management platform 130 compares timeliness, accuracy, and completeness evaluations against different thresholds. If at least one of the three evaluations does not satisfy the compared threshold, the platform 130 generates and communicates a notification to a patient or a medical provider. The notifications may prompt a patient to confirm that each entry flagged as having a potential error is correct. If the entry is not correct, the user may revise the entry to correct the error. If the user corrects the error, the revised patient data 420 is input to the digital twin module 450 to generate an updated predicted metabolic state which is then compared to the true metabolic state by the TAC manager 470.

Because the patient health management platform generates a predicted metabolic state for a patient based on a different set of inputs than the true metabolic state (e.g., patient data vs. biological data), the patient health management platform 350 can compare the true state and the predicted state. Discrepancies between the two states reflect inaccuracies in the predicted metabolic state, which likely result from incorrectly recorded patient data. For example, if a patient drank coffee at 3 PM, but did not record the coffee or underreported the amount of coffee, the predicted metabolic state will differ from the true metabolic state. Accordingly, the platform 130 may evaluate the correctness of patient data recorded by the patient and provide feedback to help the patient better manage their metabolic health.

As described above with reference to FIG. 3A, patient data and biological data may be recorded at varying intervals. For example, sensor data is recorded continuously every 15 minutes, lab test data is recorded bi-weekly, and patient data 420 is recorded multiple times a day as needed. Therefore, the patient health management platform 130 may not receive an updated recording for every type of data in time to generate a predicted metabolic state. When generating a predicted metabolic state for a particular period of time, the digital twin module 450 retrieves all patient data 420 recorded within that period of time and the metabolic state predicted by the during the preceding period of time. In some embodiments, the digital twin module 450 implements one or more machine learning models to process, as inputs, the recorded patient data and the most recently predicted metabolic state into a predicted metabolic state for a current time period. In place of the most recent predicted metabolic state, the digital twin module 450 may input the most recent true metabolic state to the one or more machine learning models. Accordingly, the predicted metabolic state reflects any effects that the most recently recorded patient data 420 had on a previous metabolic state.

Similarly, when generating a true metabolic state for a period of time, the digital twin module 450 retrieves all biological data 410 recorded within that period of time (e.g., heart rate, exercise, continuous blood glucose, ketones, blood pressure, weight) and the true metabolic state generated during the preceding period of time. The digital twin module 450 may also rely on one or more machine learning models to process the retrieved biological data 410 and the most recent true metabolic state into a current true metabolic state. Accordingly, the generated true metabolic state also reflects any effects of the most recently recorded biological data 410 had on a previous metabolic state. For example, a machine learned model may use a continuous blood glucose signal measured every 15 minutes to calculate a patient's 5-day average blood glucose. The computed measurement is compared against established ranges in the medical literature to determine whether the patients are in a diabetic, prediabetic, or non-diabetic state as they progress with their treatment. In common implementations, the digital twin module 450 updates a patient's metabolic state at a higher frequency than a frequency at which lab test data is recorded. As such, when lab test data is unavailable for the current period of time, the digital twin module 450 may generate the updated metabolic state based on the lab test data recorded most recently for a preceding period of time.

The digital twin module 450 communicates the predicted metabolic state and/or the true metabolic state to the recommendation module 460. In one embodiment, the recommendation module 460 compares a patient's predicted metabolic state to baseline metabolic state for a patient with a functional metabolism. For patients who already have a functional metabolism, the recommendation module 460 compares the predicted metabolic state to a baseline metabolic state for a patient with an optimal metabolism. In either implementation, the recommendation module 460 determines discrepancies between the patient-specific predicted metabolic state and the baseline metabolic state and identifies one or more biosignals which could be adjusted such that the predicted state becomes more similar to the baseline state, for example lower blood glucose levels in the predicted metabolic state or an imbalance between certain micronutrients and micronutrients.

In an alternate embodiment, the recommendation module 460 receives the true metabolic state determined by digital twin module 450 and compares the true metabolic state to a baseline metabolic state to identify one or more biosignals which could be adjusted such that the true metabolic state becomes more similar to the baseline metabolic state. Although the techniques are described herein with reference to a comparison of the predicted metabolic state to a baseline metabolic state, a person having ordinary skill in the art would recognize that those techniques could also be applied based on a comparison of the true metabolic state to the baseline metabolic state.

Based on the determined adjustments, the recommendation module 460 generates a recommendation for improving the patient's biosignals to more closely resemble those of the baseline metabolic state. The recommendation includes a set of objectives for a patient to complete to improve the patient's metabolic health. The set of objectives include a medication regimen or schedule, a food or meal schedule, micronutrient and biota nutrient supplements, one or more lifestyle adjustments, or a combination thereof. The medication regimen, food schedule, and supplement schedule may prescribe medications, food items, or supplements which may either replenish nutrients in which a patient is deficient, offset the effects of nutrients for which a patient has an excess, or a combination thereof. The medication regimen, food schedule, and supplement schedule may also alleviate or mitigate the symptoms (as indicated by symptom data recorded by a patient) that a patient is experiencing by addressing the biological root cause of the symptoms. One example of a medication regimen may include a recommended medication or combination of medications and an adherence schedule for each medication. One example of a food schedule may include a recommended food item or, more broadly, a category of food item and an amount of the food item to be consumed. Similarly, a lifestyle adjustment may prescribe particular lifestyle adjustments for addressing a patient's symptoms or nutrient abnormalities. Examples of lifestyle adjustments include, but are not limited to, increasing physical activity or increasing a patient's amount of sleep. In some implementations, the content of lifestyle adjustments may broadly overlap with food or medication adjustments. For example, a lifestyle adjustment may recommend a patient replace refined carbohydrates with wholegrain foods, while the food schedule includes a set of particular wholegrain foods.

The recommendation module 460 may apply several data processing techniques to interpret the data from a patient's metabolic state when generating a patient-specific recommendation. In one implementation, the recommendation module 460 applies a rule-based model 463, which generates at least a portion of the recommendation based on medical practices that are known to be consistently effective. The rule-based model 463 accesses and applies one or more rules defined by experts that codify and automate a physician's medical knowledge. For example, if a patient has bloodwork showing hemoglobin A1c (HbA1C) within a certain range $A1$ and has a body mass index (BMI) within a certain range $B1$, prescribe Medicine A at a certain dosage to the patient. However, if another patient has HbalC in a different range $A2$ and BMI in a different range $B2$, then prescribe a combination of Medicines B and C at certain dosages to that patient. Additionally, the recommendation module 460 may implement a cohorting model 466 to assign patients with similar metabolic states or, more generally, similar metabolic health to the same cohort and then generate a treatment that is tailored for a specific cohort. In some implementations, the recommendation module 460 includes a personalized nutrition engine configured to generate the personalized layer of the nutrition database 140 as described above.

For example, in a phenomenon known as the Dawn effect, a significant number of patients suffering from diabetes are affected by an abnormal increase in blood glucose in the early morning hours while they are asleep. To inhibit the Dawn effect, a patient-specific recommendation may instruct a patient to consume a nutrient-rich food item or quantity of food item, for example a spoonful of medium-chain triglyceride (MCT)-rich coconut oil, known to contain nutrients that inhibit the Dawn effect. Upon doing so, the patient's metabolism will metabolize the consumed nutrient in time to allow the metabolized ketones to counteract the Dawn Effect. Biological interactions including the Dawn effect may be identified or determined based on an analysis of a patient's metabolic history (e.g., the progress tracker illustrated in FIG. 3B). Accordingly, the recommendation module 460 may generate a recommendation prescribing one of any number of nutrients to inhibit one of any number of metabolic interactions. In such implementations, the recommendation module 460 relies on analysis of a population of patients to initially identify such metabolic interactions, and then relies on patient-level data to personalize the identification of such interactions, for example by narrowing the list to only relevant metabolic interactions. Additionally, the TAC manager 470 may determine, based on a patient's metabolic progress, whether that patient has overcome a detrimental metabolic interaction and accordingly may update the dataset used to train the recommendation module 460 to recognize the combination of nutrients that overcame the interaction.

In some implementations, the recommendation module 460 generates multiple candidate recommendations and communicates each candidate recommendation to digital twin module 450. Each candidate recommendation prescribes a different possible intervention (e.g., adjustments or changes in a patient's nutrition, exercise, and sleep habits). For each candidate recommendation, the digital twin module 450 predicts a patient's metabolic response that would result from adherence to the candidate recommendation. Based on the predicted response, the recommendation module 460 compares multiple candidate recommendations to confirm which candidate recommendations will have the most positive effects on the patient's metabolic health. The digital twin module 450 uses a combination of metabolic models to predict a future metabolic state of a that would result if the patient adhered to the recommendation.

After generating the patient-specific recommendation, the recommendation module 460 communicates the recommendation to a health care provider device 120 to be reviewed by a doctor or a coach. Via a review application (e.g., the doctor review application 365) the doctor, or another trained professional, may review the treatment recommendation to identify any errors or potential risks in the generated recommendation. Optimally, the adherence of the recommendation module 460 to a set of medical rules applied by the rule-based model 463 generates a recommendation including a combination of medications, nutrient sources, and lifestyle adjustments that would be most beneficial to the patient. However, in some cases, the doctor may be aware of certain knowledge that has not been captured in the system yet. For example, the patient may not have responded well to a given medication in the past. Via the doctor review application 365, a doctor may manually identify such an exception and report that exception back to the recommendation module 460. In addition to identifying the exception, the doctor may also return a corrected recommendation to the recommendation module 460. The recommendation module 460 may dynamically re-train the rule-based model 463 using the new knowledge to prevent the same error from being made in future recommendations. Alternatively, the recommendation module 460 generates an alternative recommendation based on the exception identified by the doctor and returns the revised recommendation to the provider device 120 for further review.

As another example, a patient may have failed to record an allergy to a medication, a food, or both with the patient health management platform 130 and the recommendation module 460 may generate a recommendation including a medication or food to which the patient is allergic. Via the doctor review application 365, the doctor may identify the patient's missed allergy and return that allergy to the recommendation module 460. The patient response module 460 communicates the updated allergy to the patient data store 430 and the recommendation module 460 generates a revised recommendation based on the updated allergy. Additionally, after communicating an allergy to the patient data store, future recommendations generated by the recommendation module 460 will account for that allergy.

Similar to the description above regarding the doctor (or trained professional) and the doctor review application 365, a coach may review the nutrition and lifestyle recommendation for accuracy, efficacy, and feasibility. For example, if a coach recognizes that a recommendation includes a lifestyle or nutrition recommendation that would be unreasonable to expect a patient to follow, the coach may return that feedback to the recommendation module 460. As another example, if a coach recognizes that a recommendation includes lifestyle or nutrition recommendation that would not be effective even if a patient did follow the recommendation, the coach may return that feedback to the recommendation module 460. Based on the coach's feedback, the recommendation module 460 may generate an updated recommendation and re-train the rule-based model 463 such that future recommendations reflect the coach's feedback.

Upon receiving approval of the generated recommendation from both a doctor (regarding the nutrition recommendation, medication recommendation, and symptom recommendation) and a coach (regarding the lifestyle recommendation and nutrition recommendation), the recommendation module 460 communicates the recommendation to the TAC manager 470 and a patient device 110 for a presentation to a patient. As a patient records nutrition data, medication data, and lifestyle data via an application interface (e.g., the patient health management application 385), the TAC manager 470 compares the recorded data to what was prescribed in the recommendation. As the patient records patient data following the receipt of a recommendation at the patient device, the TAC manager 470 compares the recorded patient data with the list of objectives included in the recommendation to determine which objectives the patient has completed. In some implementations, the TAC manager 470 records a patient's progress in completing the recommended objectives, for example based on a completion score representing a number of completed objectives versus a number of uncompleted objectives.

In situations in which a patient does not complete all of the recommended objectives within a threshold amount of a time (for example, prior to the receipt of a recommendation based on a predicted metabolic state for a subsequent period of time), the TAC manager 470 may send a reminder to the patient to complete the remaining objectives. Alternatively, the TAC manager 470 may include any uncompleted objectives in a subsequent recommendation generated by the recommendation module 460.

In addition to tracking a patient's progress through a series of recommendations, which may also be understood as a series of metabolic states, the TAC manager 470 may track a patient's progress based on biological data 410 recorded continuously by sensor data supplemented with lab test data. For example, wearable sensors record biosignals in 15 minute intervals. Accordingly, the TAC manager 470 generates a representation of changes in measured biosignals, for example as points plotted on a timeline. As an example, a wearable sensor records initial biosignals indicating a patient's blood glucose levels to be below a threshold level associated with a functional metabolism. In response, the patient receives a recommendation generated by the recommendation module 460 and eats a meal of recommended food items and takes a recommended medication. Biosignals recorded afterwards measure a patient's blood glucose levels to have reached the functional metabolism threshold. In response, the patient receives another recommendation outlining objectives for further improving the patient's metabolism to achieve an optimal metabolism or a functional metabolism. Again, the patient eats a meal of recommended food items and takes a recommended medication. Biosignals recorded afterwards measure a patient's blood glucose levels to have passed the functional metabolism threshold. The above process is repeated continuously as a patient continues to receive recommendations and improve their metabolic health. As a result, the TAC manager 470 is able to model a patient's continuous improvement in their metabolic health while they use the patient health management platform 130.

Figure 5:
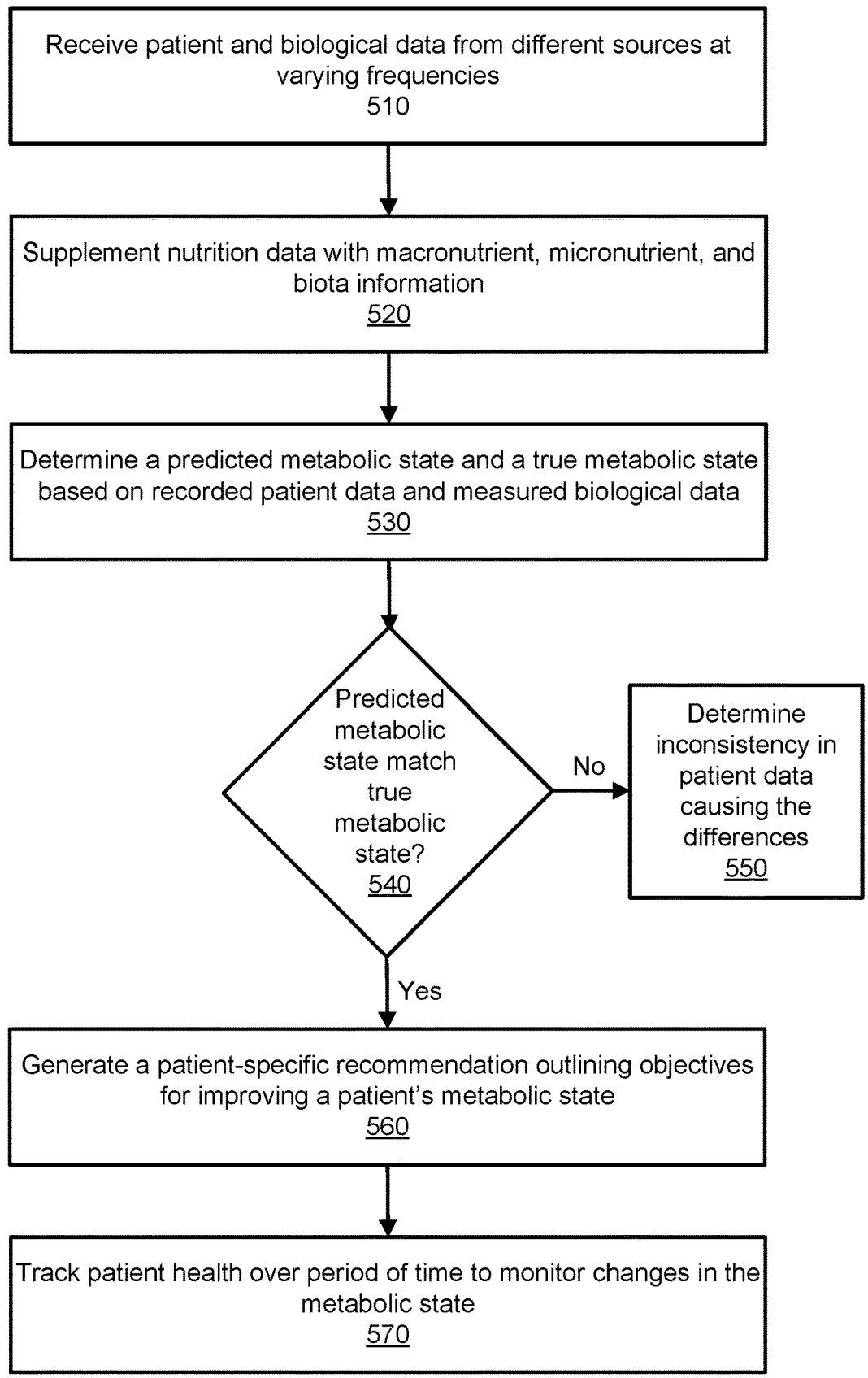
FIG. 5 is a flowchart illustrating a process for generating a patient-specific recommendation for improving metabolic health of a patient, according to one embodiment.

FIG. 5 is a flowchart illustrating a process for generating a patient-specific recommendation for improving metabolic health of a patient, according to one embodiment. The patient health management platform 130 receives 510 patient data and biological data from different sources at varying frequencies. Patient data describes data manually recorded by a patient and communicated to the platform 130. Biological data describes data manually recorded by wearable sensors or measured based on lab tests before being communicated to the platform 130.

Patient data includes nutrient data which is recorded by the patients as a list of foods which have been consumed by the patient over a period of time. While the impact of a food item by itself on a patient's metabolic state may not be known, the impact of particular macronutrients, micronutrients, and biota nutrients associated with the food item on a patient's metabolic state is known. As a result, the patient health management platform 130 accesses a nutrition database 140 storing such macronutrient, micronutrient, and biota nutrient information. Based on the accessed information, the platform 130 supplements 520 the recorded nutrition data with the accessed macronutrient, micronutrient, and biota information.

Consistent with the description above in Section IV.A, the platform 130 determines 530 a predicted metabolic state based on the recorded patient data (e.g., patient data 420) and the patient's true metabolic state based on the measured biological data (e.g., biological data 410). The platform 130 compares 540 the predicted metabolic state with the true metabolic state to determine whether the two states match, or are within a threshold level of similarity. If the two metabolic states are not within the threshold level of similarity, the platform 130 determines 550 one or more inconsistencies in the patient's recording of their patient data, which may have caused the predicted metabolic state to differ from the true metabolic state. The platform 130 communicates the inconsistency back to a patient device (i.e., patient device 110). Upon receiving the inconsistency, the patient device 110 presents a user interface notifying the patient of the inconsistency and enabling the patient to correct the inconsistency. The platform 130 receives 555 the updated patient data and determines 530 an updated predicted metabolic state based on the updated patient data.

If the two metabolic states are within a threshold level of similarity, the platform 130 categorizes the predicted metabolic state as representative of poor metabolic health, functional metabolic health, or optimal metabolic health. Based on the assigned category, the platform 130 generates 560 a patient-specific recommendation outlining objectives for improving the patient's metabolic state. In particular, the recommendation may outline objectives for consuming food, taking medication, or engaging in lifestyle adjustments to supplement nutrients in which a patient is deficient and that may have contributed to the patient's deteriorated metabolic state.

Following the receipt of the recommendation, a patient continues to record patient data and wearable sensors continue to record biological data, both of which are representative of a metabolic state for a subsequent period of time. As patient data and biological data continue to be recorded, the patient health management platform 130 tracks 570 patient health over a period of time to monitor changes in the patient's metabolic state. Based on the monitored changes, the platform 130 is able to confirm whether or not a patient is adhering to the recommendation generated by the platform 130. If the patient is not adhering to the recommendation, the platform 130 may generate a notification or reminder to the patient, a doctor assigned to the patient, a coach assigned to the patient, or a combination thereof. If that patient adheres to the recommendation, the platform 130 is able to review the changes in metabolism to confirm that the recommendation is improving the patient's metabolic health. If the platform is not improving the patient's metabolic health, the platform 130 is able to dynamically revise the recommendation to correct the deficiencies of the initial recommendation. If the platform is improving the patient's metabolic health, the platform 130 is able to dynamically update the recommendation to continue to optimize the patient's metabolic health in view of their improved metabolic state.

IV.B Nutrition Database

In some implementations, nutrition information for food items included in the nutrition data received from the patient data store 430 may not be found in the nutrition database 140. In such instances, the nutrition database 140 may return nutrition information for a similar or comparable food item. The nutrition database 140 may additionally notify a human operator that the nutrition database 140 should be updated to include nutrition information for the unknown food item. A human operator may subsequently update the nutrition database 140 with nutrition information for the unknown food item. To identify comparable or similar food items, individual food items may be assigned similarity scores to other food items based on comparisons of their nutrition information such that food items with similar nutrition information are assigned higher similarity scores. Alternatively, food items may be categorized into food groups or clustered based on similarities in their nutrition information.

When the nutrient data module 440 receives a food item that is not included in the nutrition database 140, the nutrient data module 440 may perform a semantic analysis (e.g., N-gram analysis) to identify sub-terms within the recorded text of the food item and compare those sub-terms to food items stored in the nutrition database 140. Based on the comparison of sub-terms, the nutrient data module 440 may identify a similar food item and retrieve the nutrition information associated with that food item. For example, the nutrient data module 440 receives a food item recorded as "rye bread," but the nutrition database 140 does not include nutrition information for "rye bread." The nutrient data module 440 may identify sub-terms "rye" and "bread" and retrieve nutrition information related to "rye" food items, "bread" food items, or a combination thereof.

In some implementations, a nutrient data module 440 generates a personalized nutrition layer that establishes a patient-specific rating of foods based on a specific nutritional impact of each food on that patient along with their food preferences, allergies and dietary restrictions. In the personalized nutrition layer of the nutrient data module 440, multiple per-patient ratings are assigned to individual food items including, but not limited to, a preference rating (e.g., how appealing the food is to the patient) and a health rating determined based on the personalized impact of that food on multiple aspects of the patient's metabolic health (e.g., blood glucose and blood pressure). In addition, the personalized nutrition layer updates the per-patient health rating for each food as the patient's metabolic health changes over time. Similarly, foods that a patient is allergic to or a patient rarely consumes may be flagged in the personalization layer. If a patient records a food that has not been previously consumed or records a food that includes an ingredient to which they are allergic, the nutrient data module 440 may flag the food item and generate a notification requesting that the patient confirm that the food was accurately recorded.

Food items in the personalized nutrition layer may be categorically organized based on their particular impact on a patient's metabolism. In one implementation, food items are color coded, for example a red label indicating that a food item negatively impacts a patient's metabolism, a yellow label indicating that a food item has no or a marginal impact on a patient's metabolism, and a green label indicating that a food item has a positive impact on the patient's metabolism. Described differently, a green classification may be assigned to food items which are recommended to a patient, a yellow classification may be assigned to food items which are recommended to a patient in moderation, and a red classification may be assigned to food items which are to be avoided by a patient.

The label assigned to each food item in the personalization layer may be determined using machine learning techniques, rule-based techniques, or a combination thereof. Rule-based techniques may be used to categorize food items based on their average impact on the general patient population or based on empirically proven knowledge. For example, a patient consumes a banana high in potassium, which is empirically proven to contribute to an improved metabolic state for most patients. Accordingly, the banana is assigned a green color label.

Machine-learning techniques may be implemented to refine the labels by analyzing the changes in patient metabolism (i.e., recorded via wearable sensors or lab tests) with particular food items (i.e., recorded as patient data) that may have contributed to those changes. Such analyses are performed using a large data set of patients and foods to identify specific cohorts of patients that would benefit from a particular food. For example, the analysis may show that based on their metabolic profile, some patients do not benefit from eating more bananas ("Cohort A"), whereas other patients do ("Cohort B"). Machine learning models pinpoint the metabolic factors that distinguish Cohort A and Cohort B (for example, mineral deficiencies or high levels of blood pressure), allowing the system to personalize the labels and associate banana with a green label ("beneficial") for patients in Cohort B but a yellow label ("neutral") for patients in Cohort A.

Over time, as a patient adheres to their patient-specific recommendations, the patient's metabolism will improve. As their metabolism improves, certain food items that were previously assigned personalized red labels, or other labels identifying food items with negative impacts, may be re-categorized with different personalized labels. For example, a food item previously assigned a red label may be reassigned a yellow label identifying the food item as now having no impact on metabolism. The personalized nutrition layer may also assign quantities to each food item label indicating that consuming the food item in too high a quantity may negatively impact a patient's metabolism, but consuming the food item within a certain quantity may have no negative impact on the patient's metabolism. Similarly, over time, the range assigned to each food item may be dynamically updated based on a patient's improved metabolic state.

Additionally, the personalized nutrition layer may additionally include a written description indicating why a food item has been categorized with a particular label. Such a written description may be accessed by a patient or presented to a patient via the TAC manager 470 to further inform the patient.

IV.C Metabolic Digital Twin

Figure 6:
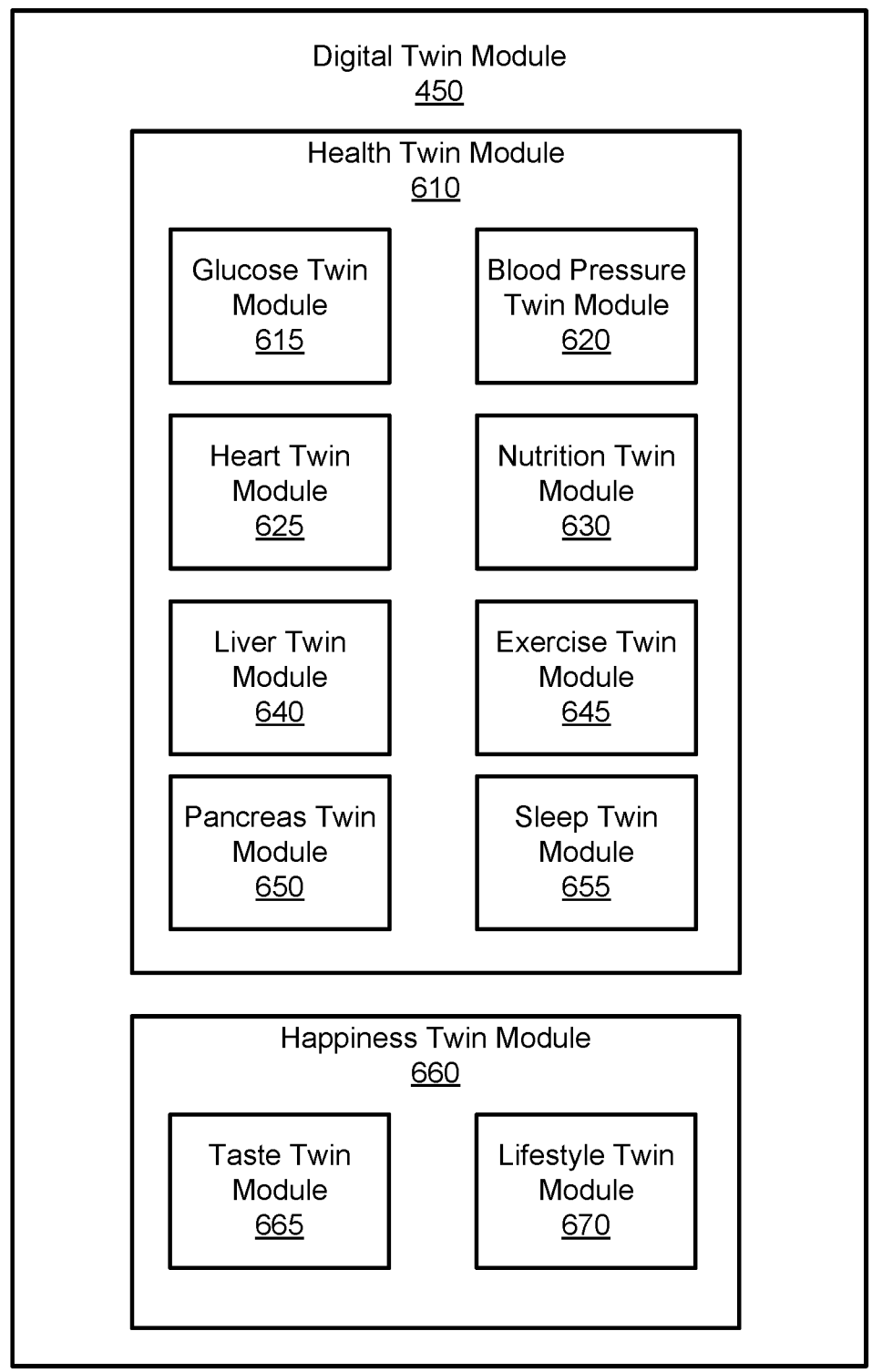
FIG. 6 is a block diagram of the system architecture of a digital twin module, according to one embodiment.

As described above, the digital twin module 450 generates a digital twin of the patient's metabolic health to continuously monitor and update different aspects of a patient's health and well-being. FIG. 6 is a block diagram of the system architecture of a digital twin module 450, according to one embodiment. The digital twin module 450 includes a health twin module 610 and a happiness twin module 660. The digital twin module 450 may include different and/or additional components to perform the same functions described with regards to the digital twin module 450. The digital twin module 450 generates a digital replica of a patient's metabolic state in two dimensions: a health dimension and a happiness dimension.

The health twin module 610 generates a digital replica of the health dimension of a metabolic state based on biological measurements recorded by wearable sensors and lab test data. In the embodiment illustrated in FIG. 6, the health twin module 610 comprises a glucose twin module 615, a blood pressure twin module 620, a heart twin module 625, a nutrition twin module 630, a liver twin module 640, an exercise twin module 645, a pancreas twin module 650, and a sleep twin module 655. Each component of the health twin module 610 captures and updates a critical aspect of a patient's metabolic health such that the digital twin represents the patient's overall metabolic health. The health twin module 610 may include additional, fewer, or a different combination of components to generate a digital twin based on varying aspects of a patient's metabolic health. In some embodiments, each component of the health twin module 610 generates an output indicating a condition of an aspect of the patient's metabolic health. For example, the heart twin module 625 may generate an output indicating the patient's heart health rating on a scale of 100, for example 85. This is derived from cardiac health biomarkers such as Lipoprotein(a), Apolipoprotein B, and High-Sensitivity C-Reactive Protein (HS-CRP).

The glucose twin module 615 tracks and analyzes glucose dynamics for a patient over time to enable the digital twin to model glucose dynamics for the patient. The glucose twin module 615 may analyze glucose dynamics recorded via a wearable sensor. The heart twin module 625, liver twin module 640, and the pancreas twin module 850 track and analyze function and physiology of a patient's heart, liver, and pancreas to enable the digital twin to model heart, liver, and pancreas function for the patient. The heart twin module 625, the liver twin module 640, and the pancreas twin module 650 may analyze function of a patient's heart, liver, and pancreas based on information recorded via one or more lab tests. The blood pressure twin module 620 tracks and analyzes blood pressure dynamics for a patient over time to enable the digital twin to model blood pressure dynamics for the patient. The blood pressure twin module 615 may analyze blood pressure dynamics recorded via a wearable sensor or via lab test data.

The nutrition twin module 630 communicates with the nutrient data module 640 to track and analyze nutrition information of food consumed by a patient to enable the digital twin to model the impact of food consumed by the patient. The nutrition twin module 630 may analyze a combination of macronutrient parameters, micronutrient parameters, and biota nutrients for each food item recorded by the patient through a patient device 380. The exercise twin module 645 tracks exercise activity for a patient and analyzes those exercise habits by correlating periods of exercise (or inactivity) with changes in the patient's metabolic state. The exercise twin module 645 may analyze exercise activity recorded by the patient through a patient device 380. Similarly, the sleep twin module 655 tracks sleep trends for a patient and analyzes those sleep trends by correlating quality, length, and frequency of sleep with changes in the patient's metabolic state. The sleep twin module 655 may analyze sleep trends recorded by the patient through a patient device 380 or by a wearable sensor.

Each module (or component) of the health twin module 610 is connected to and communicates with other modules of the health twin module 610 to capture the complex interaction effects that contribute to a patient's metabolic state. For example, blood pressure dynamics are driven by a combination of factors including blood glucose dynamics, heart function, nutrition, exercise, and sleep trends. Each of those driving factors are, in turn, driven by other factors represented in the patient's digital twin.

The happiness twin module 660 generates a digital replica of the happiness dimension of a patient's metabolic state based on feedback recorded through a patient device 380. In the embodiment illustrated in FIG. 6, the happiness twin module 660 comprises a taste twin module 665 and a lifestyle twin module 670. Each component of the happiness twin module 660 captures a critical aspect of a patient's satisfaction with their recommended treatment to their digital twin such that the digital twin also represents the patient's overall experience with treatment. The happiness twin module 620 may include additional, fewer, or a different combination of components to generate a digital twin based on varying aspects of a patient's metabolic health. In some embodiments, each of the taste twin module 660 and the lifestyle twin module 665 generate an output indicating a patient's current state of mind regarding a food item, meal recommendation, or a lifestyle recommendation prescribed by a patient-specific recommendation. For example, each food consumed by a patient may be labeled with a score on a 5-star scale, such as "4 stars".

The taste twin module 660 communicates with the nutrition twin module 630 to assign a preference to each food item recorded by the patient (e.g., a label indicating whether the patient enjoyed the food item or not). In conjunction, the nutrition twin module 630 and the taste twin module 660 may compare two foods with a similar metabolic effect and prioritize whichever food the patient enjoyed more. The food item that the patient enjoyed more will be carried forward in other future patient-specific recommendations. The lifestyle twin module 660 communicates with the exercise twin module 645 and the sleep twin module 655 to assign a preference to the activities recorded by the patient. For example, if a patient wishes to engage in more exercise, future treatment recommendations may be generated with an emphasis on more frequent exercise.

As described herein, each module of the health twin module 610 and the happiness twin module 660 includes a uniquely trained metabolic model. In particular, when generating a prediction of a patient's metabolic state, each involved metabolic model is trained to determine an impact of a particular type of patient data input on a patient's metabolic state. When generating a prediction of a patient's metabolic state, the digital twin module 450 may consider the output of the metabolic models trained to receive patient data as inputs, for example the nutrition twin module 630, the exercise twin module 645, the sleep twin module 655, and the lifestyle twin module 670. For example, the nutrition twin module 630 implements a metabolic model to predict a patient's metabolic state based on patient data identifying food items consumed by the patient. As additional examples, each of exercise twin module 645, the sleep twin module 655, and the lifestyle twin module 670 implement a metabolic model to predict a patient's metabolic state based on patient data describing the patient's exercise habits, sleep habits, and lifestyle habits, respectively. The digital twin module 450 may also consider metabolic models that are not illustrated in FIG. 6, or the other twin modules that are illustrated in FIG. 6 when generating a prediction of a patient's metabolic state.

In comparison, each metabolic model involved in determining a patient's true metabolic state is trained to determine an impact of a particular type of biosignal input on a patient's metabolic state, for example the glucose twin module 615, the blood pressure twin module 620, the heart twin module 625, the liver twin module 640, and the pancreas twin module 650. For example, the glucose twin module 615 implements a metabolic model to evaluate a patient's true metabolic state based on input biosignals describing the glucose dynamics of the patient. As additional examples, each of the heart twin module 625, the liver twin module 640, and the pancreas twin module 650 implement metabolic models to evaluate, respectively, a true performance of a patient's heart, liver, and pancreas based on input biosignals describing the functionality of those organs. As yet another example, the blood pressure twin module 620 implements a metabolic model to evaluate a patient's true metabolic state based on input biosignals describing blood pressure dynamics of the patient. The digital twin module 450 may also consider metabolic models that are not illustrated in FIG. 6, or the other twin modules that are illustrated in FIG. 6 when generating a prediction of a patient's metabolic state.

In some embodiments, modules of the digital twin module 450 may implement a combination of multiple machine-learned models to more accurately and completely characterize each aspect of a patient's metabolic health. For example, as will be described below in Section IV.D, the glucose twin module 615 may implement both a glucose impact model (as described in Section IV.D.1) and a 1-Day Average Glucose model (as described in Section IV.D.2).

After a digital twin of a patient has been initialized, components of the digital twin module 450 continuously collect data describing changes in conditions contributing to the patient's metabolic health. When any component of the digital twin module 450 receives updated data, the digital twin module 450 updates a digital twin of the patient in near real-time to reflect the updated data.

IV.D Machine-Learned Metabolic Models

Because the human body is a complex system and different patients may respond differently to the same input stimuli, the patient health management platform 130 includes mathematical models trained to learn the relationships between response signals representing a patient's metabolic states and input stimuli causing those responses. As described above, the patient health management platform 130 applies machine-learning based artificial intelligence to generate a precision treatment recommendation for improving a patient's metabolic health by predicting their response to future input stimuli. The digital twin module 450 implements a combination of machine-learned models that are trained to predict a response of the human body based on each patient's current metabolic state and a set of inputs (e.g., recorded patient data, sensor data, and biological data). Each machine-learned model enables the digital twin module 450 to automatically analyze a large combination of biosignals recorded for each patient to characterize a patient's current or potential metabolic state.

In order to model a patient's metabolic state and to track changes in their metabolic health, a model, such as a mathematical function or other more complex logical structure, is trained using the combination of input biosignals described above, to determine a set of parameter values that are stored in advance and used as part of the metabolic analysis. Briefly, a representation of a patient's metabolic state is generated by inputting wearable sensor data, lab test, and recorded patient data as input values to the model's function and parameters, and, together with values assigned to those parameters, determines a patient's metabolic health. As described herein, the term "model" refers to the result of the machine learning training process. Specifically, the model describes the generation of a function for representing a patient's metabolic state and the determined parameter values that the function incorporates. "Parameter values" describe the weight that is associated with at least one of the featured input values. "Input values" describe the variables of the function or the conditions to be used in conjunction with the parameter values to determine the risk score. Input values can be thought of as the numerical representations of the various features that the model takes into account, for example the input biosignals. During training, from input values of the training dataset, the parameter values of a model are derived. Further, the training data set is used to define the parameter values at a specified time interval, whereas the input values are continuously updated by the patient's conditions.

The digital twin module 450 may include a combination of machine-learned models to generate various representations of a metabolic state, for example a metabolic models trained to predictively model a patient's metabolic state based on recorded nutrition data, medication data, symptom data and lifestyle data, and to model a patient's true metabolic state based on sensor data and lab test data. The digital twin module 450 may input patient data 420, for example nutrition data, medication data, symptom data, or lifestyle data, into a combination metabolic models (e.g., the nutrition twin model 630 and the lifestyle twin module 670) to predict a patient's metabolic state that would result from the recorded patient data. The digital twin module 450 may compare a recorded timeline of patient data (e.g., foods consumed by the patient, medications taken by the patient, and symptoms experienced by the patient) during a time period to a metabolic state generated for the time period to determine an effect of each food item, medication, and symptom on the metabolic state of the patient.

Additionally, the digital twin module 450 may implement one or more metabolic models to predict a patient's metabolic state that would result from the recommended nutrition, medication, or lifestyle changes included in a recommendation. Alternatively, the digital twin module 450 may receive biological data, for example sensor data and lab test data, as inputs to metabolic models to determine a patient's actual metabolic response to the patient data 420.

Each metabolic model is trained using a training dataset made up of large volumes of historical patient data and biological data recorded for a significant volume of patients, respectively. The training set includes daily metabolic inputs and corresponding daily metabolic outputs. Inputs, for example, include biological data 420 recorded for a current period of time (i.e., different foods, medication, sleep, exercise, etc.) and a patient's initial metabolic state before the patient data 420 was recorded (e.g., based on biosignals derived from sensor data and lab test data). Inputs measured by wearable sensors and lab tests or recorded manually by a patient may be encoded into a vector representation, for example a feature vector, that a machine-learned model is configured to receive. A feature vector comprises an array of feature values each of which represents a measured or recorded value of an input biosignal.

Outputs, for example, include the actual biological data 410, which represents biosignals characterizing a patient's metabolic health (i.e., blood glucose level, blood pressure, and cholesterol). These act as baseline models trained on historical data that can then be applied to new patients with metabolic issues needing treatment to make predictions about those new patients based on what the models have learned from historical patients. Once trained, the machine-learned model may be applied to predict new metabolic states for the new patients based on new combinations of biosignals to predict how a novel set of input biosignals would result in different output signals, for example lowering blood glucose to improve diabetes or lowering blood pressure to improve hypertension.

The models are continuously trained by feeding the input biosignals and metabolic state outcomes for existing and new patients into these models such that the models continue to learn and are continuously updated based on these new data points. For example, after a metabolic state model determines an aspect of a patient's true metabolic state for a time period, the digital twin module 450 may update a training dataset with the determined true metabolic state and a plurality of biosignals recorded during the time period that contributed to the true metabolic state. The metabolic state model(s) are periodically re-trained based on the updated training dataset. This continuously improves the model and allows it to accurately predict future metabolic states for each patient based on their biosignal inputs. In comparison, the metabolic state model is trained or re-trained/modified on a training dataset comprising the information described above for a particular patient.

Figure 7:
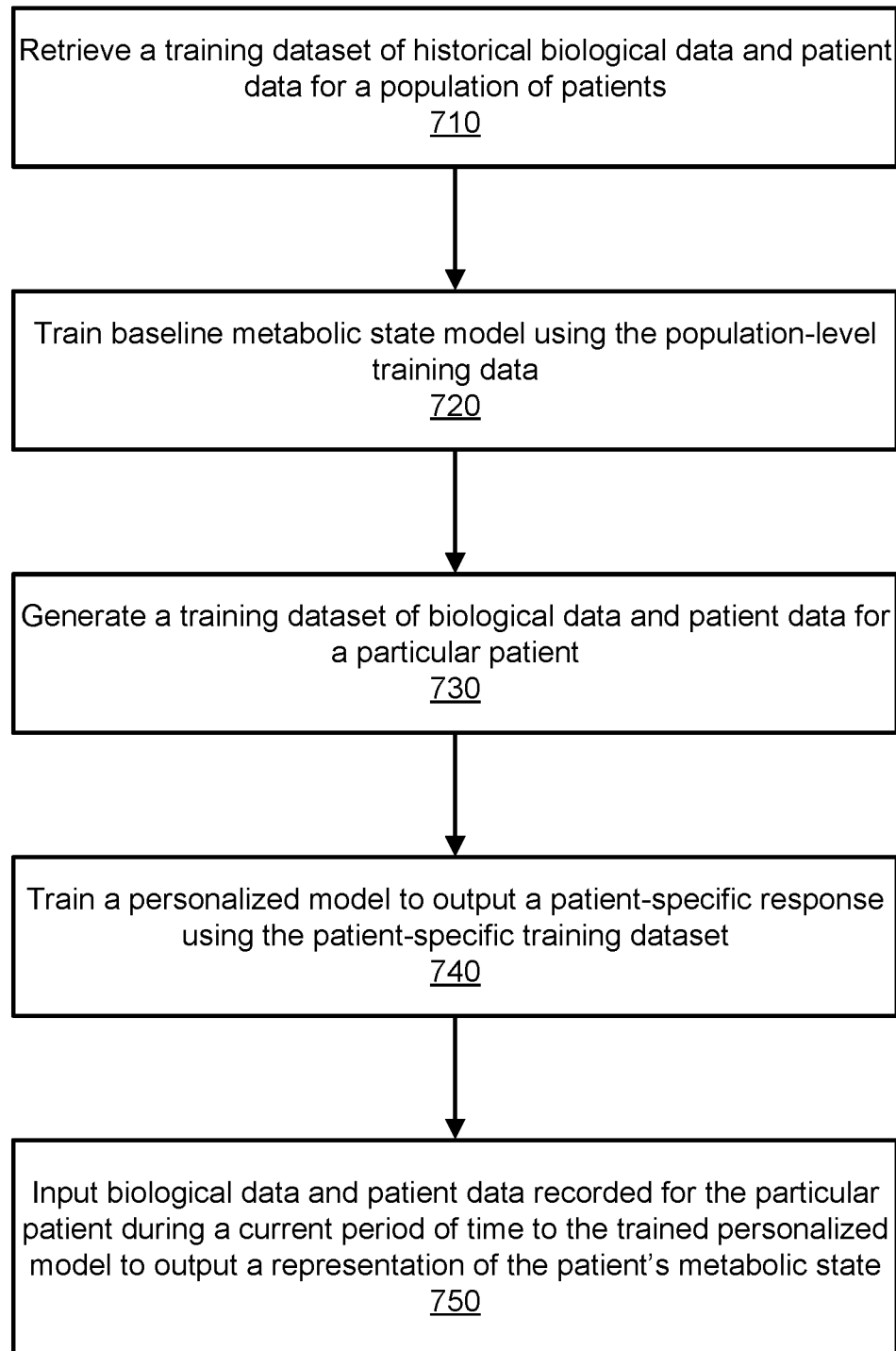
FIG. 7 is a flowchart illustrating a process for training a machine-learned model to output a representation of a patient's metabolic health, according to one embodiment.

FIG. 7 is an illustration of the process for training a machine-learned model to output an aspect of a patient's metabolic health, according to one embodiment. The digital twin module 450 retrieves 710 a training dataset comprised of historical biosignals (e.g., historical sensor data and lab test data) and patient measured and/or recorded for an entire population of patients. Each historical measurement of biological data and record of patient data is assigned a timestamp representing when the patient experienced the measurement/recording and a label identifying its impact on a patient's metabolic health, the patient's metabolic response to the measurement, or both. Using the training dataset of population-level data, the digital twin module 450 trains 720 a baseline model. The training dataset of population-level data comprises labeled metabolic states recorded for a population of patients and sensor data and lab test data that contributed to each labeled metabolic state. Once trained, the baseline model may be implemented to determine a metabolic state of a representative patient of the population of patients (e.g., an average patient) given a set of biological inputs, for example biological data or patient data.

In some implementations, the baseline model may be further trained to generate a personalized representation of a patient's metabolic health. In such implementations, the digital twin module 450 generates 730 an additional training dataset of biological data and patient data for a particular patient. The digital twin module 450 accesses both measured biological data and recorded patient data for a particular patient and aggregates that data into a training dataset. Similar to the historical training dataset, the biological data and patient data of the training dataset are assigned a timestamp and a label to characterize how each biological input impact the particular patient's metabolic state. Using the training dataset of patient-specific data, the digital twin module 450 trains 740 a personalized metabolic model. Once training, biological data and patient data recorded during a subsequent period of time may be input 750 to the trained model to output a representation of a particular patient's metabolic state.

Depending on the type of data input to either the personalized or baseline metabolic model, the digital twin module 450 may generate a representation of a patient's true metabolic state or their predicted metabolic state. Biological data, for example data recorded by a wearable sensor or a lab test, may be input to a model to generate a representation of a patient's true metabolic state consistent with the description above. Alternatively, patient data, for example nutrition data, medication data, symptom data, and lifestyle data, may be input to a model to generate a prediction of patient's current metabolic state consistent with the description above.

Training both models in such a manner enables the patient health management platform 130 to predict a patient's metabolic response to future input stimuli (i.e., patient data 420 recorded by a patient in the future) for not just patients already included in the training dataset, but also new patients included in a holdout dataset because the model only relies on the knowledge representing a patient's current metabolic state and the patient's input stimuli to predict their patient-specific response. Additionally, the model predicts a patient's response to input stimuli for each patient at different stages of his or her treatment because the platform maintains a history of a patient's changing metabolic condition. Finally, it allows for long-range precision prediction of the patient's metabolic state by using current and short-range predictions to inform longer-range predictions.

Figure 8A:
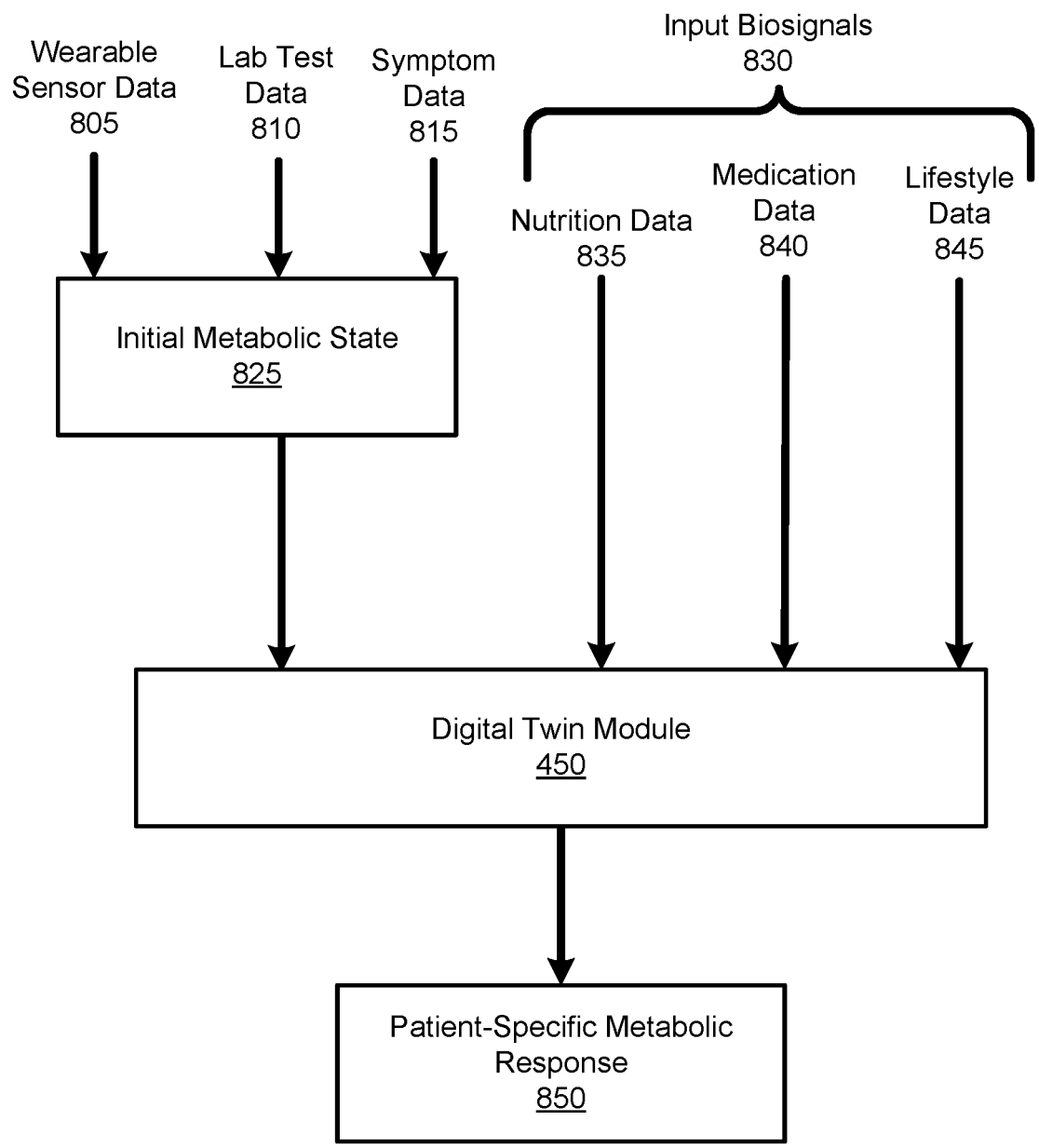
FIG. 8A is an illustration of the process for implementing a machine-learned model to predict a patient-specific metabolic response, according to one embodiment.

FIG. 8A is an illustration of the process for implementing a machine-learned model, according to one embodiment. For a given time period, biosignals recorded as wearable sensor data 805, lab test data 810, and symptom data 815 are representative of a patient's actual, current metabolic state. Accordingly, based on these input biosignals, the patient response module generates an initial metabolic state 825. When sufficient training data exists for a particular patient, the initial metabolic state 825 may be determined using a metabolic model(s). Alternatively, the initial metabolic state 825 may be determined using metabolic model(s) trained for a population of patients. Additionally, the digital twin module 450 relies on input biosignals 830, which represent biosignals that may impact a patient's metabolic state, either deteriorating or improving the state. For example, input biosignals 830 may include nutrition data 835, medication data 840, and lifestyle data 845 recorded for a patient at a time occurring after the generation of the initial metabolic state. In addition to the initial metabolic state 825, the digital twin module 450 receives the input biosignals 830 recorded by the patient as inputs one or more metabolic models. Accordingly, digital twin module 450 models the patient's patient-specific metabolic response 850 to the inputted biosignals. Described differently, the patient-specific metabolic response 850 represents one or more changes in a patient's initial metabolic state caused by, or at least correlated with, the input biosignals 830.

For a second time period following the determination of the patient-specific metabolic response 850, the platform 130 continues to record wearable sensor data 805, lab test data 810, and symptom 815. Given biosignals recorded as wearable sensor data 805 and lab test data 810 as inputs, the aggregated output of the combination of metabolic models (e.g., the true metabolic state) describes what a patient's metabolic response actually is during a time period. Given nutrition data, 835, medication data 840, and lifestyle data 845 (e.g., input biosignals 830) recorded during the same time period as inputs, the aggregated output of the combination of metabolic models (e.g., the predicted metabolic state) describes what a patient's metabolic response should be during the time period. Accordingly, a comparison of the two outputs allows the platform 130 to verify the timeliness, accuracy, and completeness with which a patient recorded the input biosignals 830.

Figure 8B:
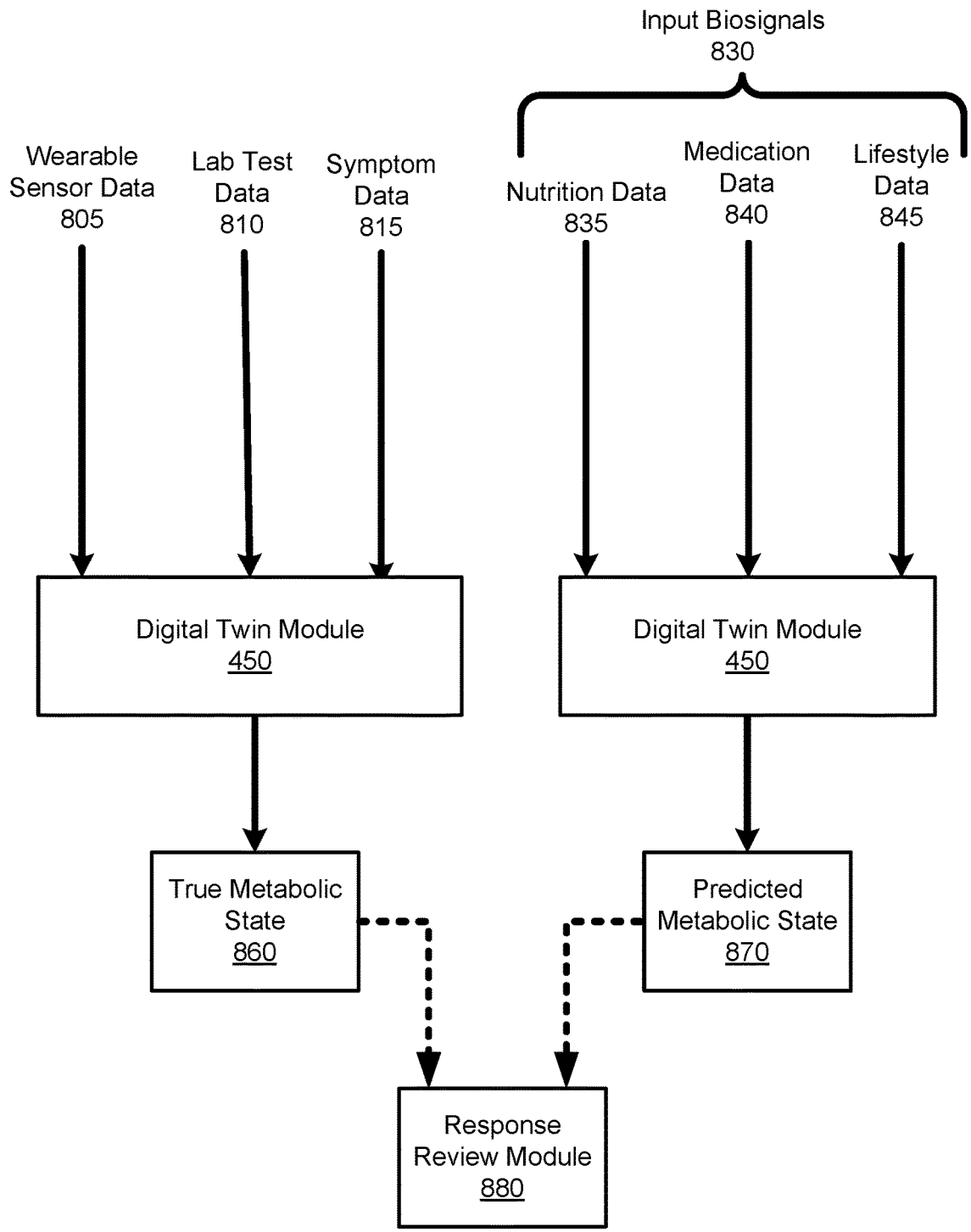
FIG. 8B illustrates the process of comparing a patient's predicted metabolic state with their true metabolic state to verify the timeliness, accuracy, and completeness with which a patient recorded input biosignals, according to one embodiment.

FIG. 8B illustrates the process of comparing the predicted metabolic state for a patient with a true metabolic state for the patient to verify the timeliness, accuracy, and completeness with which a patient recorded input biosignals, according to one embodiment. In the second time period described above, a digital twin module 450 has previously determined a current prediction of a patient's current metabolic health based on the input biosignals 830 recorded during the preceding time period and the patient's initial metabolic state. Accordingly, wearable sensor data 805, lab test data 810, and symptom data 815 recorded during the second time period are input to the metabolic model 850 to determine a patient's true metabolic state 860 during the second time period. Simultaneously, input biosignals 830 recorded during the second time period are input to the digital twin module 450 to generate the patient's predicted metabolic state 870 during the second time period. By comparing the true metabolic state 860 and the predicted metabolic state 870 and identifying discrepancies between the two metabolic states, the patient health management platform may identify or detect an error in the patient's record of input biosignals 830 that contributed to the discrepancy.

IV.D.1 Example Glucose Impact Model

One example of a machine-learned model is a glucose impact model. The glucose impact model described herein is an embodiment of a metabolic model that may be implemented by the glucose twin module 615. The glucose impact model is trained to generate a prediction of a patient's metabolic state based on a training dataset of previous metabolic states of the patient and history of recorded patient data contributing to each previous metabolic state. The glucose impact model generates patient-specific, blood-glucose peak predictions and transforms those predictions into a relative glucose impact of an individual food item (e.g., food items recorded as nutrition data) on a patient's blood glucose levels. Such insight enables a patient, or alternatively a TAC manager 470 associated with the platform 130, to study and learn how various foods which have been previously consumed by the patient and have not yet been consumed by the patient affect their blood glucose. Additionally, the recommendation module 460 may recommend specific foods consistent with the most recent insights generated by the model.

In an example implementation, the glucose impact model has a label 'glucoseMax', and input features including, but not limited to, 'calories', 'carb', 'protein', 'fat', 'fibre', 'glycemicIndex', 'quantity', 'glucoseBaseline', 'efficiency', 'minutesAsleep','minutesAwake', 'activityCalories', 'marginalCalories','caloriesBMR', 'caloriesOut', 'steps', 'fairlyActiveMinutes', 'lightlyActiveMinutes', 'veryActiveMinutes', 'sedentaryMinutes', 'weight', 'height', 'hbalcValue', 'GLICLAZIDE', 'GLIMEPIRIDE', 'METFORMIN', 'OXRA', 'SULFONYLUREA', 'mealType_AFTERNOON_SNACK', 'mealType_BREAKFAST', 'mealType_DINNER', 'mealType_LUNCH', 'mealType_MORNING_SNACK', 'bmiDerived', 'netCarb', 'glycemicLoad', 'netGICarbs'.

Wearable sensors (e.g., continuous glucose monitors) record blood glucose data continuously over a period of time to characterize feature values for 'glucoseBaseline' and 'glucoseMax'. Feature values for 'efficiency', 'minutesAsleep','minutesAwake', 'activityCalories', 'marginalCalories', 'caloriesBMR', 'caloriesOut', 'steps', 'fairlyActiveMinutes', 'lightlyActiveMinutes', 'veryActiveMinutes', and 'sedentaryMinutes' may be recorded by a different wearable sensor, for example an activity tracker. Feature values for 'weight', 'height', and 'hbalcValue' are all captured or calculated from lab test data, for example tests performed during a doctor's visit. Feature values for 'GLI- CLAZIDE', 'GLIMEPIRIDE', 'METFORMIN', 'OXRA', 'SULFONYLUREA' are captured from the medication history, i.e. the types, dosages, and timings of medicines taken by the patient throughout the treatment. Feature values for 'quantity', 'mealType,' 'AFTERNOON_SNACK', 'mealType_BREAKFAST', 'mealType_DINNER', 'mealType_LUNCH', 'mealType_MORNING_SNACK', are manually recorded by a patient as they consume food items (i.e., nutrition data). For specific food items recorded by a patient, features values for 'calories', 'carb', 'protein', 'fat', 'fibre', 'glycemicIndex', 'netCarb', 'glycemicLoad', 'netGICarbs' are accessed from the nutrition database 140 or determined using the nutrition data module 440.

In one specific embodiment, the patient response module implements gradient boosting techniques to model a patient's metabolic response (e.g., a GradientBoostingRegression from the Sci-Kit Library or the XGBoostRegressor from the XGBoostLibrary). Gradient Boosting creates an n number of weak learners, hereafter referred to as "trees," where each new tree is made with the goal of reducing the error from the combination of learners that came before it. Most commonly, the model is trained on 80% of the patient data after cleaning and filtering chosen at random through the entire history of the data and is validated on 20% of the data after cleaning and filtering, chosen at random throughout the entire history of the data. The model predicts glucose peaks ('glucoseMax') which are found by max peak within meal time windows. Those max peaks are normalized and the platform used gradient boosted regression to predict the glucoseMax labels. In optimized embodiments, the model achieves accuracy metrics of RMSE (room mean squared error) of less than 24.6, MAE (Mean Absolute Error) of less than 17.2, MeAE (Median Absolute Error)=13.3, and 91% of all predictions within 40 points of the actual value.

From the predicted max peaks, the patient response module subtracts the lowest peak predicted food item from the peaks of the remaining food items to determine the relative impact of each food item on the blood glucose level for that patient. Because these predictions are personalized based on a patient's biometrics, medications, lifestyle, and nutrition data which they consumed, the impact of each food item is highly specific to an individual patient. The measured glucose impact is normalized relative to a "glucoseBaseline" for the patient, which is defined as the lowest 10% value of the distribution of the data for the previous 24 hours. The glucose impact is penalized (increased) as medications increase because the glucose impact is a relative food peak around the baseline and medications may artificially reduce the glucoseBaseline and the impact of particular foods.

The patient health management platform 130 may classify foods based on their patient-specific glucose impact. Individual foods may be categorized based on their impact on metabolism relative to thresholds established for the general population, for example a first category of food items are recommended to the particular patient, a second category of food items should be sparingly consumed by the patient, and a third category of food items should be avoided altogether by the patient.

IV.D.2 Example 1DG Model

Another example of a machine learned model is a 1DG model which predicts a patient's resulting 1-Day Average Glucose (i.e., a person's average blood glucose level over a 24-hour calendar day) given the patient's starting metabolic state and the record of food items consumed by the patient over 1 or more days (e.g., nutrition data). The 1DG model described herein is an embodiment of a metabolic model that may be implemented by the glucose twin module 615 either instead of or in combination with the glucose impact model describe in Section IV.C.1. The model is trained to generate a prediction of the metabolic state of the patient based on an average blood glucose level of the patient over a 24-hour calendar day given a metabolic profile of the patient and foods consumed by the patient. For example, if a patient adheres to a 7-day long nutrition recommendation outlining particular food items to be eaten as breakfast, lunch, dinner, and snacks during those seven days, the digital twin module 450 is used to predict the patient's 1DG progression over those seven days.

A patient's initial metabolic state is determined based on features including, but not limited to, HBa1c, fasting glucose, minutes asleep/awake, sleep efficiency, sedentary minutes, calories BMR, BMI, calories output, exercise calories output, metformin dosage, glimepiride dosage. Nutrition data including, but not limited to, protein, fat, carbohydrates, fiber, net carbohydrates, net glycemic index carbs, calories, and glycemic load for each recorded food item, as well as derived features created as ratios between nutrients. Features representing ratios of nutritional to personal information are used as well. A highly parallelized optimization algorithm is used to find the optimal combination of features for model performance.

In one specific embodiment, the 1DG model implements gradient boosting techniques to predict a patient's 1DG and their resulting fasting glucose for the first day given all the metabolic features and food features (e.g., a GradientBoostingRegression from the Sci-Kit Library or the XGBoostRegressor from the XGBoostLibrary) in combination with a patient cohorting algorithm. The cohorting algorithm selects discrete subpopulations from the entire universe of patients based on their respective relative metabolic similarity. Separate gradient boosting models are subsequently trained on each of these subpopulations. Gradient Boosting creates an n number of weak learners (trees in our case), where each new tree is made with the goal of reducing the error from the combination of learners that came before it. Most commonly, the model is trained on 80% of the patient data after cleaning and filtering chosen at random through the entire history of the data and is validated on 20% of the data after cleaning and filtering, chosen at random throughout the entire history of the data. In optimized embodiments, the model achieves an accuracy MeAE (Median Absolute Error) of less than 3.5.

Using the 1DG measurement and the fasting glucose measured from the previous day, the 1DG model predicts the 1DG measurement and fasting glucose for the second day. The model iteratively repeats the process from Day n to Day n+1 to predict the 1DG progression for each day included in a patient's nutrition recommendation. In optimized embodiments, the model achieves an accuracy MeAE of less than 6.0 over a 14 day sequence. Based on these personalized predictions, coaches or medical professionals are enabled to understand the impact of a given nutrition recommendation on a patient's metabolic state and modify the recommendation to achieve the best predicted outcome for the patient. Accordingly, the digital twin module 450 and a coach may collaborate to create a patient-specific nutrition recommendation that significantly reduces a patient's blood glucose levels to treat their diabetes. The 1DG model described above may also be used to improve a patient's overall experience using the patient health management platform. In the event that a continuous glucose monitor becomes defective or a patient opts out of wearing a glucose monitor, the 1DG model may be used as an effective replacement for the

IV.E Patient-Specific Recommendations

The recommendation module 460 may include a combination of rule-based artificial intelligence techniques representing codified medical knowledge from established medical practice (e.g., American Diabetes Association guidelines, research literature, and insights gained from past medical treatments). The recommendation module 460 applies the codified knowledge in an automated manner to recommend treatments for new patients using the patient health management platform 130.

The platform 130 additionally categorizes patients into a cohort with other patients with similar metabolic profiles. The recommendation module 460 applies a system of rule to assign patients with a similar metabolic profile to the same cohort. The recommendation module 460 then tailors a specific treatment recommendation (i.e., a combination of nutrition and medication regimens) for the metabolic profiles of patients in each cohort. In some implementations, the recommendation module 460 generates a representative metabolic profile for each cohort based on an average of the metabolic profiles for each patient in cohort or an aggregate of the metabolic profiles for each patient in cohort. The rule-based intelligence applied to categorize patients in cohorts is based on biosignals characterizing a patient's metabolic state or general health, for example biosignals recorded by wearable sensors or measured using lab tests. Specific examples of such cohorting rules include, but are not limited to, BMI, 5-day average blood glucose ("5DG"), 5-day average of grams of net carbs eaten per day ("5dgnc"), 5-day average of the number of >50 mg/dL blood glucose spikes per day ("5dspike"), ketone levels, and whether the patient is taking medications like glimepiride.

Each cohorting rule is applied to a patient's metabolic profile to categorize a patient into either a cohort that complies with the cohorting rule or a cohort that does not comply with the rule. Cohorting rules may be codified in a binary format, for example a patient either satisfies the rule and is sorted into a first cohort or does not satisfy the rule and is sorted into a second cohort. In alternate implementations, a rule may be divided into several ranges of measurements, for example BMI=0 to 22, BMI=23 to 50, BMI=50+. In such implementations, each range of measurements may be associated with a particular cohort such that a patient with measurements falling within a particular range is assigned to a particular cohort.

Rules may be iteratively applied to a patient. For example, a first rule (Rule 1) may be applied to categorize a patient into a first cohort (Cohort A) or a second cohort (Cohort B). A patient whose metabolic state or health does not comply with the first rule may be placed into Cohort B. A second rule may be applied to further categorize a patient into either Cohort B1 or Cohort B2. A patient whose metabolic state or health does comply with the second rule may be placed into Cohort B1. Accordingly, when applied, each rule allows the recommendation module 460 to characterize, both in greater detail and in greater specificity, a patient's metabolic state or health.

Figure 9:
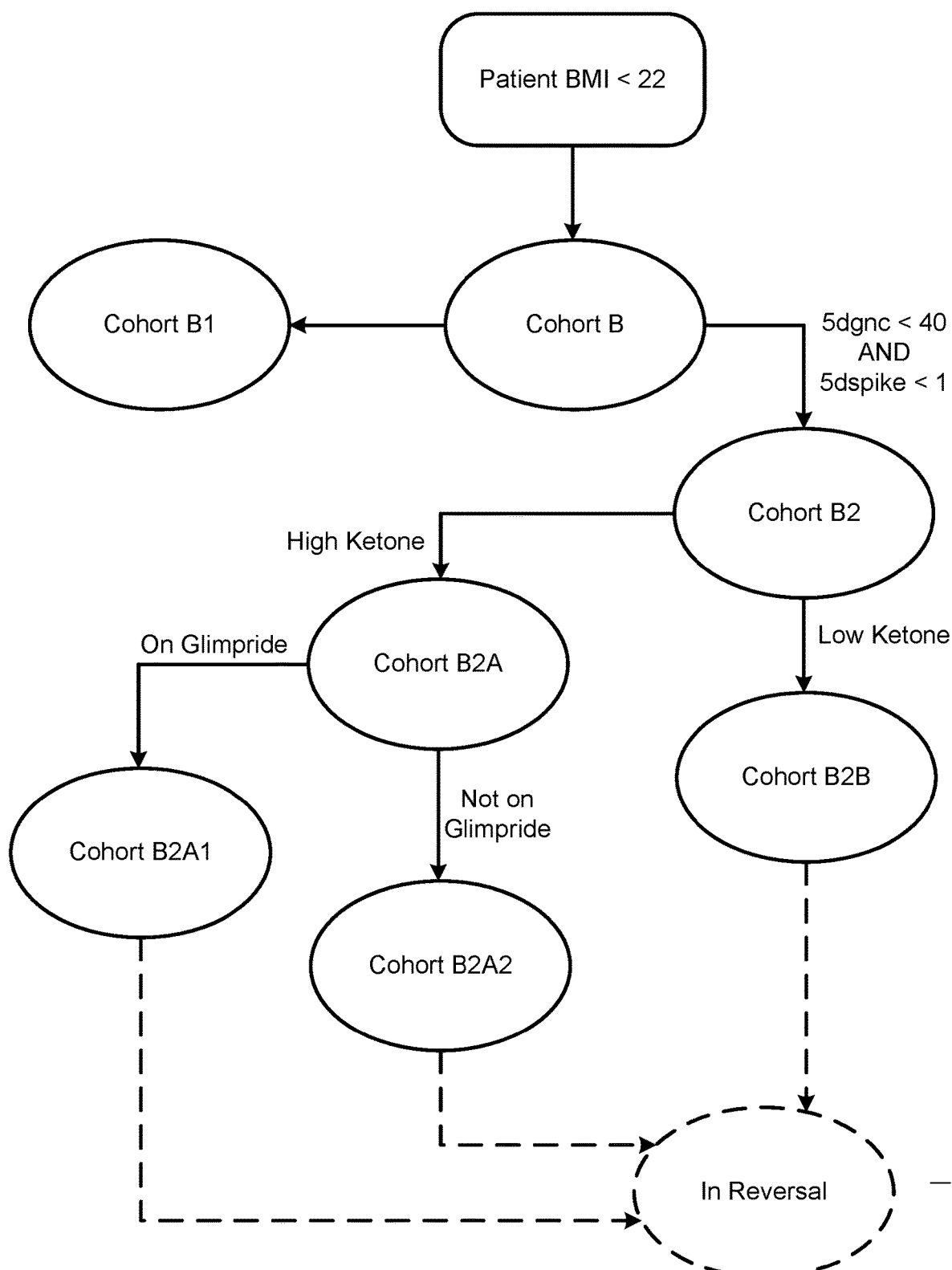
FIG. 9 is an illustration of the process for automatically categorizing a patient into cohorts, according to one embodiment.

FIG. 9 is an illustration of the process for automatically categorizing a patient into cohorts, according to one embodiment. In the illustrated embodiment, the first binary rule applied by the response module determines whether a patient's BMI is above or below 22 ("Patient BMI <22"). Patient's compliant with the rule have BMI's measuring above 22. Such patients are sorted into Cohort B. Although not shown, in the illustrated implementation, patients non-compliant with the rule have BMI's measuring below 22 and are sorted into a different cohort, presumably Cohort A.

Next, the recommendation module 460 applies a combination of binary rules to categorize patients in cohort B into patient's with a 5-day average of grams of net carbs eaten per day above 40 ("5dgnc<40") and a 5-day average of the number of >50 mg/dL blood glucose spikes per day above 1 ("5dspike<1") and patients who do not. Patients who satisfy both conditions are sorted into Cohort B2 whereas patients fail to satisfy either condition are sorted into cohort B1. Accordingly, the rule-based AI applied by the rule-based model 463 conforms to standard Boolean logic operations (i.e., AND, OR). In more complex implementations (not shown), when a combination of rules is applied to a patient, multiple cohorts may exist in which a patient may be categorized. For example, in the example illustrated in FIG. 9, cohort B2 may consist of patients who satisfy both conditions 5dgnc<40 and 5dspike<1, whereas cohort B1 may consist of patients who satisfy neither conditions 5dgnc<40 nor 5dspike<1. Another cohort, for example cohort B3, may consist of patients who satisfy only a single condition, for example 5dgnc<40, but not 5dspike<1. Similarly, a fourth cohort, for example cohort B4, may consist of patients that satisfy the reverse combination of cohort B3, for example 5dspike<1, but not 5dgnc<40. The above description and processing techniques may be applied to combinations of rules greater than two.

From cohort B2, the recommendation module 460 applies a third binary rule categorizing patients in cohort B2 into patients with high ketone counts and patients with low ketone counts. Patient's known to have high ketone counts are sorted into cohort B2A, whereas patients known to have low ketone counts are sorted into cohort B2B. Similarly, the recommendation module 460 applies a fourth binary rule categorizing patients in Cohort B2A into patients taking glimepiride and patients not taking glimepiride. Patients taking glimepiride are placed into cohort B2A1 and patients not taking glimepiride are placed into cohort B2A2. Accordingly, each layer of cohorts represents a categorization with an added layer of specificity compared to the cohorts of the previous layer. In the illustrated embodiment of FIG. 6, the final branch of cohorts includes cohort B2A1 and cohort B2A2. Cohort B2A1 describes a patient with a BMI above 22, a 5-day average of grams of net carbs eaten per day above 40, a 5-day average of the number of >50 mg/dL blood glucose spikes per day above 1, a high ketone count, and taking glimepiride. In comparison, cohort B2A2 describes a patient describes a patient with a BMI above 22, a 5-day average of grams of net carbs eaten per day above 40, a 5-day average of the number of >50 mg/dL blood glucose spikes per day above 1, a high ketone count, but not taking glimepiride. In more complex implementations (not shown), an individual cohort would represent each combination of parameters described in the above example of FIG. 9.

Once placed into a cohort, the metabolic health of a patient is continuously monitored over a period of time. If the metabolic health of a patient improves, the patient is assigned a label "In Reversal" to indicate the improvement in their metabolic health (e.g., the reversal of their metabolic deterioration). As a patient's metabolic health improves or changes, the patient may be reassigned to different cohorts or cohorts with less specificity. For example, when in reversal, a metabolic state of a patient in cohort B2B may indicate average ketone levels.

Accordingly, said patient would be reassigned to cohort B2.

In addition to cohorting rules, the recommendation module 460 may apply a system of rules to make a medication recommendation for a patient or cohort of patients. In particular, the recommendation module 460 applies a set of medication rules to recommend a particular combination of medications (i.e., a comprehensive medication treatment regimen) based on biosignals such as HbA1c levels, 5-day average blood glucose ("5DG"), recent trends in blood glucose (i.e., increases or decreases in blood glucose), creatine levels, BMI measurements, and previously taken medications.

Consistent with the description above of cohorting rules, each medication rule may be codified into a binary format, for example a patient satisfying a condition or plurality of conditions should be prescribed a particular medication or combination of medications, whereas a patient that does not satisfy the condition or plurality of conditions should not be prescribed the particular medication or combination of medications. In addition to being applied to individual patients, medication rules may be applied in conjunction with cohorting rules, for example certain cohorts of patients may be eligible or ineligible for certain medications. In such implementations, each medication rule is compared to a representative health profile for patients in a cohort to determine whether the medication rule applies to the cohort or not. For example, in the example illustrated by FIG. 9, cohort B comprises patients with BMI<22. A medication, for example medication A, may only be safely taken by patients with BMI>22. Accordingly, the recommendation module 460 may apply a medication rule for medication A to both cohort B comprised of patients with BMI<22 and cohort A comprised of patients with BMI>22 to determine that patients in cohort A may safely take mediation A, but patients in cohort B may not. For patients in cohort B, the recommendation module 460 generates an alternative medication or treatment regimen with the same effects as medication A.

Figure 10:
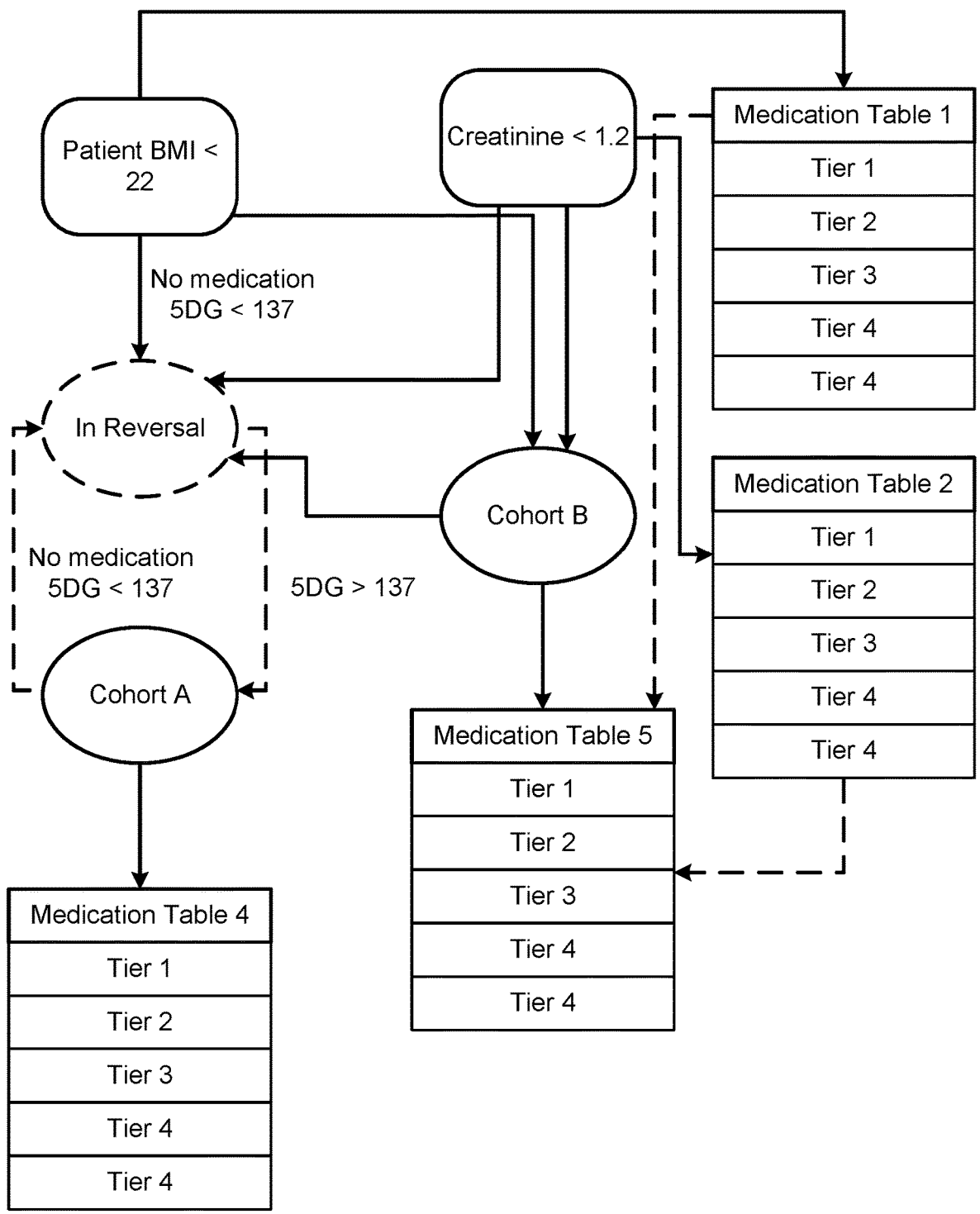
FIG. 10 is an illustration of the process for applying medication rules using rule-based learning, according to one embodiment.

FIG. 10 is an illustration of the process for applying medication rules using rule-based learning, according to one embodiment. In the illustrated embodiment, the patient-specific recommendation module applies a first cohorting rule to determine whether a patient's BMI is greater than 22 ("BMI<22"). Patients that satisfy such a condition are sorted into cohort B. The recommendation module 460 also applies a first medication rule to determine which medications, if any, may be taken by patients with a BMI above 22. Medication Table 1 includes a list of medications which these patients are eligible to take. In some implementations, patients or cohorts satisfying the medication rule may be eligible for multiple mediations that achieve the same result, for example multiple medications for improving blood glucose levels or hypertension. In such implementations, the medications may be organized into tiers (i.e., Tier 1, Tier 2, Tier 3, and Tier 4) based on various conditions, for example efficacy, cost, availability, or risk of side-effects. The tiers may be presented to a patient who may select which of these medications they are most interested in taking.

Also illustrated in FIG. 10, a second cohorting rule may be applied to determine whether a patient's creatinine levels are greater than 1.2 ("Creatinine <1.2"). Patient's that satisfy the condition are also sorted into cohort B. Based on the combination of cohorting rules, patients in cohort B have both a BMI above 22 and creatinine levels above 1.2. The recommendation module 460 applies a second medication rule to determine which mediations, if any, may be taken by patients with creatinine levels above 1.2. Medication Table 2 includes a list of medications which these patients are eligible to take. Consistent with the description of Medication Table 1, medications included in medication Table 2 may also be tiered.

Because patients in cohort B satisfy both the first condition, BMI<22, and the second condition, Creatinine<1.2, those patients are able to take medications in both medication table 1 and medication table 2. Accordingly, the contents of medication table 1 and medication table 2 are aggregated into medication table 5 which is assigned to cohort B. Medications in each tier of medication table 1 are aggregated with medications in the corresponding tiers of medication table 2. As a result, the recommendation module 460 includes multiple treatment regimen (i.e., combinations of medications) that can be recommended to a patient to holistically improve a patient's health. Just like the medications included in each treatment regimen, treatment regimens may also be organized into tiers based on qualities, for example the overall cost of the regimen, efficacy of the regimen, and overall availability of the regimen. For example, a tier 1 treatment regimen for a patient in cohort B consists of a medication from both tier 1 of medication table 1 and medication table 2.

The American Diabetes Association has defined the threshold for diabetes as an HBA1C measurement greater than 6.5, which is equivalent to the 5-day average blood glucose measurement exceeding 140. Accordingly, patients measuring 5DG <140 while taking no diabetes medication are considered to be in diabetic reversal (i.e., their metabolic health is improving). Such patients are assigned the label "In Reversal." When the metabolic health of a patient labeled "In Reversal" continues to improve, for example the 5DG measurement remains below 140 without medication, the patient maintains the "In Reversal" label. Alternatively, if the metabolic health of a patient labeled "In Reversal" deteriorates, for example the 5DG measurement increases above 140, the patient is reassigned to cohort A. Patients in cohort A satisfy the conditions of 5DG>140. To address that condition, patients in cohort A may be recommended one or more medications listed in Medication Table 4.

IV.F TAC Manager Implementations

Timeliness, accuracy, and completeness measurements are used to evaluate a patient's adherence to a recommendation and their overall metabolic health management may be determined for multiple biosignals, for example patient data 420, recorded by the patient health management platform. For nutrition data 320, the patient health management platform measures the timeliness with which the data is recorded by the patient. For example, as the digital twin module 450 generates an updated representation of the patient's metabolic state, the platform 350 may determine a time delay between which a patient consumed a food item and they recorded the consumption of said food item. The platform may further evaluate the accuracy with which the patient records the consumption of a food item. As described herein, such accuracy refers to an exact quantity and measure of the food item, and the completeness of the record of consumed food items. Similarly, for medication data 330 the patient evaluates whether the medication is taken at times consistent with a prescribed or recommended treatment regimen, whether the dosage taken is consistent with the prescribed or recommended treatment regimen, and whether the patient takes all of the medications prescribed or recommended by the treatment regimen.

For sensor data 310 (e.g., measurements recorded using a weighing scale, a blood pressure meter, a glucose meter, a continuous glucose monitor, or a wearable device), the platform 350 may measure whether the relevant biosignals were recorded within a specified timeframe, whether all relevant sensor data is both recorded within the specified timeframe for a particular patient and whether those measurements fell within an expected range. In addition to those described above, a patient health management platform may determine TAC measurements for other biosignals including, but not limited to, lab test data, symptom data, or lifestyle data.

Using the determined TAC measurements, the patient health management platform 350 may generate or dynamically update a patient-specific recommendation and deliver such a recommendation to a patient via an application on a patient device, for example the patient health management application 385 on patient device 380. For example, based on TAC measurements determined for the preceding time period, the platform may generate a recommendation which accounts for deficiencies identified in the patient data recorded for the preceding time period and generate a recommendation for improving those deficiencies. Alternatively, given deficiencies identified for a current time period (e.g., a patient's lack of a particular nutrient) the platform may dynamically update a recommendation for that current time period to ensure that a patient consumes the recommended dose of the vitamin. The patient health management platform 350 may, additionally, implement a variety of automated mechanisms, machine learning models, and interactive user interface elements to encourage a user to maintain high TAC measurements in their data entries.

Figure 11:
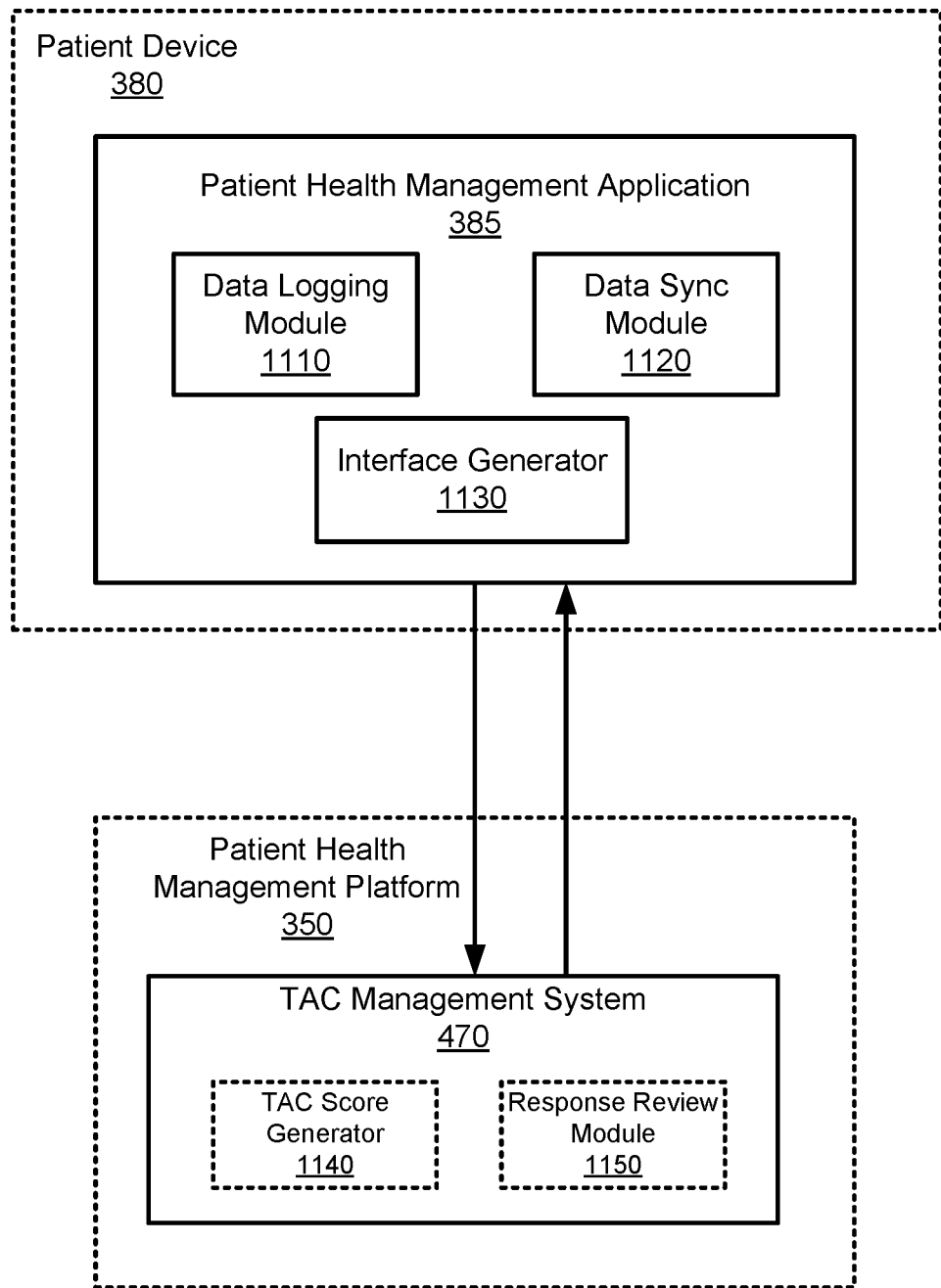
FIG. 11 is a block diagram of the system architecture for a TAC management system including an application on a patient device and the patient health management platform, according to one embodiment.

FIG. 11 is a block diagram of the system architecture of a TAC management system including a patient health management application 385 on a patient device and the patient health management platform 350, according to one embodiment. The TAC management system includes a patient health management application 385 presented to a user via a patient device 385 and a patient health management platform 350. In some embodiments, the platform 350, may be stored at a server separate from the patient device, whereas in other embodiments, the platform 350 may be stored on the patient device. The patient health management application 385 may further include a data logging module 1110, a data sync module 1120, and an interface generator 1130. The patient health management platform 350 may include a TAC manager 470 consistent with the description in FIG. 4 that further includes a TAC score generator 1140 and response review module 1150. However, in other embodiments, a different combination of the above components may be stored in the patient health management platform 350, the application 385, or both. The platform 350 or the application 385 may include different and/or additional components to perform the same functions described with regards to the TAC management system illustrated in FIG. 11.

The data logging module 1110 implements several data capture techniques to efficiently capture and communicate both patient data and biological data. In one implementation, the data logging module 1110 operates in conjunction with the interface generation 630 to generate a data entry interface to be displayed to a user. For example, a data entry interface may include a plurality of data entry fields allowing a user to typographically specify or select a food item, a medication, or a symptom, a timestamp associated with the entry, and any other relevant information (e.g., a quantity of the food item). The data entry interface may also allow a user to view and/or revise previous entries if an error is detected in the entry. In another implementation, the data logging module 1110 uses audio-transcription techniques to automate data capture (i.e, a voice-to-food approach). A voice-to-food approach enables patients to log their consumption of every food in every meal as quickly as possible while also reducing the likelihood that they forget to record their consumption entirely or that they incorrectly record their consumption.

A patient may speak directly into a microphone embedded in the patient device 385. The data vocalized by a patient may be recorded and processed in near real-time to convert the audio recording into a text message. The data logging module 1110 may implement natural language processing techniques to transcribe an audio recording into text, to parse the text into multiple food logs, and to return the parsed food logs to a patient for review and confirmation. The converted text message may be presented to the patient for review or for confirmation via the interface generator 1130. The presented interface may enable a patient to edit or add additional information to the converted text message, for example using an additional recording or a typographical input.

In some embodiments, the data logging module 1110 implements artificial intelligence or machine-learning techniques to more accurately process the syntax of an audio recording. For example, if a patient has an accent and records a banana for the first, the data logging module 1110 may be unable to identify the food item as a banana from the audio recording. The data logging module 1110 may communicate instructions to the interface generator 1130 for the patient to manually log the food item. Subsequently, the data logging module 1110 draws a correlation between the sound in the audio recording and the manually recorded food item. In a future data entry, the data logging module 1110 may receive a recording in which the user again consumed a banana, however, this time the data logging module 1110 is able to map the sound to the food item "banana." To facilitate such dynamic training of the data logging module 1110, when the data logging module 1110 is unable to conclusively identify a food item from an audio recording, the interface generator 1130 may request visual confirmation from the patient. If the record generated by the data logging module 1110 is correct, the data logging module 1110 stores the association for future reference. If the patient manually corrects the interface via the confirmation interface, the data logging module 1110 updates and stores the association between the audio and the entered item.

In another example, the data logging module 1110 may be further personalized based on the objectives in a patient's current patient-specific recommendation. For example, when recording an audio entry of a food item, a patient specifies "cream tea." However, based on the patient's enunciation, the data logging module 1110 may be unable to distinguish between "cream tea" and "green tea." The data logging module 1110 may reference the patient's patient-specific recommendation and objectives related to nutrition data to determine whether green tea or cream tea is in the recommendation's nutrition plan. If the recommendation does call for a patient to consume "cream tea," the data logging module 1110 selects "cream tea" instead of "green tea." Alternatively, if the recommendation calls for neither cream tea nor green tea, the interface generator 1130 presents a confirmation interface for the patient to confirm whether they meant cream tea or green tea. In some embodiments, even if the recommendation calls for one option, but not the other (i.e., cream team, but not green tea), the interface generator 630 requests confirmation from the user and further trains data logging module 1110 to decipher the patient's syntax.

The data sync module 1120 automatically synchronizes data communication between each sensor configured to record sensor data and the patient health management application 385. In alternate embodiments, the data sync module 1120 may be stored directly on the patient health management platform 350. By synchronizing the receipt of sensor data at periodic intervals, the data sync module 1120 confirms that patient-specific recommendations are generated based on data that accurately represents a patient's metabolic state. Using the combination of the data logging module 1020 and the data sync module 1120, the patient health management application 385 enables a patient to streamline daily reporting processes while reducing manual, typographical errors. Additionally, by implementing audio transcription techniques, the patient health management application allows a user to record patient data without having to painstakingly transcribe that data manually.

Biological data synchronously received from wearable sensors or lab tests and patient data recorded via the data logging module 1110 is communicated to the patient health management platform 350, for example via the network 150. At the patient health management platform 350, the TAC manager 470 evaluates a patient's TAC measurements by tracking the patient's progress through the recommended objectives. Based on the completed objectives, a ratio of completed objectives to incomplete objectives, or a combination thereof, a TAC score generator 1140 generates a TAC score to provide feedback to patients, coaches, providers. The TAC score additionally encourages a patient to maintain or improve their adherence to a most recently generated patient-specific recommendation.

As discussed above, a patient-specific recommendation comprises a combination of nutrition objectives, medication objectives, and lifestyle objectives that, when completed, would either improve a patient's metabolic state to an optimal state or to maintain the patient's optimal metabolic state. The TAC score generator 1140 computes a numerical TAC score based on a patient's progress completing outlined objectives. Accordingly, the TAC score, also referred to as a completion score, reflects the completion of a patient's daily objectives. The TAC score may additionally be computed based on nutrition data, medication data, lab test data, wearable sensor data, and other lifestyle data.

The numerical score may be a percentage ranging from 1 to 100, a decimal ranging from 0 to 1, or another value within a range of numeric values. As a patient completes objectives in a recommendation, their TAC score may be dynamically updated. In some embodiments, the TAC score is proportional to the number of objectives completed, the type of objectives completed, or a combination thereof. As a basic example, if a recommendation includes ten objectives, each time a patient completes an objective, their TAC score increases by 10%. In a more complex example, if a patient completes an objective for a lifestyle adjustment (e.g., completing a 3 mile walk), the TAC score may increase by a more significant margin than if the patient were to complete an objective for eating a single food item, for example a banana. Other embodiments of the TAC score generator 1140, may implement a combination of the above techniques to compute a patient's TAC score.

In some implementations, a TAC score may be presented to a patient with a message, for example encouragement to improve their adherence to a recommendation or to maintain their adherence, an explanation of the effect of a patient's adherence to a recommendation on the patient's metabolic state, or other contextually relevant data.

As the TAC manager 470 continues to receive additional recordings of patient data (e.g., updated food consumed by the patient or medications taken by the patient, the TAC score generator 1140 may determine that the additional recordings of patients indicate completion of one or more previously uncompleted objectives by the patient and increase the TAC score accordingly. In one embodiment, the TAC score is increased by a value representing the one or more previously uncompleted objectives, for example a value that is proportional to the difficulty of each previously uncompleted objective. As the TAC score increases, the patient device may generate an interface informing the patient of the increased score. When a patient achieves a daily TAC score of 100%, the patient device may generate an interface presenting a celebration, for example a fireworks animation, to congratulate the patient and further encourage them. The TAC score may additionally be penalized for patient data that is not recorded in a timely, correct, and accurate matter. For example, the TAC manager 470 determines that patient data was recorded with a time delay above a threshold timeframe, a patient's TAC score may be reduced.

As described above in Section IV.B, individual food items may be assigned personalized categorizations, for example color labels, describing whether or not a food item positively impacts a patient's metabolism. Although a patient-specific recommendation recommends food items that improve a patient's metabolic states in appropriate amounts to improve their state, a patient may not adhere to the recommendation and, instead, enter food items that negatively impact their metabolism. In such implementations, the TAC score generator 1140 accesses the nutrition database or personalized layer of the nutrition database to identify an alternative food item that is of the same family and similar to the entered food item, but also will improve the patient's metabolic state. The TAC score generator 1140 communicates one or more of these alternative food items to the interface generator 1130 which generates a recommendation for presentation to the patient.

As described above with reference to FIG. 4 and FIG. 7, the patient health management platform uses machine learning models to predict a patient's metabolic response to a set of recorded inputs (e.g., their current metabolic state and food consumed) and to determine a patient's true metabolic response based on biosignals recorded by wearable sensors or lab tests, (e.g., blood glucose measurements). The response review module 1150 compares the predicted metabolic state with the true metabolic state and determines whether the two states are significantly different. As described herein, a significant difference is determined based on a threshold level of similarity defined by a provider or coach. In implementations in which the two metabolic states are significantly different, the response review module 1150 notifies the patient of the discrepancy and potential instances of incorrectly recorded patient data that may have caused the discrepancy. The response review module 1150 may also notify a provider or coach of the inconsistency so that the provider or coach may aid the patient in addressing the recording error and encourage improved adherence.

IV.F.1 TAC Score Computation

Figure 12:
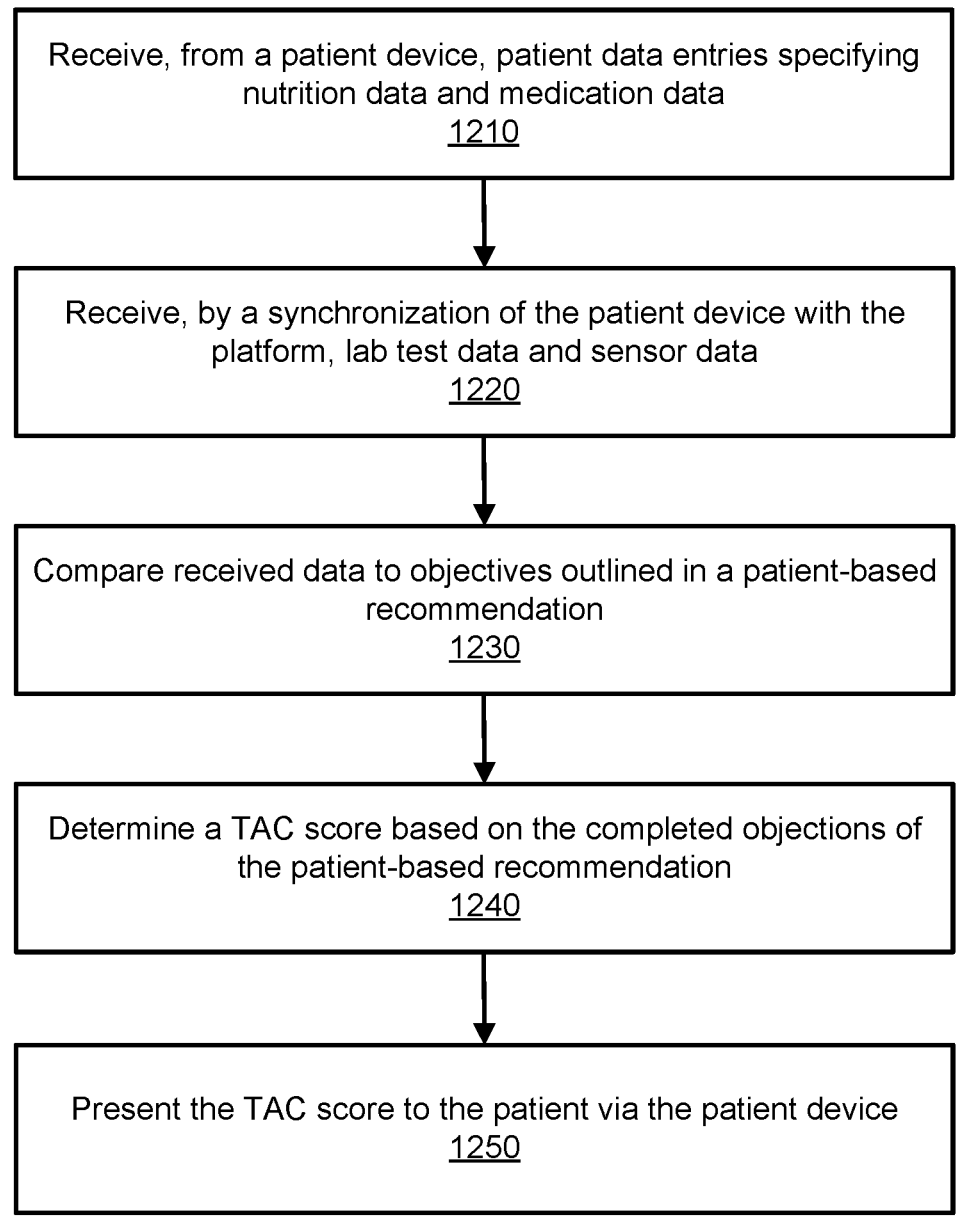
FIG. 12 is a flowchart illustrating a process for generating a TAC score based on a patient's TAC measurements, according to one embodiment.

FIG. 12 is a flowchart illustrating a process for generating a TAC score based on a patient's TAC measurements, according to one embodiment. The patient health management platform 350 receives 1210 patient data entries specifying nutrition data and medication data from a patient device. Simultaneously, or within a threshold amount of time of receiving the patient data, the platform 350 synchronously receives 120 data recorded by lab tests or wearable sensors. The patient health management platform 350 compares 1230 the received patient data, lab test data, and sensor data to the objectives outlined in the patient-specific recommendation and determines 1240 a TAC scored based on the completed actions. The generated TAC score is communicated back to the patient device where it is presented 1250 to the patient via a graphical user interface on the patient device.

In one implementation, the TAC score generator 1140 computes a TAC score using the combination of the equations and relationships defined below:

$$TAC = (W_{diet} \times Score_{diet}) + (W_{med} \times Score_{med}) + (W_{suppl} \times Score_{suppl}) + (W_{report} \times Score_{report}) + (W_{act} \times Score_{act}) Score_{max}$$

where, $Score_{diet}$ represents a metric of a patient's adherence to their recommended nutrition regimen, $Score_{med}$ represent a metric of a patient's adherence to their recommended medication regimen, $Score_{suppl}$ represents a metric of a patient's adherence to their recommended supplement regimen, $Score_{report}$ represents a metric of a patient's overall TAC score for reporting patient data, $Score_{act}$ represents a metric of a patient's adherence to their recommended lifestyle/activity regimen. $W_{diet}$, $W_{med}$, $W_{suppl}$, $W_{report}$, and W$act$ represent the relative weights of the score components in the TAC score calculation.

IV.F.2 TAC Interfaces

Figures 13A, 13B:
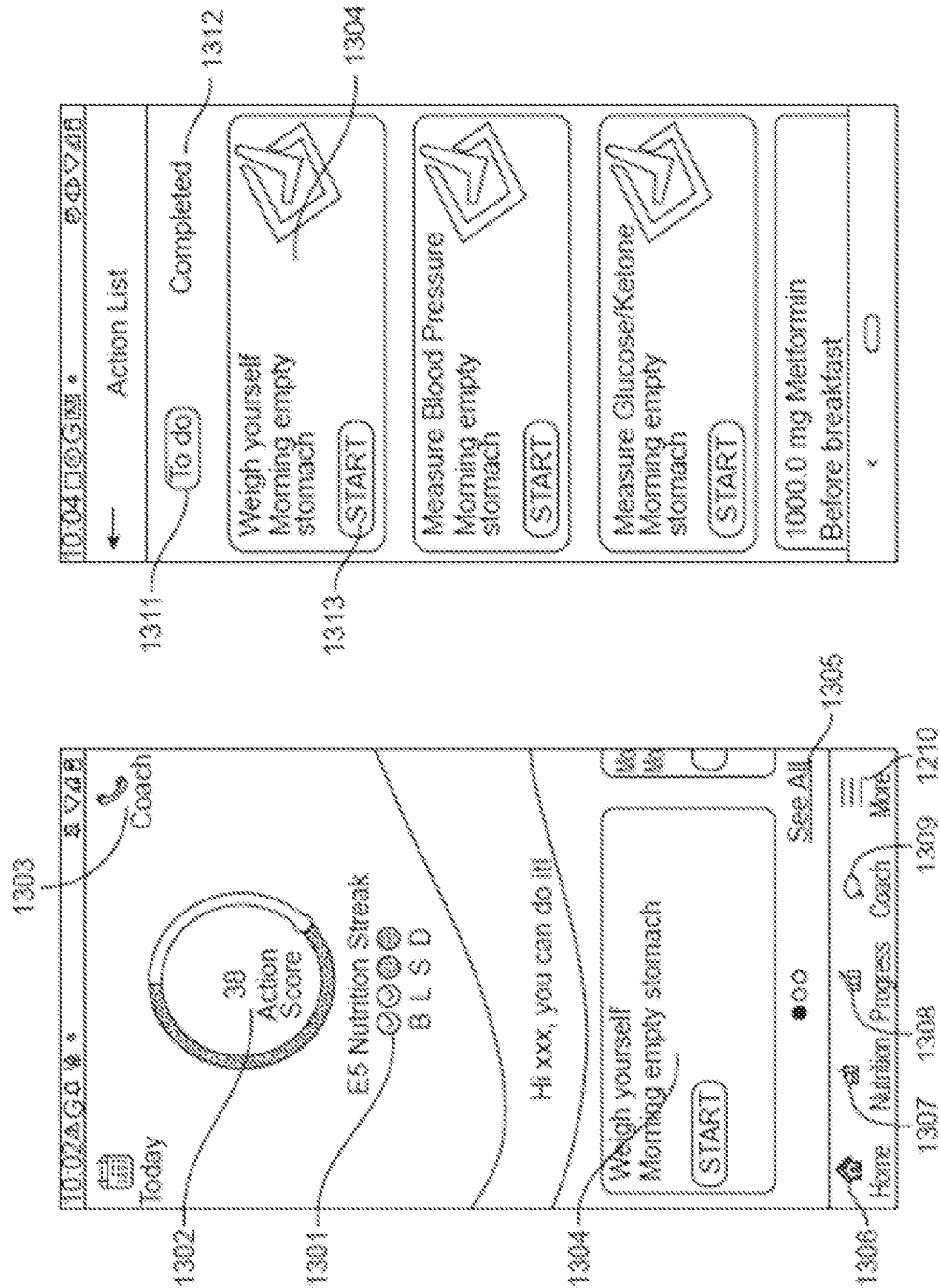
Figures 13C, 13D:
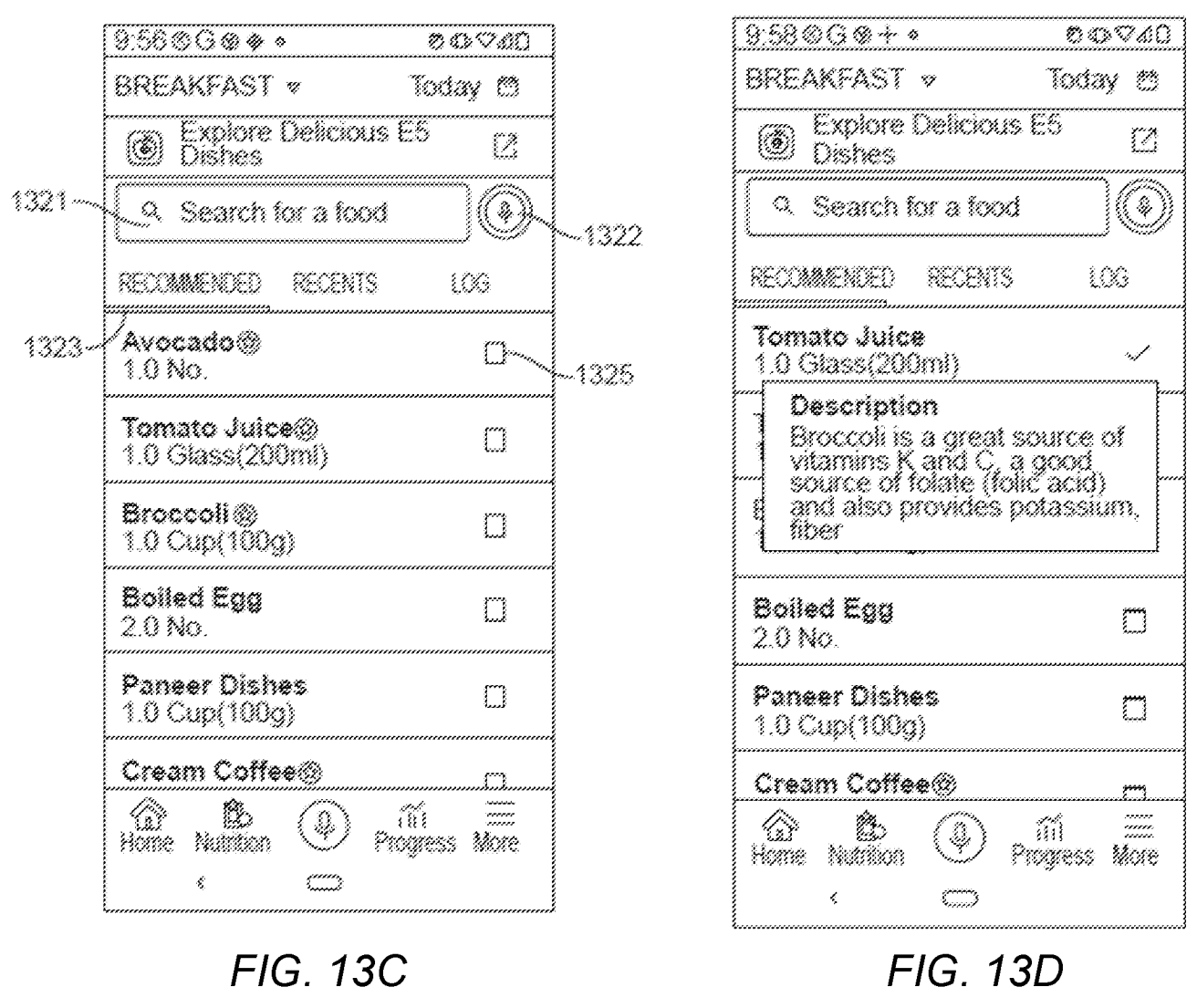
Figure 13F:
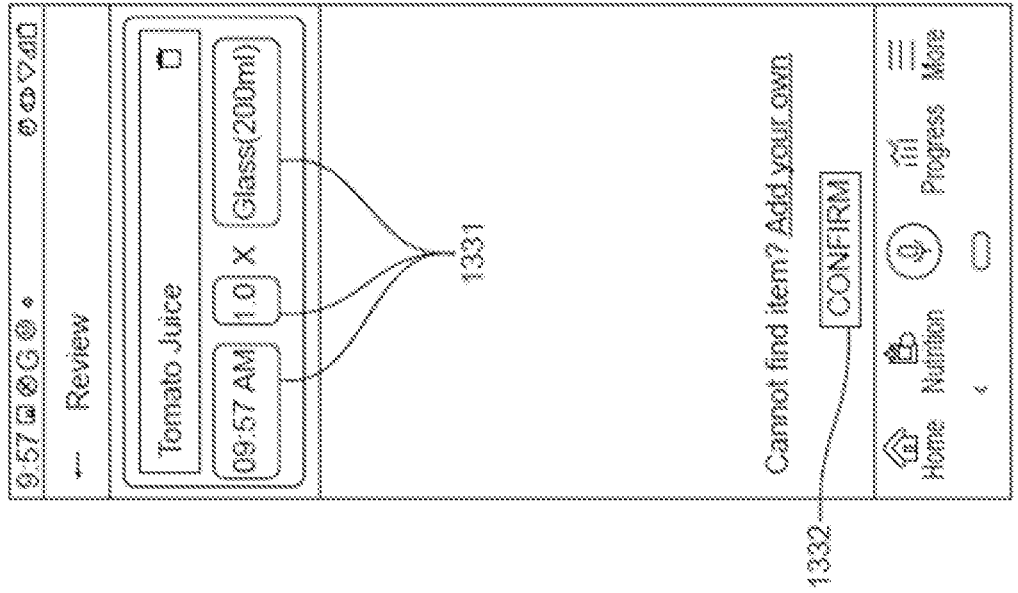

FIG. 13A illustrates a home page of a graphical user interface including a plurality of navigation options (i.e., 1306, 1307, 1308, and 1309). Each navigation option redirects a patient to an alternate graphical user interface associated with a different functionality. Selection of the home navigation option 1306 redirects a patient back to the interface illustrated in FIG. 13A. Selection of the nutrition navigation option 1307 redirects a patient to an interface configured to receive nutrition data entries. Such interfaces are discussed with reference to FIGS. 13C-F. Selection of the progress navigation option 1308 redirects a patient an interface that presents a patients TAC scores over a period of time. Such an interface is discussed with reference to FIG. 13L. The coaching navigation option 1309 redirects a patient to an interface through which they may contact a coach or provider, review previous conversations with the coach or provider, review notes or feedback received from their coach or provider, or a combination thereof. The additional functions navigation option 1310 redirects a patient to interfaces with other functionalities described below with reference to FIGS. 13B-L.

The illustrated home interface includes a TAC score presented to a patient via a patient device, according to one embodiment. In the illustrated embodiment, the numerical TAC score 1301 is presented with a graphical representation of a patient's progress (i.e., the highlighted fraction of the circle surrounding the TAC score). Additionally, the interface includes a streak counter 1302 which tracks whether the patient has recorded nutrition data for each of breakfast, lunch, snack, and dinner (i.e., B, L, S, and D) and a graphic indicator describing the status of nutrition data for each meal. The interface additionally includes a contact interactive element 1330 that enables a patient to contact a coach or medical provider regarding any queries related to data entry or adherence to the patient-specific recommendation. The illustrated interface includes several objective display panels 1304 for a patient to complete (in addition to recording nutrition data) describing actions or measurements for a patient to take. Each objective may be displayed on a separate display panel 1304 and a patient may review each panel by swiping through the set of objectives.

Alternatively, in response to a selectable "See All" graphical element 1205, the list of objectives may be presented as a single list. FIG. 13B illustrates a list of objectives presented in response to the selection of the "See All" graphical element 1305, according to one embodiment. The list of objectives may further be organized into a first set of uncompleted tasks and a second set of completed tasks. In response to the selection of uncompleted objectives selectable graphical element 1311, the list of uncompleted objectives may appear (as illustrated in FIG. 13B). Alternatively, in response to the selection of a completed objectives selectable graphical element 1312, the list of completed objectives may appear (not shown). The selected list of objectives resembles a vertical display of all objective display panels 1304 previously presented in the interface illustrated in FIG. 13A. In embodiments in which the list of objectives is too long to fit on a screen, the interface may include a scrollable element (not shown) to continuously review the objectives. Each objective display panel 1304 includes a "Start" selectable graphical element 1313 enabling a user to manually enter data, for example using voice-to-text techniques, relevant to an objective. For example, in response to a "Weight yourself" objective display panel 1304, a patient may select the "Start" selectable graphical element 1313 to manually record their weight. As described above, a patient may manually record data with a typographical input or by recording an audio message addressing the objective.

In response to the selection of an objective display panel 1304 for a user to record what they ate for a particular meal, the interface generator generates a graphical user interface for a user to record such food. FIG. 13C illustrates a data entry interface for a patient to record food consumed during breakfast, according to one embodiment. FIG. 13C may also be generated in response to the selection of the nutrition navigation option 1307. As described above, a patient may vocally record such nutrient data, for example using the selectable microphone element 1322. Alternatively, a patient may manually record such nutrient data by directly selecting foods and specifying the quantities of foods via the graphical user interface. In such embodiments, the interface may include a search element 1321 which allows a user to search for particular food items in the nutrition database. Food items may be further categorized into food items recommended in the patient-specific recommendation, recent food items logged historically by the patient for a certain meal (or for all meals), and a log of all food items that have been logged within a recent period of time. Selection of any of these categories via the list selectable graphical element 1323 results in the presentation of a list of food items within that category. In the illustrated embodiment of FIG. 13C, the "Recommended" selectable element 1323 is selected. Each entry in the resulting list includes a selectable food label 1324 specifying the name of the food item and the recommended quantity in which the food item should be consumed. A user may confirm which food items from the recommended list were actually consumed by selecting or unselecting a selectable confirmation graphical element 1325.

In response to the selection of a selectable food label 1324 for a food item, a description of the benefits of the selected food item may be displayed to a user. FIG. 13D illustrates a description display panel presented in response to the selection of a label for broccoli, according to one embodiment.

Figure 13E:
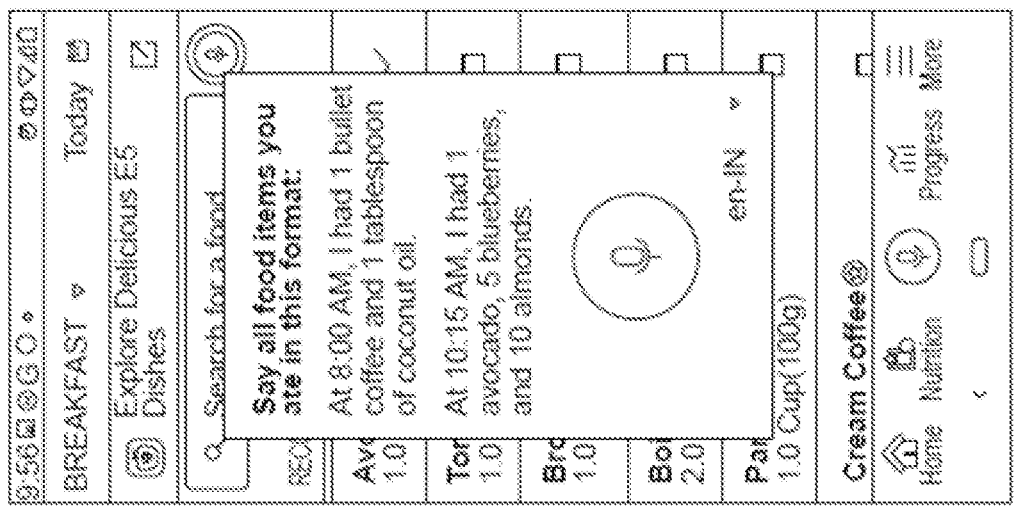
Figure 13I:
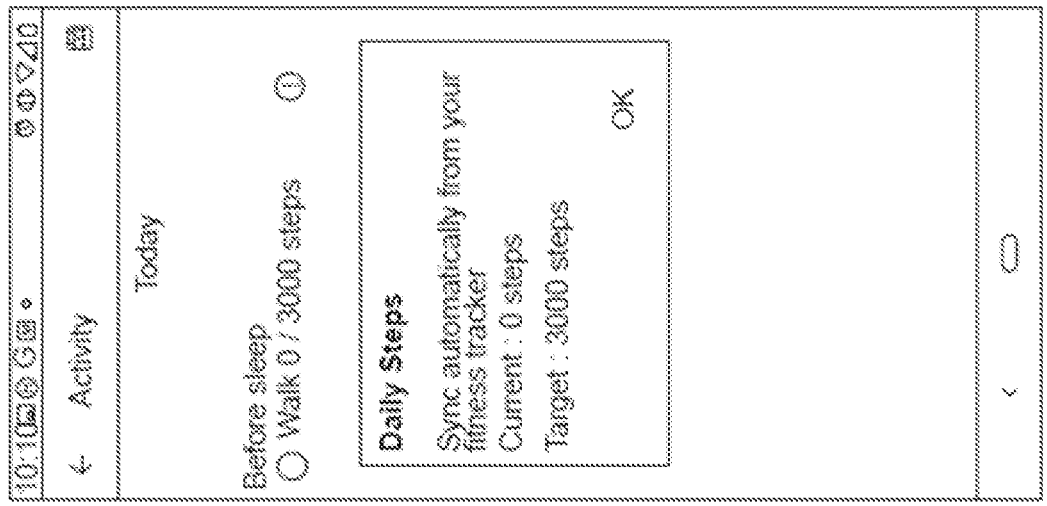

In response to the selection of the selectable microphone element 1322, the interface generator 1130 presents an audio display panel with instructions for a user to vocally specify food items and describe the quantity of those consumed food items. FIG. 13E illustrates an audio display panel for a user to dictate food items that they have consumed, according to one embodiment. In the illustrated embodiment, the interface further includes examples for a format for the dictation. The format may include a food item that was consumed, a time at which the food item was consumed, and the quantity in which the food item was consumed.

After the specification of consumed food items, either by an audio recording or a manual input, the interface generator 1130 generates a confirmation interface for presentation to a user. FIG. 13F illustrates a confirmation interface for presentation to a user, according to one embodiment. The confirmation interface includes multiple editable graphical elements 1331 specifying the time at which the food item was consumed and the quantity at which the food item was consumed. In implementations in which the data logging module 1110 incorrectly deciphers an audio recording, a patient may manually edit the recorded information by manually entering information into the editable graphical elements 1331. After confirming the correctness of the recorded information, a patient may select the selectable confirmation graphical element 1331 to confirm the entry. The entry is then updated to a patient's log of nutrition data and the corresponding objective is then updated as having been completed.

Similar to the interface for entering nutrition data described with reference to FIG. 13C, the interface generator 1130 may also generate an interface for a patient to record medication data. FIG. 13G illustrates an interface for recording medication data, according to one embodiment. The illustrated interface includes a plurality of medications, times or conditions under which each medication should be consumed, and an amount of each medication to be consumed. The list of medications may be generated based on medications included in the most recent patient-specific recommendation or a set of the most recent patient-specific recommendations. Each medication entry includes a selectable confirmation graphical element 1341 that, when selected, indicates that the medication was taken in the prescribed amount at the recommended time.

Figure 13H:
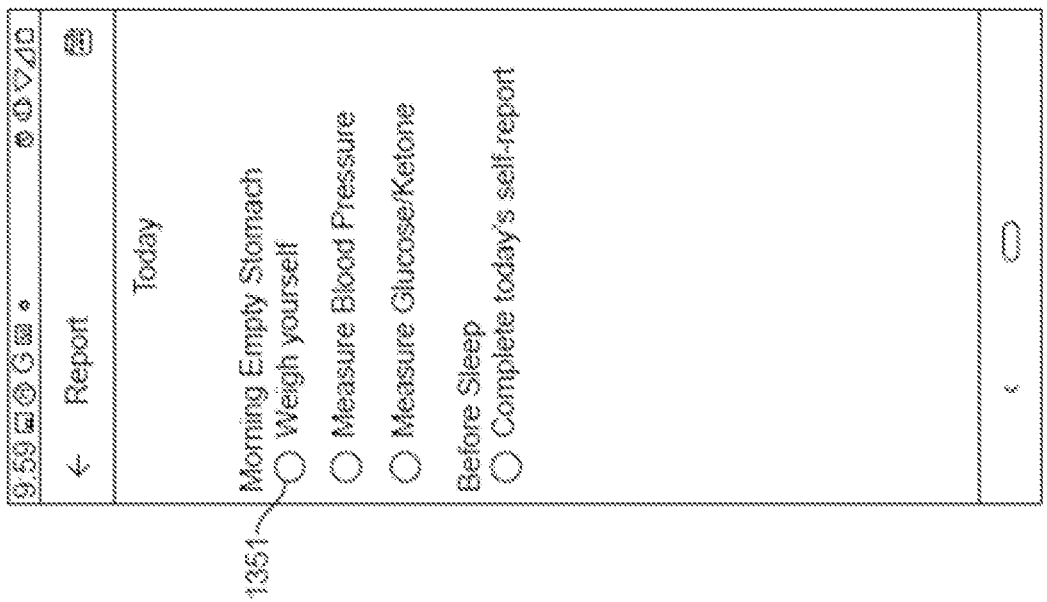
Figures 13J, 13K:
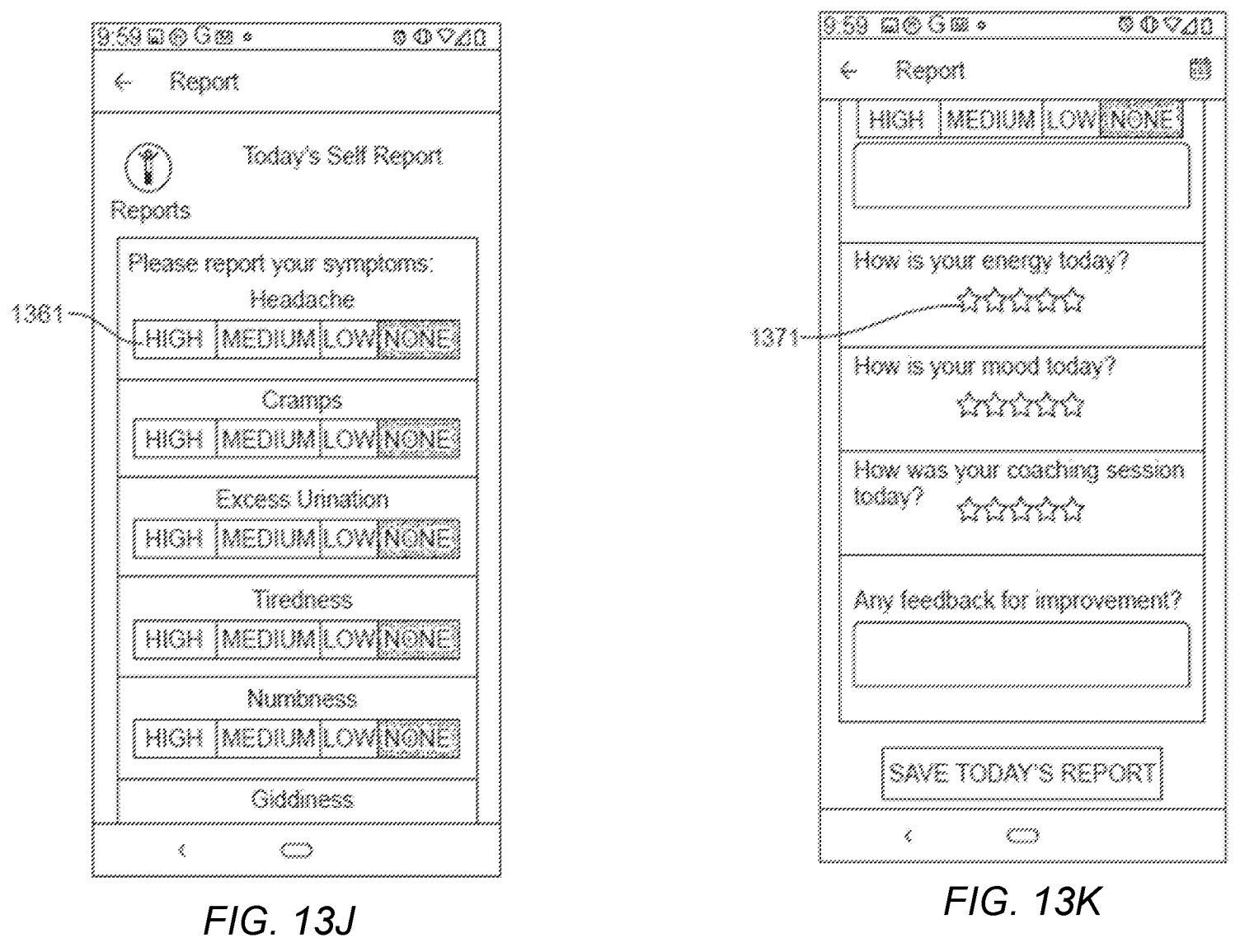
Figure 13L:
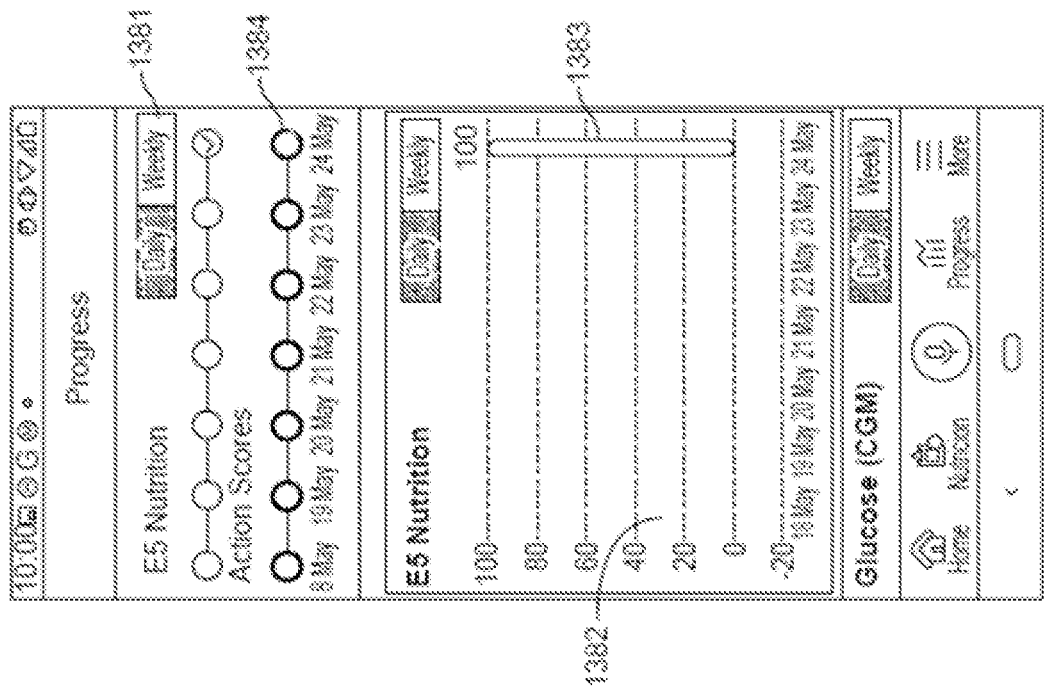

The interface generator 1130 may generate an interface describing the status of objectives related to wearable sensor data recordings. FIG. 13H illustrates an interface presenting the status of objectives addressed using sensor data recordings, according to one embodiment. In the illustrated embodiment, each objective includes a confirmation graphical element 1351 similar in function and description to the confirmation graphical element 1341. Unlike the nutrition data and medication data described with reference to FIGS. 13C and 13H, the illustrated objectives, for example "weigh yourself," "measure blood pressure," and "measure blood glucose," may be completed based on data recorded by wearable sensors that are automatically synchronized via a Bluetooth connection.

The interface illustrated in FIG. 13H also includes a lifestyle objective "self-report" that a patient must address manually either by an audio recording or a manual input. FIG. 13I illustrates an alternate interface for synchronizing sensor data, according to one embodiment. A patient may be presented with a notification panel prompting them to manually sync step data recorded via a wearable sensor, for example a fitness tracker. In such implementations, the TAC manager 470 may recognize that after a threshold period of time, no data has been received via an automatic data sync for a particular measurement. In the illustrated embodiment, the notification indicates a current step count compared to a target step count and a description prompting a patient to sync the step count.

In addition to recording nutrition and medication data, the interface generator 1130 presents an interface for a patient to record symptom data. FIG. 13J illustrates an interface for recording symptom data, according to one embodiment. The illustrated interface includes a list of potential symptoms (i.e., headache, cramps, excess urination, tiredness, numbness, and giddiness) and, for each symptom, a selectable severity indicator 1361. The severity indicator 1361 allows a user to specify the severity of one or more of their symptoms, for example high, medium, low, or none. In the illustrated interface, the "NONE" indicator is selected for each symptom to indicate that a patient is not experiencing any symptoms.

The interface generator 1230 may further generate an interface for a patient to record lifestyle data. FIG. 13K illustrates an interface for recording lifestyle data, according to one embodiment. The illustrated interface includes a list of questions to characterize a patient's current mental, emotional, and physical state, for example questions related to their energy or mood). For each question a patient may answer a question using a selectable rating indicator 1371. In the illustrated embodiment, a 5-star rating indicates a highest possible satisfaction, whereas a 1-star rating indicates a lowest possible satisfaction. In alternate embodiments, the rating indicator 1371 may be a range of numerical values or another metric.

Upon receiving the combination of nutrition data, medication data, symptom data, lifestyle data, and biological data using the interfaces described above with reference to FIGS. 13B-K and processing that data to confirm the completion of objectives outlined in the patient-specific recommendation, the interface generator 1130 may generate a user interface tracking a patient's progress over a given time period. The tracking interface illustrated in FIG. 13L may be an alternative representation of the information illustrated in FIG. 3B. For example, the tracking interface illustrated in FIG. 3B may be presented to a provider or coach via a provider device, whereas the tracking interface illustrated in FIG. 13J may be presented to a patient via a patient device. The illustrated interface of FIG. 13L may also be accessed by selecting the progress option 1308. The illustrated interface includes a selectable date option 1381 that, when selected, specifies the range of dates to present TAC information for. In the illustrated embodiment, the selectable date option 1381 is set to "daily." Accordingly, a TAC score is presented for a single day (i.e., May $24^{th}$) on the TAC graph 1382. TAC scores are presented on the TAC graph 1382 are illustrated as histograms 1383 ranging from 0 to 100. The actual numerical TAC score may be included above the histogram 1383 as illustrated in FIG. 12J. In an alternate embodiment in which the selectable date option 1381 was set to "Weekly," the TAC graph 1382 would include an additional six histograms with TAC scores from the preceding six days. Additionally, the interface includes a TAC score tracker 1384 that plots TAC scores for each day of a week. The TAC score tracker 1384 graphically illustrates changes in a patient's daily TAC scores, for example whether their TAC scores improved or deteriorated on a day-to-day basis or over the course of the week.

IV.F.3 Identification of Misreported Patient Data

Figure 14:
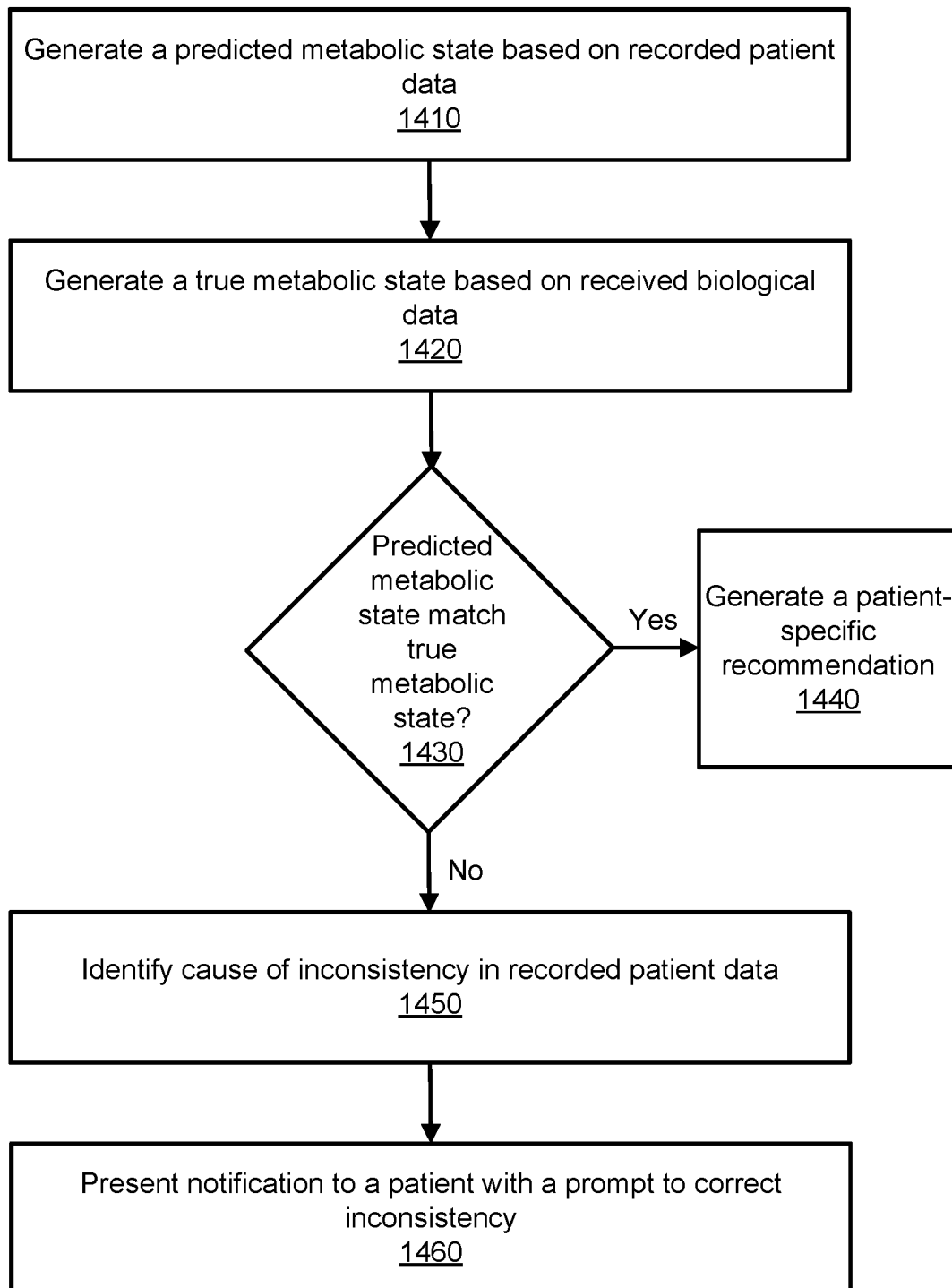
FIG. 14 is a flowchart illustrating a process for evaluating recorded patient data for inconsistencies, according to one embodiment.

FIG. 14 is a flowchart illustrating a process for evaluating recorded patient data for reporting errors, according to one embodiment. The patient health management platform 350 generates 1410 and 1420 a predicted metabolic state based on recorded patient data and a true metabolic state based on received biological data. TAC manager 470 compares 1430 the predicted metabolic state to the true metabolic state to evaluate whether the two metabolic states match. If the two metabolic states do match, the TAC manager 470 confirms the accuracy, timeliness, and completeness of the patient data recorded by the data logging module 1110 and generates 1440 a patient-specific recommendation, based on the patient's updated predicted metabolic state. If the two metabolic states do not match, the TAC manager 470 identifies 1450 the cause of the reporting error, for example a food item that was not recorded, a food item recorded in an incorrect quantity, or a food item recorded with an incorrect timestamp, and presents 1460 a notification to a patient with a prompt detailing the reporting error and inviting a patient to revise the recorded patient data to correct the error.

The response review module may implement one or more machine-learning models to automatically detect underreporting or misreporting of patient data from the patients as well as lack of adherence to the patient-specific recommendation. For example, a glucose impact model uses a patient's recorded food items, their nutrition data, and that patient's metabolic state to generate a predicted glucose spike for each meal. Simultaneously, the digital twin module 450 receives continuous glucose monitoring signals from sensors worn by the patient and calculates the true glucose spike for each meal. The response review module 1150 compares the predicted glucose spike with the true glucose spike. If the true spike is much larger than the predicted spike, for example above a threshold difference, the response review module 1150 flags the meal as having been underreported.

The TAC manager 470 may identify patients with a significant number of underreported meals, for example a number above a threshold amount, and informs a coach, provider, or both immediately when the number exceeds the threshold. Via a provider device, coaches or providers may reach out to the patient to encourage more accurate reporting and to correct the previous reporting errors. The resulting feedback loop encourages high patient adherence to their patient-specific recommendations.

In some implementations, errors identified by the TAC manager 470 may expose further physiological concerns previously unknown to a patient or medical provider. For example, a patient consumes a food item high in Potassium and records a data entry indicating that they consumed that food item. Accordingly, the digital twin module 450 generates a predicted metabolic state representative of the patient's potassium consumption, but the true metabolic state generated based on the biosignals recorded by sensor data and lab test data does not reflect the patient's potassium consumption. As an initial recourse, the response review module 1150 requests confirmation that the patient accurately recorded their consumption of the potassium-dense food item. In response to the patient confirming that their consumption of the food item, the response review module 1150 generates and communicates a notification to a medical provider flagging the inconsistency as potentially indicative of a metabolic abnormality, for example a patient's inability to metabolize potassium.

V. Additional Considerations

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of the above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method for tracking changes in a metabolic state of a patient, the method comprising:
   determining a representation of a metabolic state of a patient based on a plurality of biosignals recorded during a first time period and a timeline of patient data recorded during the first time period, the patient data comprising one or more of: 1) food items consumed by the patient throughout the first time period, 2) medication taken by the patient throughout the first time period, and 3) symptoms experienced by the patient throughout the first time period; and
   generating a patient-specific treatment recommendation for a second time period following the first time period, the patient-specific treatment recommendation identifying one or more objectives for the patient to complete to improve the metabolic state, wherein the objectives identify one or more of: 1) food items of a nutrition regimen to be consumed during the second time period and 2) medication of a medication regimen to be taken during the second time period;
   receiving, at periodic intervals throughout the second time period, recordings of patient data indicating one or more of: 1) food items consumed by the patient during the second time period and 2) medication taken by the patient during the second time period, the recordings of patient data recorded by patient using a patient device, wherein the recordings of patient data satisfy objectives identified in the patient-specific recommendation;
   determining, by a metabolic model, a predicted representation of the current metabolic state of the patient during the second time period based on the recordings of patient data received during the second time period, wherein the metabolic model is trained based on a training dataset of previous metabolic states of the patient and historical biosignals contributing to each previous metabolic state, and wherein the predicted representation is a patient-specific prediction indicating a current metabolic performance of the patient determined based on metabolic factors comprising blood glucose predictions, lifestyle data, and nutrition data;
   determining, by the metabolic model, a true representation of the current metabolic state of the patient during the second time period based on biosignals recorded by at least one wearable sensor worn by the patient or lab test data collected for the patient during the second time period;
   identifying a discrepancy in the recordings of patient data based on a comparison of the predicted representation of the current metabolic state and the true representation of the current metabolic state; and
   presenting, via a graphical user interface on the patient device, a notification informing the patient of the discrepancy, the notification including a score rating an adherence of the patient to the patient-specific treatment recommendations.

2. The method of claim 1, wherein the score is determined based on one or more of:
   a weighted metric representing an adherence of the patient to the nutrition regimen identified in the patient-specific treatment recommendation for the second time period;
   a weighted metric representing an adherence of the patient to the medication regimen identified in the patient-specific treatment recommendation for the second time period; and
   a weighted metric representing an adherence of the patient an activity regimen identified in the patient-specific treatment recommendation for the second time period.

3. The method of claim 1, further comprising:
   responsive to presenting the notification to the patient, receiving additional recordings of patient data indicating food consumed by the patient and medications taken by the patient;
   determining that the additional recordings of patient data indicate completion of one or more previously uncompleted objectives by the patient;
   increasing the score by a value representative of the one or more previously uncompleted objectives; and
   presenting, via a graphical user interface on the patient device, a notification illustrating the increased score.

4. The method of claim 1, wherein food items are categorized based on their impact on the metabolic state of the patient, the method further comprising:
   flagging a food item in a recording of patient data received during the second time period that will negatively impact the metabolic state of the patient based on a categorization of the food item; and
   generating, for display on the patient device, a notification recommending an alternate food item for the patient to consume, wherein the alternate food item shares nutritional similarities with the flagged food item.

5. The method of claim 1, further comprising:
   updating the representation of the metabolic state as patient data is recorded during the second time period;
   for each food item consumed during the second time period, determining a time delay between when the food item was consumed and when the food item was recorded as consumed based on the updated representation of the metabolic state; and
   updating the score based on the time delay, wherein a time delay exceeding a threshold timeframe penalizes the score.

6. The method of claim 1, further comprising:
   determining a level of similarity by comparing the predicted representation of the current metabolic state with the true representation of the current metabolic state; and
   responsive to the level of similarity being less than a threshold level of similarity, generating a notification for display on the patient device, the notification informing the patient of a discrepancy between the predicted representation of the current metabolic state and the true representation of the current metabolic state.

7. The method of claim 6, wherein the predicted representation of the current metabolic state of the patient is determined based on a predicted glucose spike as the patient consumes one or more food items and the true representation of the current metabolic state is determined based on continuously received glucose monitoring biosignals as the patient consumes the one or more food items.

8. The method of claim 6, further comprising:
   identifying a cause of the discrepancy between the predicted representation of the current metabolic state and the true representation of the current metabolic state, wherein the cause of the discrepancy is an error in a recording of patient data during the second time period; and updating the notification to describe the error and to request the patient to revise the recording of patient data to correct the error.

9. The method of claim 8, wherein the error in the recording of patient data is one or more of:
a food item that was not recorded;
a food item that was recorded as consumed at an incorrect time; and
a food item that was incorrectly recorded as a different food item.

10. The method of claim 8, further comprising:
receiving, from the patient device, a confirmation that the error is an accurate recording of the patient data; and
generating a notification to a medical provider flagging the discrepancy as potentially indicative of a metabolic abnormality.

11. The method of claim 6, further comprising:
responsive to the level of similarity satisfying the threshold level of similarity, generating a patient-specific treatment recommendation for a third time period following the second time period, the patient-specific treatment recommendation for the third time period identifying one or more objectives for the patient to complete to improve the current metabolic state; and
sending the patient-specific treatment recommendation for the third time period to the patient device.

12. A non-transitory computer readable medium storing instructions for tracking changes in a metabolic state of a patient encoded thereon that, when executed by a processor cause the processor to:
determine a representation of a metabolic state of a patient based on a plurality of biosignals recorded during a first time period and a timeline of patient data recorded during the first time period, the patient data comprising one or more of: 1) food items consumed by the patient throughout the first time period, 2) medications taken by the patient throughout the first time period, and 3) symptoms experienced by the patient throughout the first time period; and
generate a patient-specific treatment recommendation for a second time period following the first time period, the patient-specific treatment recommendation identifying one or more objectives for the patient to complete to improve the metabolic state, wherein the objectives identify one or more of: 1) food items of a nutrition regimen to be consumed during the second time period and 2) medications of a medication regimen to be taken during the second time period;
receive, at periodic intervals throughout the second time period, recordings of patient data indicating one or more of: 1) food items consumed by the patient during the second time period and 2) medications taken by the patient during the second time period, the recordings of patient data recorded by patient using a patient device, wherein the recordings of patient data satisfy objectives identified in the patient-specific recommendation;
determining, by a metabolic model, a predicted representation of the current metabolic state of the patient during the second time period based on the recordings of patient data received during the second time period, wherein the metabolic model is trained based on a training dataset of previous metabolic states of the patient and historical biosignals contributing to each previous metabolic state, and wherein the predicted representation is a patient-specific prediction indicating a current metabolic performance of the patient determined based on metabolic factors comprising blood glucose predictions, lifestyle data, and nutrition data;
determine, by the metabolic model, a true representation of a current metabolic state of the patient during the second time period based on biosignals recorded by at least one wearable sensor worn by the patient or lab test data collected for the patient during the second time period
identify a discrepancy in the recordings of patient data based on a comparison of the predicted representation of the current metabolic state and the true representation of the current metabolic state; and
present, via a graphical user interface on the patient device, a notification informing the patient of the discrepancy, the notification including a score rating an adherence of the patient to the patient-specific treatment recommendations.

13. The non-transitory computer readable medium of claim 12, wherein the score is determined based on one or more of:
a weighted metric representing an adherence of the patient to the nutrition regimen identified in the patient-specific treatment recommendation for the second time period;
a weighted metric representing an adherence of the patient to the medication regimen identified in the patient-specific treatment recommendation for the second time period; and
a weighted metric representing an adherence of the patient an activity regimen identified in the patient-specific treatment recommendation for the second time period.

14. The non-transitory computer readable medium of claim 12, wherein the instructions further cause the processor to:
responsive to presenting the notification to the patient, receive additional recordings of patient data indicating food consumed by the patient and medications taken by the patient;
determine that the additional recordings of patient data indicate completion of one or more previously uncompleted objectives by the patient;
increase the score by a value representative of the one or more previously uncompleted objectives; and
present, via a graphical user interface on the patient device, a notification illustrating the increased score.

15. The non-transitory computer readable medium of claim 12, wherein food items are categorized based on their impact on the metabolic state of the patient, the instructions further causing the processor to:
flag a food item in a recording of patient data received during the second time period that will negatively impact the metabolic state of the patient based on a categorization of the food item; and
generate, for display on the patient device, a notification recommending an alternate food item for the patient to consume, wherein the alternate food item shares nutritional similarities with the flagged food item.

16. The non-transitory computer readable medium of claim 12, wherein the instructions further cause the processor to:
update the representation of the metabolic state as patient data is recorded during the second time period;
for each food item consumed during the second time period, determine a time delay between when the food item was consumed and when the food item was recorded as consumed based on the updated representation of the metabolic state; and
update the score based on the time delay, wherein a time delay exceeding a threshold timeframe penalize the score.

17. The non-transitory computer readable medium of claim 12, wherein the instructions further cause the processor to:
determine a level of similarity by comparing the predicted representation of the current metabolic state with the true representation of the current metabolic state; and
responsive to the level of similarity being less than a threshold level of similarity, generate a notification for display on the patient device, the notification informing the patient of a discrepancy between the predicted representation of the current metabolic state and the true representation of the current metabolic state.

18. A system comprising:
one or more wearable sensors worn by a patient, each of the one or more wearable sensors configured to collected sensor data during a current time period;
an application stored on a patient device that presents metabolic insights generated for the patient; and
a non-transitory computer readable medium storing instructions for tracking changes in a metabolic state of a patient encoded thereon that, when executed by a processor cause the processor to:
determine a representation of a metabolic state of a patient based on a plurality of biosignals recorded during a first time period and a timeline of patient data recorded during the first time period, the patient data comprising one or more of: 1) food items consumed by the patient throughout the first time period, 2) medications taken by the patient throughout the first time period, and 3) symptoms experienced by the patient throughout the first time period; and
generate a patient-specific treatment recommendation for a second time period following the first time period, the patient-specific treatment recommendation identifying one or more objectives for the patient to complete to improve the metabolic state, wherein the objectives identify one or more of: 1) food items of a nutrition regimen to be consumed during the second time period and 2) medications of a medication regimen to be taken during the second time period;
receive, at periodic intervals throughout the second time period, recordings of patient data indicating one or more of: 1) food items consumed by the patient during the second time period and 2) medications taken by the patient during the second time period, the recordings of patient data recorded by patient using a patient device, wherein the recordings of patient data satisfy objectives identified in the patient-specific recommendation;
determining, by a metabolic model, a predicted representation of the current metabolic state of the patient during the second time period based on the recordings of patient data received during the second time period, wherein the metabolic model is trained based on a training dataset of previous metabolic states of the patient and historical biosignals contributing to each previous metabolic state, and wherein the predicted representation is a patient-specific prediction indicating a current metabolic performance of the patient determined based on metabolic factors comprising blood glucose prediction, lifestyle data, and nutrition data;
determine, by the metabolic model, a true representation of a current metabolic state of the patient during the second time period based on biosignals recorded by at least one wearable sensor worn by the patient or lab test data collected for the patient during the second time period;
identify a discrepancy in the recordings of patient data based on a comparison of the predicted representation of the current metabolic state and the true representation of the current metabolic state; and
present, via a graphical user interface on the patient device, a notification informing the patient of the discrepancy, the notification including a score rating an adherence of the patient to the patient-specific treatment recommendations.

19. The system of claim 18, wherein the score is determined based on one or more of:
a weighted metric representing an adherence of the patient to the nutrition regimen identified in the patient-specific treatment recommendation for the second time period;
a weighted metric representing an adherence of the patient to the medication regimen identified in the patient-specific treatment recommendation for the second time period; and
a weighted metric representing an adherence of the patient an activity regimen identified in the patient-specific treatment recommendation for the second time period.

20. The system of claim 18, wherein the instructions further cause the processor to:
responsive to presenting the notification to the patient, receive additional recordings of patient data indicating food consumed by the patient and medications taken by the patient;
determine that the additional recordings of patient data indicate completion of one or more previously uncompleted objectives by the patient;
increase the score by a value representative of the one or more previously uncompleted objectives; and
present, via a graphical user interface on the patient device, a notification illustrating the increased score.

21. The system of claim 18, wherein food items are categorized based on their impact on the metabolic state of the patient, the instructions further causing the processor to:
flag a food item in a recording of patient data received during the second time period that will negatively impact the metabolic state of the patient based on a categorization of the food item; and
generate, for display on the patient device, a notification recommending an alternate food item for the patient to consume, wherein the alternate food item shares nutritional similarities with the flagged food item.

22. The system of claim 18, wherein the instructions further cause the processor to:
update the representation of the metabolic state as patient data is recorded during the second time period;
for each food item consumed during the second time period, determine a time delay between when the food item was consumed and when the food item was recorded as consumed based on the updated representation of the metabolic state; and
update the score based on the time delay, wherein a time delay exceeding a threshold timeframe penalizes the score.

23. The system of claim 18, wherein the instructions further cause the processor to:
- determine a level of similarity by comparing the predicted representation of the current metabolic state with the true representation of the current metabolic state; and
- responsive to the level of similarity being less than a threshold level of similarity, generate a notification for display on the patient device, the notification informing the patient of a discrepancy between the predicted representation of the current metabolic state and the true representation of the current metabolic state.

24. The method of claim 1, further comprising:
- updating the training dataset with the determined true representation of the current metabolic state and the biosignals recorded by at least one wearable sensor worn by the patient or lab test data collected for the patient during the second time period; and
- iteratively training the patient-specific metabolic model based on the updated training dataset.

* * * * *

UNITED STATES PATENT AND TRADEMARK OFFICE
CERTIFICATE OF CORRECTION

| | |
|---|---|
| PATENT NO. | : 11,350,876 B2 |
| APPLICATION NO. | : 17/202354 |
| DATED | : June 7, 2022 |
| INVENTOR(S) | : Poon et al. |

It is certified that error appears in the above-identified patent and that said Letters Patent is hereby corrected as shown below:

On the Title Page

On Page 2, Item (57), in Column 1, under "Abstract", Line 6, delete "n adherence" and insert -- an adherence --, therefor.

On Page 2, Item (57), in Column 1, under "Abstract", Line 8, delete "based the" and insert -- based on the --, therefor.

In the Claims

In Column 61, in Claim 1, Line 40, delete "the current" and insert -- a current --, therefor.

In Column 64, in Claim 12, Line 10, delete "period" and insert -- period; --, therefor.

In Column 64, in Claim 14, Line 41, delete "determine" and insert -- determining --, therefor.

Signed and Sealed this
Twenty-eighth Day of February, 2023

Katherine Kelly Vidal
*Director of the United States Patent and Trademark Office*